US012258625B2

United States Patent
Cifuentes Buira et al.

(10) Patent No.: US 12,258,625 B2
(45) Date of Patent: Mar. 25, 2025

(54) COMPOSITIONS AND METHODS RELATING TO NUCLEIC ACID INTERACTION REPORTERS

(71) Applicant: Trustees of Boston University, Boston, MA (US)

(72) Inventors: Daniel Cifuentes Buira, Sharon, MA (US); Dmitry Kretov, Boston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 38 days.

(21) Appl. No.: 18/130,560

(22) Filed: Apr. 4, 2023

(65) Prior Publication Data

US 2023/0340582 A1 Oct. 26, 2023

Related U.S. Application Data

(60) Provisional application No. 63/428,459, filed on Nov. 29, 2022, provisional application No. 63/328,360, filed on Apr. 7, 2022.

(51) Int. Cl.
| | | |
|---|---|---|
| *C12Q 1/68* | (2018.01) | |
| *A61K 38/50* | (2006.01) | |
| *C12N 9/78* | (2006.01) | |
| *C12N 15/10* | (2006.01) | |
| *C12N 15/62* | (2006.01) | |
| *C12Q 1/6869* | (2018.01) | |
| *G01N 33/00* | (2006.01) | |
| *G01N 33/53* | (2006.01) | |

(52) U.S. Cl.
CPC ............. *C12Q 1/6869* (2013.01); *C12N 9/78* (2013.01)

(58) Field of Classification Search
CPC .......... C12N 9/78; C12N 15/10; C12N 15/62; A61K 38/50
See application file for complete search history.

(56) References Cited

U.S. PATENT DOCUMENTS

| | | |
|---|---|---|
| 2019/0382755 A1 | 12/2019 | Poma et al. |
| 2019/0390186 A1 | 12/2019 | Rosbash et al. |
| 2020/0291383 A1 | 9/2020 | Mandel et al. |
| 2021/0095296 A1 | 4/2021 | Amit et al. |
| 2022/0195416 A1* | 6/2022 | Wang .................... C12N 15/62 |

FOREIGN PATENT DOCUMENTS

| | | |
|---|---|---|
| WO | 2016148994 A1 | 9/2016 |
| WO | 2020018509 A2 | 1/2020 |

OTHER PUBLICATIONS

Brannan et al. "Robust single-cell discovery of RNA targets of RNA-binding proteins and ribosomes." Nature methods vol. 18,5 (2021): 507-519.
McMahon et al. "TRIBE: Hijacking an RNA-Editing Enzyme to Identify Cell-Specific Targets of RNA-Binding Proteins." Cell vol. 165,3 (2016): 742-53.
Rodriques et al. "RNA timestamps identify the age of single molecules in RNA sequencing." Nature biotechnology vol. 39,3 (2021): 320-325.
Lu et al. "Types of nuclear localization signals and mechanisms of protein import into the nucleus." Cell Commun Signal 19:60 (2021).
Lubelsky et al. "High-resolution mapping of function and protein binding in an RNA nuclear enrichment sequence" The EMBO Journal 40:e106357 (2021).
Shukla et al. "High-throughput identification of RNA nuclear enrichment sequences." The EMBO Journal 37:e98452 (2018).

* cited by examiner

*Primary Examiner* — Maryam Monshipouri
(74) *Attorney, Agent, or Firm* — Nixon Peabody LLP; Ronald I. Eisenstein; Nicole D. Kling

(57) ABSTRACT

The technology described herein is directed to compositions, methods, and systems for measuring the interactions between RNAs and proteins.

24 Claims, 36 Drawing Sheets

Specification includes a Sequence Listing.

FIG. 2C gggcccCtatCCAacgcAattcTGGcacGTCCAATCCAATCCAATCCA
cccgggGataGGTtgcgTtaagACCgtgCAGGTTAGGTTAGGTTAGGT

| | Xcm1 | recorder 5p | gggcccCtatCCAacgcAattcTGGcacGTCCAATCCAATCCAATCCA
GGGCCCCTATCCAACGCAATTCTGGCACGTCCAATCCAATCCAATCCA

GGGCCCCTATCCAACGCAATTCTGGCACGTCCAATCCAATCCAATCCA

```
                        ADAR substrate for editing
ATCCAATCCAAttaaaTTAGATTAGATTAGATTAGATTAGATTAGACa
+++++++++++++++|+++++++++++++++|+++++++++++++++|+++++++++++++++|+++++++++++++++|
TAGGTTAGGTTaatttAATCTAATCTAATCTAATCTAATCTAATCTGt
                                recorder 3p
      recorderloop
```

ATCCAATCCAAttaaaTTAGATTAGATTAGATTAGATTAGATTAGACa
ATCCAATCCAATTAAATTAGATTAGATTAGATTAGATTAGATTAGACA

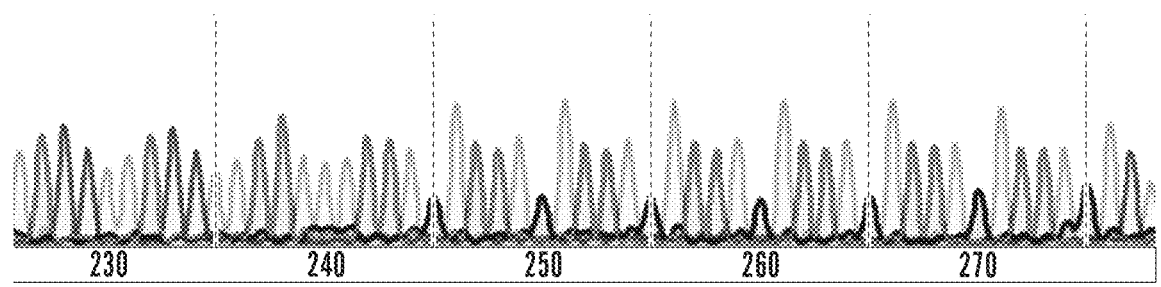

ATCCAATCCAATTAAATTAGATTAGATTGGATTAGATTAGATTAGACA

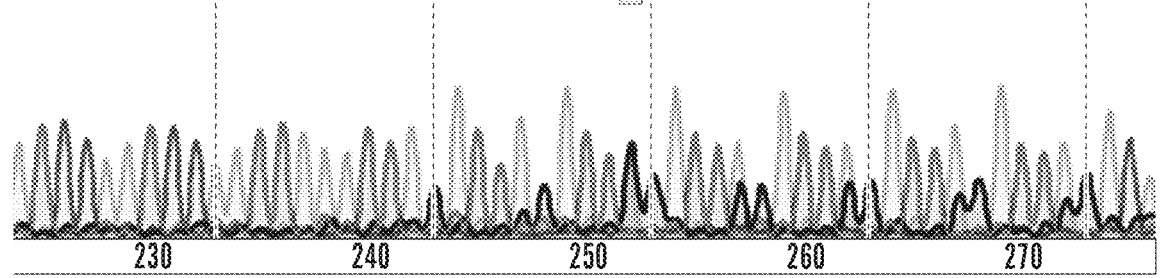

Editing sites

*FIG. 9B (cont.)*

Pumilio (Pum1) binding motif:

Position of each of the 4 main Pum1 motifs after ranking all 65,536 from most edited to least edited:

|  | Pum1 | | HuR | | Ago2 | | Control | |
| --- | --- | --- | --- | --- | --- | --- | --- | --- |
|  | Rep 1 | Rep 2 | Rep 1 | Rep 2 | Rep 1 | Rep 2 | Rep 1 | Rep 2 |
| UGUAAUAU | 1 | 4 | 33658 | 30405 | 8373 | 18302 | 1954 | 22905 |
| UGUACUAU | 2 | 8 | 33642 | 30339 | 19270 | 19270 | 19181 | 24407 |
| UGUAUUAU | 67 | 3 | 31994 | 6420 | 28302 | 8375 | 19066 | 24770 |
| UGUAGUAU | 197 | 25803 | 93637 | 6070 | 8318 | 8330 | 19215 | 24345 |

COMPOSITIONS AND METHODS RELATING TO NUCLEIC ACID INTERACTION REPORTERS

CROSS-REFERENCE TO RELATED APPLICATIONS

This application claims benefit under 35 U.S.C. § 119(e) of U.S. Provisional Application No. 63/428,459 filed Nov. 29, 2022 and 63/328,360 filed Apr. 7, 2022, the contents of which are incorporated herein by reference in their entireties.

SEQUENCE LISTING

The instant application contains a Sequence Listing which has been submitted electronically in XML file format and is hereby incorporated by reference in its entirety. Said XML copy, created on May 5, 2023, is named 701586-191810US-PT_SL.xml and is 116,362 bytes in size.

TECHNICAL FIELD

The technology described herein relates to methods and compositions for detecting and measuring the interactions between proteins and RNAs.

BACKGROUND

The translation of mRNAs into proteins is a fundamental biological process. In all organisms and disease, this process is regulated by proteins that bind the RNA (RNA-binding proteins) and which thereby regulate the processing, translation, and degradation of the RNA. Understanding the interaction of these RNA-binding proteins and the RNAs is critical to permit improved therapeutic strategies.

Prior art methods of measuring these interactions rely on engineered proteins that target endogenous mRNAs and then sequencing mRNA product molecules to detect the effects the engineered proteins cause. These systems are limited by the fact that the endogenous mRNAs are often not suitable targets for the engineered proteins.

SUMMARY

The compositions and methods described herein utilize a paired protein and mRNA approach that provides reliable targets for the protein. This permits universal study of protein-mRNA binding interactions with high sensitivity. Additionally, the currently described technology provides combinations of multiple proteins and/or mRNAs that permit the study of the protein-mRNA interaction itself (as well as modifiers of that interaction). This is a different kind of output than the measuring the mere existence or lifespan of the mRNA.

Accordingly, in one aspect of any of the embodiments, described herein is a combination comprising a) at least one polypeptide or pair of polypeptides comprising i) a candidate RNA-binding domain and ii) a catalytic domain of an RNA-editing enzyme; and b) at least one RNA comprising i) at least one candidate cognate binding site for the candidate RNA-binding domain and ii) at least one cognate substrate site for the catalytic domain.

In some embodiments of any of the aspects, the combination comprises a plurality of polypeptides or pair of polypeptides collectively comprising a plurality of candidate RNA-binding domains. In some embodiments of any of the aspects, a plurality of polypeptides or pair of polypeptides collectively comprising a plurality of candidate RNA-binding domains; and one RNA comprising a cognate binding site. In some embodiments of any of the aspects, the combination comprises a plurality of RNAs collectively comprising a plurality of candidate cognate binding sites. In some embodiments of any of the aspects, the combination comprises one polypeptide or pair of polypeptides comprising a RNA-binding domain; and a plurality of RNAs collectively comprising a plurality of candidate cognate binding sites.

In some embodiments of any of the aspects, the i) at least one candidate cognate binding site for the candidate RNA-binding domain and ii) at least one cognate substrate site for the catalytic domain are not found in the same naturally-occurring RNA.

In some embodiments of any of the aspects, the candidate RNA-binding domain comprises: one or more PUF domains, one or more RNA-binding domains of Argonaute, one or more RNA-binding domains of lambda N, one or more REC domains of Cas, or a ribosomal protein. In some embodiments of any of the aspects, the candidate RNA-binding domain and the candidate cognate binding site comprise:
  a) one or more RNA-binding domains of lambda N and a viral hairpin B-Box;
  b) a series of 6 to 16 PUF domains (preferably 8 or 9 domains) and a corresponding series of nucleotides;
  c) a series of 8 to 9 PUF domains and a corresponding series of nucleotides;
  d) one or more RNA-binding domains of Argonaute and a reverse complement sequence of the small non-coding RNA bound by the RNA-binding domain of Argonaute;
  e) one or more REC domains of Cas and a CRISPR sequence, guideRNA, or sgRNA; or
  f) a YTH domain and a m6A methylation site.

In some embodiments of any of the aspects, the candidate RNA-binding domain comprises a RNA-binding domain of Argonaute, the candidate cognate binding site comprises a reverse complement sequence of the small non-coding RNA bound by the RNA-binding domain of Argonaute, and the combination further comprises the small non-coding RNA. In some embodiments of any of the aspects, the candidate RNA-binding domain comprises a ribosomal protein and the at least one RNA further comprises a sequence encoding a reporter gene. In some embodiments of any of the aspects, the catalytic domain comprises the catalytic domain of ADAR, APOBEC, Abe7.10, or Cas (e.g., Cas13). In some embodiments of any of the aspects, the catalytic domain comprises ADAR or APOBEC. In some embodiments of any of the aspects, the ADAR is *Danio rerio* ADAR. In some embodiments of any of the aspects, the ADAR is human ADAR. In some embodiments of any of the aspects, the catalytic domain and the cognate substrate site comprise:
  a) the catalytic domain of ADAR and a hairpin substrate site comprising adenosine nucleotides;
  b) the catalytic domain of ADAR and a hairpin substrate site comprising at least one adenosine nucleotide mismatched with a cytosine nucleotide;
  c) the catalytic domain of APOBEC and a single-stranded substrate site comprising at least one cytosine nucleotide.

In some embodiments of any of the aspects, the at least one RNA comprises a plurality of tandem repeats of the cognate substrate site. In some embodiments of any of the aspects, the at least one RNA comprises a plurality of tandem repeats of the cognate binding site.

In some embodiments of any of the aspects, the at least one RNA further comprises one or more sequencing adaptor sequences. In some embodiments of any of the aspects, the at least one RNA comprises, from 5' to 3':
  a) at least one sequencing adaptor sequence;
  b) the at least one candidate cognate binding site for the candidate RNA-binding domain and the at least one cognate substrate site for the catalytic domain, in either relative order; and
  c) at least one sequence adaptor sequence.

In some embodiments of any of the aspects, the at least one RNA further comprises a barcode sequence. In some embodiments of any of the aspects, the at least one RNA further comprises a nuclear enrichment or nuclear localization sequence. In some embodiments of any of the aspects, the at least one RNA further comprises a 3' sequence. In some embodiments of any of the aspects, the at least one RNA further comprises a polyA sequence. In some embodiments of any of the aspects, the 3' sequence comprises SEQ ID NO: 1 or 2.

In some embodiments of any of the aspects, a single polypeptide comprises the candidate RNA-binding domain and the catalytic domain of a RNA-editing enzyme.

In some embodiments of any of the aspects, a pair of polypeptides comprises the candidate RNA-binding domain and the catalytic domain of a RNA-editing enzyme, and the pair of polypeptides comprises:
  a) a bait polypeptide comprising: a first candidate interaction domain and the candidate RNA-binding domain; and
  b) a prey polypeptide comprising: a second candidate interaction domain and the catalytic domain of a RNA-editing enzyme.

In one aspect of any of the embodiments, described herein is a cell comprising or expressing the combination described herein.

In one aspect of any of the embodiments, described herein is a method of detecting the strength of the binding of a candidate RNA-binding domain to a candidate cognate binding site, the method comprising:
  a) contacting the at least one polypeptide described herein with the at least one RNA of any described herein for a period of time; and
  b) detecting the amount of editing present in the cognate substrate site.

In one aspect of any of the embodiments, described herein is a method of detecting the strength of the binding of a candidate RNA-binding domain to a candidate cognate binding site, the method comprising:
  a) contacting the at least one polypeptide described herein with the at least one RNA described herein for a period of time; and then
  b) detecting the amount of editing present in the cognate substrate site.

In some embodiments of any of the aspects, the amount of editing generated during the period of time correlates to the strength of the binding. In some embodiments of any of the aspects:
  a) the catalytic domain is a catalytic domain of ADAR and the amount of editing is the number of A to I edits;
  b) the catalytic domain is a catalytic domain of APOBEC and the amount of editing is the number of C to U edits.

In some embodiments of any of the aspects, the detecting comprises sequencing of the at least one RNA; fluorescence detection; or reporter gene detection. In some embodiments of any of the aspects, the detecting comprises high-throughput sequencing of the at least one RNA. In some embodiments of any of the aspects, step a) further comprises contacting the polypeptide and RNA with a drug candidate, a candidate RNA-editing inhibitor, or a candidate RNA-editing agonist.

In some embodiments of any of the aspects, the method further comprises performing steps a) and b) for a plurality of different polypeptides or RNAs to determine relative binding strength or editing activity. In some embodiments of any of the aspects, the plurality of different polypeptides comprise different sequences or modifications in the RNA-binding domain. In some embodiments of any of the aspects, the plurality of different polypeptides comprise different post-translational modifications in the RNA-binding domain. In some embodiments of any of the aspects, the plurality of different RNAs comprise different sequences or modifications in the cognate binding site. In some embodiments of any of the aspects, the contacting step occurs in a cell or organism.

BRIEF DESCRIPTION OF THE DRAWINGS

FIGS. 2A-2C depict an exemplary recorder configuration. FIG. 2A depicts a schematic of the individual components of the recorder mRNA. FIG. 2B depicts an exemplary secondary structure of the recorder hairpin, with the potential editing sites indicated in black. The fully edited hairpin is a perfect complementary stem. The hairpin is depicted before (left; SEQ ID NO: 58) and after (right; SEQ ID NO: 59) editing. FIG. 2C depicts the sequence of the exemplary recorder mRNA (SEQ ID NO 60). The RBP-binding site sequence is for illustration purposes only. This sequence can be changed to match the appropriate binding site of the RBP under test. In alternative embodiments, multiple different recorder mRNAs can be utilized, each with a different RBP-binding site sequence, e.g, which upon exposure to the writer component will indicate which sequence(s) are preferred.

FIG. 3A depicts a schematic of transfecting the recorder with the RBP-binding site of interest to determine endogenous editing activity. FIG. 3B depicts a schematic of co-transfecting the RBP-Adar fusion with an "empty" recorder, a recorder that does not contain a putative binding site for the given RBP. FIG. 3C shows that only when the RBP-Adar fusion is co-transfected together with a recorder with the RBP-binding site, editing should be observed. FIG. 3D depicts data from interactome recorder with TDP-43. Only in the presence of the 12×UG repeats, the target site for TDP-43, is editing of the recorder seen. The editing is show in the Sanger sequencing trace by a double peak of adenine and guanosines at the indicated positions. The higher the guanosine peak, the higher the editing. FIG. 3D discloses SEQ ID NOS 30-33, 30, 31, 34, 30, 31, 35-36, 35, 37, 35, 38-39, 38, 38, 40, respectively, in order of appearance.

FIG. 8B discloses SEQ ID NOS 41-47, 46, 46, 46, 48-49, 48, 50, 48, respectively, in order of appearance.

FIG. 9B discloses SEQ ID NOS 51-52, 51, 51, 51, 53-54, 53, 53, 53, 55-56, 55, 55, 57, respectively, in order of appearance.

FIG. 13A) Cartoon showing the two main components of the Interactome Recorder system: the writer and the recorder. Only when both components are brought together via the interaction between an RNA-binding domain of a protein and a RNA motif, is editing of the Adar substrate observed. The editing consists in A-to-G mutations in the sequence of the Adar substrate. FIG. 13B) Secondary structure of the Adar substrate, showing the position of the main editing sites. FIG. 13B discloses SEQ ID NO: 61.

FIG. 22A) A library of recorders containing all 65,536 possible 8 nucleotides long motifs was generated. Next, the recorder library together with a RBP-Adar fusion of interest was injected into zebrafish embryos or transfected into cells. High-throughput sequencing of the recorder after incubation and ranking according to the number of edits reveals which motifs are preferentially bound by the RBP of interest. FIG. 22B) Sequence of the 8-nucleotide motifs preferentially bound by Pumilio (Pum1). FIG. 22C) Position of the Pumilio motifs in a ranking of the most edited motif library after the library is exposed to Pumilio, HuR, Ago2 or no RBP. Only when the motif recorder library is co-injected with Pumilio, are the Pumilio motifs observed rising to the top edited positions.

FIG. 24A) Cartoon of the recorder with fluorescent read-out. FIG. 24B) Experiment done in zebrafish embryos where the fluorescent recorder with BoxB site is injected alone or together with N22-Adar fusion. Only in the latter case are fluorescent embryos observed in the EYFP channel, equivalent to a control reporter without stop codon. FIG. 24C) Experiment done in human HEK293 cells with the fluorescent recorder with the binding site for the human RBP TDP-43. Only when the recorder and TDP43-Adar fusion are expressed together, is fluorescence derived from the EYFP protein observed.

DETAILED DESCRIPTION

Figure 1:
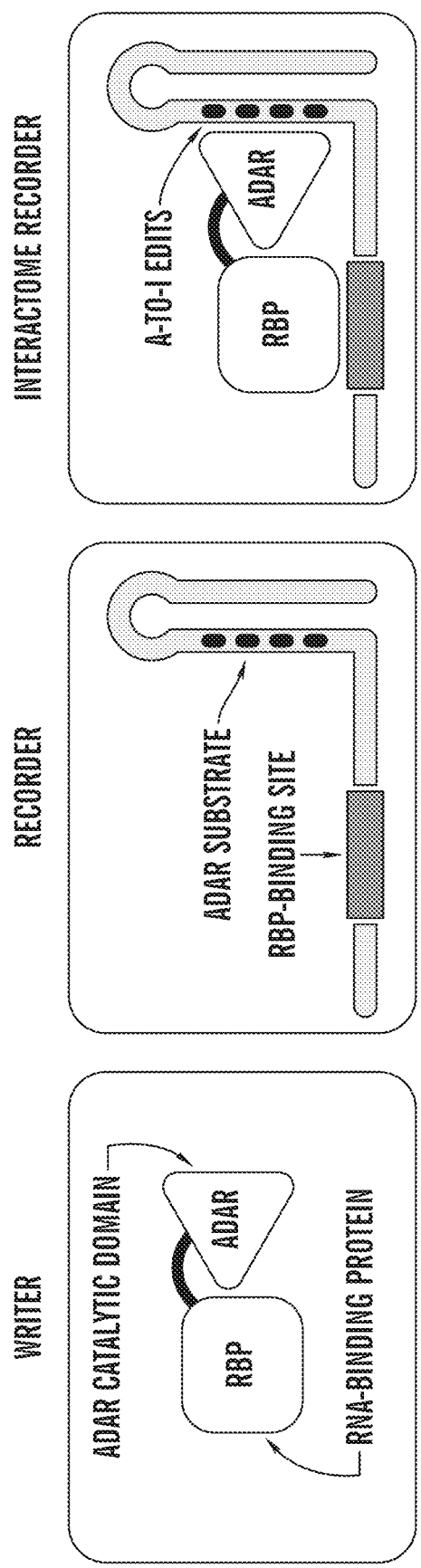
FIG. 1 depicts a schematic of the individual components of the interactome recorder system and how they come together in the reporter to record RNA-protein interactions. The writer is a polypeptide, the recorder is an RNA chain.

Embodiments of the technology described herein provide combinations, systems, and methods for measuring the strength of RNA-binding domain-cognate binding site interactions. Prior art methods rely on endogenous mRNAs. Additionally, the instant embodiments provide quantitative results, which are not achievable with techniques such as TRIBE (Targets of RNA-binding proteins identified by editing) that only provide binary outputs. Furthermore, the instant technology is unbiased, which provides an advantage over techniques such as CLIP (cross-linking and immunoprecipitation method and its variants) which introduces a significant bias in its results because the method relies on covalent cross-linking of the RNA and the protein with UV irradiation. The current technology can provide screening to identify RNA-binding domain-cognate binding site identity and interaction strength, but can also be utilized to screen for compounds (e.g., drugs, antibiotics, or herbicides) that modulate RNA-binding domain-cognate binding site interactions.

In one aspect of any of the embodiments, described herein is a combination comprising:
a) at least one polypeptide or pair of polypeptides comprising i) a candidate RNA-binding domain and ii) a catalytic domain of an RNA-editing enzyme; and
b) at least one RNA comprising i) at least one candidate cognate binding site for the candidate RNA-binding domain and ii) at least one cognate substrate site for the catalytic domain.

In one aspect of any of the embodiments, described herein is a combination comprising:
a) at least one polypeptide or pair of polypeptides comprising i) a RNA-binding domain and ii) a catalytic domain of an RNA-editing enzyme; and
b) at least one RNA comprising i) at least one candidate cognate binding site for the candidate RNA-binding domain and ii) at least one cognate substrate site for the catalytic domain.

In one aspect of any of the embodiments, described herein is a combination comprising:
a) at least one polypeptide or pair of polypeptides comprising i) a candidate RNA-binding domain and ii) a catalytic domain of an RNA-editing enzyme; and
b) at least one RNA comprising i) at least one cognate binding site for the candidate RNA-binding domain and ii) at least one cognate substrate site for the catalytic domain.

In one aspect of any of the embodiments, described herein is a combination comprising:
a) at least one polypeptide or pair of polypeptides comprising i) a RNA-binding domain and ii) a catalytic domain of an RNA-editing enzyme; and
b) at least one RNA comprising i) at least one cognate binding site for the RNA-binding domain and ii) at least one cognate substrate site for the catalytic domain.

In some embodiments of any of the aspects, a single polypeptide comprises the RNA-binding domain (or candidate RNA-binding domain) and catalytic domain of an RNA-editing enzyme. In some embodiments of any of the aspects, a single RNA comprises the cognate binding site for the RNA-binding domain (or candidate cognate binding site for the RNA-binding domain) and the cognate substrate site for the catalytic domain.

As used herein, a "RNA-binding domain" refers to a domain that binds to RNA. The RNA binding domain can bind to ssRNA or dsRNA. A variety of RNA-binding domains are known in the art and detailed below. The structures, sequences, and binding specificities of RNA-binding proteins are known in the art. For further discussion see, e.g., Corley et al. Mol Cell 2020 78:9-29 (PMID 32243832) (which documents over 2,000 RNA-binding proteins); Gerstberger et al. Nat Rev Genet 2014 15:829-45 (PMID 25365966) (which provides a census of 1,542 RNA-binding proteins); and Castello et al. Cell 2012 149:1393-1406 (PMID 22658674) (which identifies 860 RNA-binding proteins); each of which is incorporated by reference herein in its entirety. Exemplary RNA binding domain sequences and alignments are also available in the NCBI data base at NCBI ID NO: 450164 (e.g., Accession No. cl17169).

Non-limiting examples of RNA-binding domains are RNA recognition motifs (RRM), dsRNA binding domains (dsRM or dsRBD), and zinc finger domains. The RRM comprises a four-stranded beta sheet and two alpha helices and each tends to directly bind a 2-3 nucleotide sequence. Further discussion of the RRM can be found, e.g., in Stefl et al. EMBO Reports 2005 6 (1): 33-8; which is incorporated by reference herein in its entirety. The dsRM interact with RNA duplexes via 2 alpha helices and a beta1-beta2 loop. Further discussion of the dsRM can be found, e.g., in Stefl et al. EMBO Reports 2005 6 (1): 33-8; which is incorporated by reference herein in its entirety. Zinc finger domains provide very high sequence specificity and tend to bind ssRNA. Further discussion of zinc fingers can be found, e.g., in Stefl et al. EMBO Reports 2005 6 (1): 33-8; which is incorporated by reference herein in its entirety. Further examples of RNA-binding domains and their sequences can be found, e.g., in the Eukaryotic RNA Binding Protein Database (EuRBPDB), see Liao et al. Nuc Acids Res 2020 48:D307-13; which is incorporated by reference herein in its entirety.

In some embodiments of any of the aspects, the RNA-binding domain (e.g., the candidate RNA-binding domain) comprises one or more Transactive Response DNA binding protein 43 (TDP-43 or TARDBP) RRMs. TDP-43 comprises 2 RRMs, e.g, SEQ ID NOs: 18 and 19 below. The RRMs of TDP-43 bind U G/T G repeats, typically in the 3' URT of mRNAs. The structure, sequence, and function of TDP-43 RRMs and their cognate binding sites (U G/T G repeats) are known in the art. Individual sequences of TDP-43 and exemplary TDP-43 RRMs are available in the NCBI database under NCBI ID No. 23435 and NP 031401.1 (SEQ ID NO: 20). For more discussion see, e.g., Qin et al. PNAS 111(52):18619-18624 (2014); Prasad et al. Frontiers in Molecular Neuroscience 12:25 (2019), each of which is incorporated by reference herein in its entirety.

```
(RRM1 of TDP-43)
                                        SEQ ID NO: 18
    qktsdlivlg lpwktteqdl keyfstfgev lmvqvkkdlk tghskgfgfv rfteyetqvk vmsqrhmidg rwcdcklp (RRM2 of TDP-43)
                                        SEQ ID NO: 19
    rkvfvgrcte dmtedelref fsqygdvmdv fipkpfrafa fvtfaddqia qslcgedlii kgisvhisna e
```

In some embodiments of any of the aspects, a RNA-binding domain comprises a TDP-43 RRM domain (e.g., SEQ ID NO: 18 or 19). In some embodiments of any of the aspects, a RNA-binding domain consists of a TDP-43 RRM domain (e.g., SEQ ID NO: 18 or 19). In some embodiments of any of the aspects, a RNA-binding domain consists essentially of a TDP-43 RRM domain (e.g., SEQ ID NO: 18 or 19). In some embodiments of any of the aspects, a polypeptide comprising a RNA-binding domain comprises an TDP-43 protein (e.g., SEQ ID NO: 20). In some embodiments of any of the aspects, a polypeptide comprising a RNA-binding domain comprises a full-length TDP-43 protein (e.g., SEQ ID NO: 20). In some embodiments of any of the aspects, a polypeptide comprising a RNA-binding domain comprises an TDP-43 protein (e.g., SEQ ID NO: 20). In some embodiments of any of the aspects, a polypeptide comprising a RNA-binding domain comprises a full-length TDP-43 protein (e.g., SEQ ID NO: 20).

```
                                        SEQ ID NO: 20
  1  mseyirvted endepieips eddgtvllst vtaqfpgacg lryrnpvsqc mrgvrlvegi 61  lhapdagwgn lvyvvnypkd nkrkmdetda ssavkvkrav qktsdlivlg lpwktteqdl 121  keyfstfgev lmvqvkkdlk tghskgfgfv rfteyetqvk vmsqrhmidg rwcdcklpns 181  kqsqdeplrs rkvfvgrcte dmtedelref fsqygdvmdv fipkpfrafa fvtfaddqia 241  qslcgedlii kgisvhisna epkhnsnrql ersgrfggnp ggfgnqggfg nsrgggaglg 301  nnqgsnmggg mnfgafsinp ammaaaqaal qsswgmmgml asqqnqsgps gnnqnqgnmq 361  repnqafgsg nnsysgsnsg aaigwgsasn agsgsgfngg fgssmdskss gwgm
```

In some embodiments of any of the aspects, a cognate binding site for an RNA-binding domain comprising one or more TDP-43 RRMs comprises one or more U G/T G repeats. In some embodiments of any of the aspects, a cognate binding site for an RNA-binding domain comprising one or more TDP-43 RRMs consists of one or more U G/T G repeats.

In some embodiments of any of the aspects, the RNA-binding domain (e.g., the candidate RNA-binding domain) comprises one or more PUF domains, an RNA-binding domain of Argonaute, a RNA-binding domain of lambda N, a REC domain of Cas, an Embryonic Lethal Abnormal Vision (ELAV) RNA recognition motif (RRM), or a ribosomal protein.

In some embodiments of any of the aspects, the RNA-binding domain (e.g., the candidate RNA-binding domain) comprises one or more PUF domains. As used herein, "PUF domain" or "Pumilio/fem-3 mRNA binding factor domain" refers to a RNA-binding domain of a PUF protein or derived from a PUF protein, i.e., a domain comprising a plurality of alpha-helices forming a crescent-shaped structure. The structure, sequence, and function of numerous PUF domains and their binding specificities are known in the art, including libraries of PUF domains and engineered PUF domains with desired specificities. Individual sequences and alignments of exemplary PUF domains are available in the NCBI database under NCBI ID Nos. 425878, 453019, 227430, and 153420 (e.g., Accession Nos. pfam00806, cl29546, COG5099, and cd07920). For more discussion see, e.g., Zhao et al. Nucleic Acids Research 2018 46:4771-4782 (PMID 29490074); Wang et al. Int. J Mol Sci 2018 19:410; Zhou et al. Nature Communications 2021 12:5107; Porter et al. PNAS 2015 112:15868-15873; and Abil et al. Journal of Biological Engineering 2014 8:7; each of which is incorporated by reference herein in its entirety.

Non-limiting, exemplary PUF domain sequences are SEQ ID NOs: 4-11.

```
                                        SEQ ID NO: 4
    GNYVIQKFFEFgsLEQKLALAER

SEQ ID NO: 5
    HVLSLALQmYGCRVIQKALEFI

SEQ ID NO: 6
    NGNHVVQKCIEC

SEQ ID NO: 7
    VFALSTHpYGCRVIQRILEHC

SEQ ID NO: 8
    QYGNYVIQHVLEHG

SEQ ID NO: 9
    NVLVLSQHKFASNVVEKCVTH

SEQ ID NO: 10
    ALYTMMKDQYANYVVQKMIDVA

SEQ ID NO: 11
    YGKHILAKL
```

In some embodiments of any of the aspects, a PUF domain comprises two or more alpha helices, e.g., PUF repeats. In some embodiments of any of the aspects, a PUF domain comprises three or more alpha helices, e.g., PUF repeats. In some embodiments of any of the aspects, a PUF domain comprises four or more alpha helices, e.g., PUF repeats. In some embodiments of any of the aspects, a PUF domain comprises five or more alpha helices, e.g., PUF repeats. In some embodiments of any of the aspects, a PUF domain comprises six or more alpha helices, e.g., PUF repeats. In some embodiments of any of the aspects, a PUF domain comprises 6 to 20 alpha helices, e.g., PUF repeats. In some embodiments of any of the aspects, a PUF domain comprises 6 to 16 alpha helices, e.g., PUF repeats. In some embodiments of any of the aspects, a PUF domain comprises 7 to 10 alpha helices, e.g., PUF repeats. In some embodiments of any of the aspects, a PUF domain comprises 8 or 9 alpha helices, e.g., PUF repeats.

In some embodiments of any of the aspects, a RNA-binding domain comprises a PUF domain or PUF repeat. In some embodiments of any of the aspects, a RNA-binding domain consists of a PUF domain or PUF repeat. In some embodiments of any of the aspects, a RNA-binding domain consists essentially of a PUF domain or PUF repeat. In some embodiments of any of the aspects, a polypeptide comprising a RNA-binding domain comprises a PUF protein. In some embodiments of any of the aspects, a polypeptide comprising a RNA-binding domain comprises a full-length PUF protein.

In some embodiments of any of the aspects, the RNA-binding domain (e.g., the candidate RNA-binding domain) comprises one or more RNA-binding domains of Argonaute. As used herein "a RNA-binding domain of Argonaute" refers to the PAZ (piwi/argonaute-1/zwille) domain, i.e., a beta-barrel capped on one end by alpha-helices and the other end with a combination of beta-hairpin and alpha-helix. The PAZ domain binds a RNA sequence on the face of the beta-barrel. Natural PAZ domains bind to small non-coding RNAs. The structure, sequence, and function of numerous PAZ domains and their binding specificities are known in the art, including libraries of PAZ domains and engineered PAZ domains with desired specificities. Individual sequences and alignments of exemplary PAZ domains are available in the NCBI database under NCBI ID Nos. 444818, 426635, 198017, 239207, 375776, 436399, and 31988 (e.g., Accession Nos. cl00301, pfam02170, smart00949, cd02825, pfam18349, pfam18309, and pfam12212). For more discussion see, e.g., Yan et al. Nature 2003 426:468-74; Miyoshi et al. Nature Communications 2016 7:11846; Song et al. Nat Struct Biol 2003 10:1026-32; Muller et al. Frontiers in Cell and Developmental Biology 2020; and Wu et al. J Adv Res. 2020 24:317-324; each of which is incorporated by reference herein in its entirety.

In some embodiments of any of the aspects, a RNA-binding domain comprises a PAZ domain. In some embodiments of any of the aspects, a RNA-binding domain consists of a PAZ domain. In some embodiments of any of the aspects, a RNA-binding domain consists essentially of a PAZ domain. In some embodiments of any of the aspects, a polypeptide comprising a RNA-binding domain comprises an Argonaute protein. In some embodiments of any of the aspects, a polypeptide comprising a RNA-binding domain comprises a full-length Argonaute protein.

A non-limiting, exemplary PAZ domain sequence is SEQ ID NO: 12.

SEQ ID NO: 12
QNKEHFQDECTKLLVGNIVITRYNMNRTYRIDDVDWNKTPKDSFTMSDGKEI

TFLEYYSKNYGITVKEEDQPLLIHRPSERQDNHGMLLKGEILLLPELSFMT

GIPEKMKKDFRAMKDLAQQINLS

In some embodiments of any of the aspects, the PAZ domain and/or Argonaute protein is a variant that does not recruit downstream effector proteins. The variants/mutations necessary to avoid recruitment of downstream effector proteins are known in the art. In some embodiments of any of the aspects, the PAZ domain and/or Argonaute protein variant that does not recruit downstream effector proteins does not comprise a PIWI domain. In some embodiments of any of the aspects, the PAZ domain and/or Argonaute protein variant that does not recruit downstream effector proteins comprises a mutation of P590, F587, F659, F587, V5941, A620, F653, L650, I651, Y654, L694, and/or Y698. Further discussion of such variants can be found in, e.g., Schirle et al. Science 2012 336:1037-40 (PMID 22539551); which is incorporated by reference herein in its entirety.

In some embodiments of any of the aspects, the RNA-binding domain (e.g., the candidate RNA-binding domain) comprises one or more RNA-binding domains of lambda N. As used herein, "a RNA-binding domain of lambda N" refers to the RNA-binding domain of the lambda bacteriophage antiterminator protein N, which is also known as lambdaN-(1-22), lambda N22 peptide, or lambdaN peptide, i.e., RNA-binding domains of lambda N are known to bind a nucleotide sequence, usually 19 nt in length, referred to as the "boxB" sequence. The RNA-binding domain of lambda N comprises an arginine-rich motif (ARM) forming a bent alpha helix that binds a GNRA fold in the target boxB nucleotide sequence. The structure, sequence, and function of numerous RNA-binding domains of lambda N and their binding specificities are known in the art, including engineered RNA-binding domains of lambda N with desired specificities. Individual sequences and alignments of exemplary RNA-binding domains of lambda N are available in the NCBI database under NCBI ID No. 288317 (e.g., Accession Nos. pfam11438 and cl12963). For more discussion see, e.g., Horiya et al. Mol Microbiol 2009 74:85-97; Legault et al. Cell 1998 93:289-99; Cocozaki et al. Journal of Bacteriology 190:12; each of which is incorporated by reference herein in its entirety.

In some embodiments of any of the aspects, a RNA-binding domain comprises a RNA-binding domain of lambda N. In some embodiments of any of the aspects, a RNA-binding domain consists of a RNA-binding domain of lambda N. In some embodiments of any of the aspects, a RNA-binding domain consists essentially of a RNA-binding domain of lambda N. In some embodiments of any of the aspects, a polypeptide comprising a RNA-binding domain comprises a lambda N protein. In some embodiments of any of the aspects, a polypeptide comprising a RNA-binding domain comprises a full-length lambda N protein.

A non-limiting, exemplary RNA-binding domain of lambda N sequence is SEQ ID NO: 13.

SEQ ID NO: 13
DAQTRRRERRAEKQAQWKAANPLLVGVSAKPVNRP

In some embodiments of any of the aspects, the RNA-binding domain (e.g., the candidate RNA-binding domain) comprises one or more ribosomal proteins and/or domains of a ribosomal protein. In some embodiments of any of the aspects, the catalytic domain of an RNA-editing enzyme comprises one or more ribosomal proteins and/or domains of a ribosomal protein. It is contemplated herein that embodiments comprising a ribosomal protein permit the study or analysis of translation. Besides fusing ribosomal proteins to RNA-editing enzymes such as ADAR, translation factors or termination factors to can be coupled to RNA-binding domains to measure the same function.

As used herein, "a ribosomal protein" refers to a protein or peptide found in a ribosome. Ribosomes bind RNAs in multiple sites and ways, including the A site, P site, and E sites of the small subunit, as well as homeodomain-like α-helical proteins (L11), OB fold proteins (S1 and S17) and RNP consensus proteins (S6). The structure, sequence, and function of numerous ribosomal proteins and their binding specificities are known in the art, including engineered ribosomal proteins with desired specificities. Individual sequences and alignments of exemplary RNA-binding domains of ribosomal proteins are available in the NCBI database under NCBI ID No. 444693 (e.g., Accession No. cl00098). For more discussion see, e.g., Draper et al. Nuc Acids Res 1999 27:381-8; and Sonenberg 1993 3:317-323; each of which is incorporated by reference herein in its entirety.

In some embodiments of any of the aspects, the RNA-binding domain (e.g., the candidate RNA-binding domain) comprises one or more YTH domains. As used herein, "a YTH domain" refers to a YT521-B homology domain, which forms a globular fold with four-stranded beta sheets and four alpha helices. YTH domains bind RNAs comprising a m6A methylation. The structure, sequence, and function of numerous YTH and their binding specificities are known in the art, including engineered YTH domains with desired specificities. Individual sequences and alignments of exemplary YTH domains are available in the NCBI database under NCBI ID No. 410979 and 427744 (e.g., Accession Nos. cd21134 and pfam04146). For more discussion see, e.g., Zhu et al. Cell Research 2014 24:1493-1496; Li et al. J Chem Inf Model 2020 60:5932-5; and Xu et al. Front Oncol 2021 11:629560; each of which is incorporated by reference herein in its entirety.

In some embodiments of any of the aspects, a RNA-binding domain comprises a YTH domain. In some embodiments of any of the aspects, a RNA-binding domain consists of a YTH domain. In some embodiments of any of the aspects, a RNA-binding domain consists essentially of a YTH domain.

A non-limiting, exemplary YTH domain sequence is SEQ ID NO: 14.

```
                                          SEQ ID NO: 14
RVFIIKSYSEDDIHRSIKYSIWCSTEHGNKRLDSAFRCMSSKGPVYLLFSV

NGSGHFCGVAEMKSPVDYGTSAGVWSQDKWKGKFDVQWIFVKDVPNNQLRH

IRLENNDNKPVTNSRDTQEVPLEKAKQVLKII
```

In some embodiments of any of the aspects, the RNA-binding domain (e.g., the candidate RNA-binding domain) comprises one or more recognition lobe domains (REC) of a CAS. As used herein, "Cas" or "CRISPR Associated Protein" refers to a protein or family of proteins comprise a helicase and nuclease motif and which bind RNAs, including mRNAs, crRNAs, tracrRNA, guide RNAs, and sgRNAs. When bound to crRNA, tracrRNA, and/or sgRNA, Cas are targeted to a target DNA or target RNA with a complementary sequence and cleave the target molecule. The binding of a Cas to the mRNA, crRNA, tracrRNA, guide RNA, and/or sgRNA is mediated by the REC domain. A number of Cas are known, including Cas9, Cas12a, Cascade, and Cas13. Cas bind to a CRISPR sequence having a AT-rich leader sequence followed by short repeats separated by unique spacers. The CRISPR sequences often have hairpin structure. The structure, sequence, and function of numerous Cas and their cognate binding sites (CRISPR) are known in the art, including engineered Cas with desired activities. Individual sequences and alignments of exemplary REC domains are available in the NCBI database under NCBI ID No. 452778, 435447, and 408294 (e.g., Accession Nos. cl27783, pfam16592, and pfam 18501). For more discussion see, e.g., Pickar-Oliver et al. Nature Reviews Molecular Cell Biology 2019 20:490-507; Anzalone et al. Nature Biotechnology 2020 38:824-844; Nidhi et al. Int J Mol Scie 2021 22:3327; Abudayeh et al. Science 2019 365:382-6 (PMID 31296651); Cox et al. Science 2017 365:1019-1027 (PMID 29070703); and Schindele et al. FEBS Letters 2018 592: 1954-67; each of which is incorporated by reference herein in its entirety. Embodiments in which the RNA-binding domain comprises a REC domain of Cas can be used to optimize guideRNAs and/or sgRNAs for use with the Cas itself in gene editing. For example, it is contemplated herein that cells can be transfected with a Cas13 fused to the catalytic domain of the editing enzyme ADAR, together with a recorder mRNA that has a target site for ADAR and a library of guide RNAs (as candidate cognate binding sites) with different structures and sequences but with conserved complementarity to the target site. This approach will identify guide RNAs with novel structures or sequences that optimize Cas13 binding and targeting.

In some embodiments of any of the aspects, a RNA-binding domain comprises a REC domain. In some embodiments of any of the aspects, a RNA-binding domain consists of a REC domain. In some embodiments of any of the aspects, a RNA-binding domain consists essentially of a REC domain. In some embodiments of any of the aspects, a RNA-binding domain comprises a REC domain of Cas13. In some embodiments of any of the aspects, a RNA-binding domain consists of a REC domain of Cas13. In some embodiments of any of the aspects, a RNA-binding domain consists essentially of a REC domain of Cas13. In some embodiments of any of the aspects, a polypeptide comprising a RNA-binding domain comprises an Cas protein. In some embodiments of any of the aspects, a polypeptide comprising a RNA-binding domain comprises a full-length Cas protein. In some embodiments of any of the aspects, a polypeptide comprising a RNA-binding domain comprises an Cas13 protein. In some embodiments of any of the aspects, a polypeptide comprising a RNA-binding domain comprises a full-length Cas13 protein.

A non-limiting, exemplary REC lobe or domain sequence is SEQ ID NO: 15.

```
                                          SEQ ID NO: 15
IEMLHQSMVNILNINLKNVEIEKIEKILKSTQYSNSERLENLLELYELSKN

KNKIETEIFKFICGLKGTISKIYVEDKFEDEFAKMTLSFRDSNFDEKIIEI

EDNLDDDKYDMFLLIKQIHDWSVLANIMNGEEYLSVARVKLYDKHKKDLEV

LKKYYKQNSMEEYNKMFRQMNDGNYSAYVGSVIYKDNSVRRGCKSKKEDFY

KNILNTIKSWEDCEAKEYITSEIDKGNFLPKQITASNGVIPNQVHKKELKK

ILKNASEYLNFLNEKDESGYTISEKIVKLFEFQIPYYVGPIAYNIGNDESK

HRHNMWSVRKEKGPIYPWNFEQKIDIKKSSEKFIRNLINHCTYLNDEEVLP

KNSLLYEKFMVLNELNKLKINGEKISVELKQNIFNDLFKKGKKVTKKGLIK

YLKEQGEIDNCEEVEISGIDGDFTNKLSNYKKFADIFGVQSLTYEQTDIAE

NIIRYSTIYGDSRKFLEERIREEYSNVLDEKQIKRILGMKFKDWGRLSKEL

LELSGVDKETGEIASVISRMWNDNYNLMELIATERFSYAYEIEQ
```

In some embodiments of any of the aspects, the RNA-binding domain (e.g., the candidate RNA-binding domain) comprises one or more Embryonic Lethal Abnormal Vision (ELAV) RNA recognition motifs (RRM). The ELAV or ELAV-like (ELAVL) family of proteins are RNA-binding proteins that have several RRMs and bind to mRNAs. A number of ELAVLs are known, including ELAVL1 (HuR) (NCBI Gene ID: 1994). AU-rich elements (AREs) are distinct sequence elements in the 3'-untranslated region (UTR) of mRNAs often consisting of one or several AUUUA pentamers located in an adenosine and uridine rich region. The structure, sequence, and function of numerous ELAVLs and their cognate binding sites (AU-ruch elements (AREs)) are known in the art. Individual sequences and alignments of exemplary ELAV RRMs are available in the NCBI database under NCBI ID No. 1994 or UniProt Q15717. For more discussion see, e.g., Wang et al. Acta Crystallogr. D 69:373-380 (2013), Meisner et al. (2010). Properties of the Regulatory RNA-Binding Protein HuR and its Role in Controlling miRNA Repression. In: Großhans, H. (eds) Regulation of microRNAs. Advances in Experimental Medicine and Biology, vol 700. Springer, New York, NY; Borgonetti et al. Int. J. Mol. Sci. 2021, 22, 10394; Siang et al. Nat Commun 11, 213 (2020), and Gruber et al. Nucleic Acids Res. 2011 January; 39(Database issue): D66-D69, each of which is incorporated by reference herein in its entirety.

In some embodiments of any of the aspects, a RNA-binding domain comprises a ELAV RRM domain. In some embodiments of any of the aspects, a RNA-binding domain consists of a ELAV RRM domain. In some embodiments of any of the aspects, a RNA-binding domain consists essentially of a ELAV RRM domain. In some embodiments of any of the aspects, a RNA-binding domain comprises a ELAV RRM domain of ELAVL1. In some embodiments of any of the aspects, a RNA-binding domain consists of a ELAV RRM domain of ELAVL1. In some embodiments of any of the aspects, a RNA-binding domain consists essentially of a ELAV RRM domain of ELAVL1. In some embodiments of any of the aspects, a polypeptide comprising a RNA-binding domain comprises an ELAV protein. In some embodiments of any of the aspects, a polypeptide comprising a RNA-binding domain comprises a full-length ELAV protein. In some embodiments of any of the aspects, a polypeptide comprising a RNA-binding domain comprises an ELAVL1 protein. In some embodiments of any of the aspects, a polypeptide comprising a RNA-binding domain comprises a full-length ELAVL1 protein.

Non-limiting, exemplary ELAV RRMs include the 3 RRMs of ELAVL1:

```
                                              SEQ ID NO: 21
TNLIVNYLPQNMTQDELRSLFSSIGEVESAKLIRDKVAGHSLGYGFVNYVT

AKDAERAINTLNGLRLQSKTIKVSYARP

SEQ ID NO: 22
ANLYISGLPRTMTQKDVEDMFSRFGRIINSRVLVDQTTGLSRGVAFIRFDK

RSEAEEAITSFNGHKPPGSSEPITVKFAAN

SEQ ID NO: 23
WCIFIYNLGQDADEGILWQMFGPFGAVTNVKVIRDFNTNKCKGFGFVTMTN

YEEAAMAIASLNGYRLGDKILQVSFKTN
```

In some embodiments of any of the aspects, a cognate binding site for an RNA-binding domain comprising one or more ELAV RRMs comprises one or more AUUUA pentamers located in an adenosine and uridine rich region. In some embodiments of any of the aspects, a cognate binding site for an RNA-binding domain comprising one or more ELAV RRMs consists of one or more AUUUA pentamers located in an adenosine and uridine rich region.

Where reference is made to database entries, e.g., NCBI database entries, reference is made to the information and sequences available as of Nov. 29, 2022 under the indicated ID and/or Accession Number.

As used herein, a "cognate binding site" for an RNA-binding domain refers to an RNA sequence or structure which is bound by a particular RNA-binding domain. As described herein, some RNA-binding domains are highly sequence specific (e.g., zinc fingers), while others recognize RNA structures such as hairpins. The cognate binding sites for given RNA-binding domains are known in the art, see e.g., the examples below as well as Stefl et al. EMBO Reports 2005 6 (1): 33-8 and the EuRBPDB; which are incorporated by reference herein in their entireties.

As noted above, the sequences, structures, and/or modifications that render a RNA a cognate binding site of a particular RNA-binding domain are known in the art. Exemplary pairs of RNA-binding domains and cognate binding sites include but are not limited to: a RNA-binding domain of lambda N and a viral hairpin B-Box; one or more PUF domains and a corresponding series of nucleotides; one or more RNA-binding domains of Argonaute and a reverse complement sequence of the small non-coding RNA bound by the RNA-binding domain of Argonaute; one or more REC domains of Cas and a CRISPR sequence, guideRNA, or sgRNA; one or more ELAV RRMs and an AU-rich element (ARE); or one or more YTH domains and a m6A methylation site. In some embodiments of any of the aspects, the candidate RNA-binding domain comprises a RNA-binding domain of Argonaute, the candidate cognate binding site comprises a reverse complement sequence of the small non-coding RNA bound by the RNA-binding domain of Argonaute, and the combination further comprises the small non-coding RNA.

As used herein, "candidate" refers to an element, e.g., a RNA-binding domain or cognate binding site, that are to be screened and/or analyzed for the strength of their interaction with one or more other elements. A "candidate" element can be known to have the relevant activity or structure, but be a candidate in the sense of being a candidate for binding of a particular level of avidity or specificity, a candidate for binding in particular physical conditions, or a candidate for binding as compared to or in direct competition with other candidates. Where a "candidate" element is referred to herein, the reference includes known elements of that category. For example, where "candidate RNA-binding domain" is used herein, it encompasses the known RNA-binding domains described herein. For the methods described herein, candidates may be screened individually, or in groups. Group screening is particularly useful where hit rates for effective candidates are expected to be low such that one would not expect more than one positive result for a given group.

As used herein, a "catalytic domain of an RNA-editing enzyme" refers to a domain that can make changes (i.e., edits) to an RNA sequence once the RNA exists. RNA editing can include insertion, deletion, or base substitution, but typically does not include RNA processing activities such as splicing, or polyadenylation. In some embodiments, RNA editing comprises cytidine to uridine deamination and adenosine to inosine deamination. RNA-editing enzymes are known in the art and include pentatricopeptide repeat (PPR) proteins, ADAR, APOBEC, and Abe7.10. The structures, sequences, and targets of RNA-editing enzymes are known in the art. For further discussion, see, e.g., Shikanai et al. Biochimica et Biophysica Acta (BBA)—Bioenergetics. SI: Chloroplast Biogenesis. 2015 1847 (9): 779-85; Lerner et al. Genes (Basel) 2019 10:13; Vogel et al. Current Opinion in Biotechnology 2018 55:74-80; Heraud-Farlow et al. Open Biology 2020 10:200085; each of which is incorporated by reference herein in its entirety.

In some embodiments of any of the aspects, a polypeptide comprising the catalytic domain of an RNA-editing enzyme comprises a sequence of the full-length RNA-editing enzyme. In some embodiments of any of the aspects, a polypeptide comprising the catalytic domain of an RNA-editing enzyme comprises a sequence consisting or consisting essentially of the catalytic domain.

In some embodiments of any of the aspects, the RNA-editing enzyme is ADAR. As used herein, "ADAR" or "adenosine deaminase RNA specific" refers to a protein or family of proteins that catalyzes adenosine to inosine deamination. Mammals have three ADARS; ADAR1, ADAR2, and ADAR3. A fourth vertebrate ADAR, TENR, is known. An ADAR has one or more N-terminal dsRNA binding domains and a C-terminal catalytic domain (e.g. a catalytic deaminase domain). These structures are known in the art. For further discussion see, e.g., Savva et al. Genome Biology 2012 13:252 (PMID: 23273215); Jin et al. IUBMB Life 2009 61:572-8 (PMID: 19472181); Duan et al. Wiley Interdiscip Rev RNA 2022 13:e1666 (PMID: 33998151); Keegan et al. Genome Biol 2004 5:209; and Iyer et al. Nucleic Acids Res 2011 39:9473-97; each of which is incorporated by reference herein in its entirety. The structure, sequence, and function of numerous ADARs are known in the art. Individual sequences and alignments of exemplary ADAR catalytic domains are available in the NCBI database under NCBI ID Nos. 445877 and 426616 (e.g., Accession Nos. cl02661; pfam02137; and smart00552).

In some embodiments of any of the aspects, the ADAR is a human ADAR. In some embodiments of any of the aspects, the ADAR is a mammalian ADAR. In some embodiments of any of the aspects, the ADAR is a vertebrate ADAR. In some embodiments of any of the aspects, the ADAR is a *Danio rerio* ADAR. The evolution and homologs of ADAR are well known in the art. For further discussion see, e.g., Savva et al. Genome Biology 2012 13:252 (PMID: 23273215); Jin et al. IUBMB Life 2009 61:572-8 (PMID: 19472181); Duan et al. Wiley Interdiscip Rev RNA 2022 13:e1666 (PMID: 33998151); each of which is incorporated by reference herein in its entirety.

In some embodiments of any of the aspects, the ADAR or the catalytic domain of the ADAR comprises a mutation or variant relative to the wild-type ADAR. Numerous mutations and their effect on the activity and specificity of ADAR are known in the art. For further discussion see, e.g., Kuttan et al. PNAS 2012 109:E3295-304 (PMID: 23129636); and Abudayyeh et al. Science 2019 365:382-6 (PMID 31296651); each of which is incorporated by reference herein in its entirety. Exemplary embodiments include T375G and/or E488Q mutations (relative to, e.g., SEQ ID NO: 26) which maximize activity while minimizing background.

```
NP_001103.1 double-stranded RNA-specific editase 1
isoform 1 [Homo sapiens]
                                       SEQ ID NO: 26
MDIEDEENMSSSSTDVKENRNLDNVSPKDGSTPGPGEGSQLSNGGGGPGR

KRPLEEGSNGHSKYRLKKRRKTPGPVLPKNALMQLNEIKPGLQYTLLSQTG

PVHAPLFVMSVEVNGQVFEGSGPTKKKAKLHAAEKALRSFVQFPNASEAHL

AMGRTLSVNTDFTSDQADFPDTLFNGFETPDKAEPPFYVGSNGDDSFSSSG

DLSLSASPVPASLAQPPLPVLPPFPPPSGKNPVMILNELRPGLKYDFLSES

GESHAKSFVMSVVVDGQFFEGSGRNKKLAKARAAQSALAAIFNLHLDQTPS

RQPIPSEGLQLHLPQVLADAVSRLVLGKFGDLTDNFSSPHARRKVLAGVVM

TTGTDVKDAKVISVSTGTKCINGEYMSDRGLALNDCHAEIISRRSLLRFLY

TQLELYLNNKDDQKRSIFQKSERGGFRLKENVQFHLYISTSPCGDARIFSP

HEPILEEPADRHPNRKARGQLRTKIESGEGTIPVRSNASIQTWDGVLQGER

LLTMSCSDKIARWNVVGIQGSLLSIFVEPIYFSSIILGSLYHGDHLSRAMY

QRISNIEDLPPLYTLNKPLLSGISNAEARQPGKAPNFSVNWTVGDSAIEVI

NATTGKDELGRASRLCKHALYCRWMRVHGKVPSHLLRSKITKPNVYHESKL

AAKEYQAAKARLFTAFIKAGLGAWVEKPTEQDQFSLTP
```

A non-limiting, exemplary ADAR catalytic domain sequence is SEQ ID NO: 16.

```
                                       SEQ ID NO: 16
SVSTGTKCINGEYMSDRGLALNDCHAEIISRRSLLRFLYTQLELYLNNKDD

QKRSIFQKSERGGFRLKENVQFHLYISTSPCGDARIFSPHEPILEEPADRH

PNRKARGQLRTKIESGEGTIPVRSNASIQTWDGVLQGERLLTMSCSDKIAR

WNVVGIQGSLLSIFVEPIYFSSIILGSLYHGDHLSRAMYQRISNIEDLPPL

YTLNKPLLSGISNAEARQPGKAPNFSVNWTVGDSAIEVINATTGKDELGRA

SRLCKHALYCRWMRVHGKVPSHLLRSKITKPNVYHESKLAAKEYQAAKARL

FTAFIKAGLGAWVEKP
```

A non-limiting, exemplary ADAR catalytic domain sequence comprising T375G is SEQ ID NO: 27.

```
                                       SEQ ID NO: 27
SVSTGGKCINGEYMSDRGLALNDCHAEIISRRSLLRFLYTQLELYLNNKDD

QKRSIFQKSERGGFRLKENVQFHLYISTSPCGDARIFSPHEPILEEPADRH

PNRKARGQLRTKIESGEGTIPVRSNASIQTWDGVLQGERLLTMSCSDKIAR

WNVVGIQGSLLSIFVEPIYFSSIILGSLYHGDHLSRAMYQRISNIEDLPPL

YTLNKPLLSGISNAEARQPGKAPNFSVNWTVGDSAIEVINATTGKDELGRA

SRLCKHALYCRWMRVHGKVPSHLLRSKITKPNVYHESKLAAKEYQAAKARL

FTAFIKAGLGAWVEKP
```

A non-limiting, exemplary ADAR catalytic domain sequence comprising E488Q is SEQ ID NO: 28.

```
                                       SEQ ID NO: 28
SVSTGTKCINGEYMSDRGLALNDCHAEIISRRSLLRFLYTQLELYLNNKDD

QKRSIFQKSERGGFRLKENVQFHLYISTSPCGDARIFSPHEPILEEPADRH

PNRKARGQLRTKIESGQGTIPVRSNASIQTWDGVLQGERLLTMSCSDKIAR

WNVVGIQGSLLSIFVEPIYFSSIILGSLYHGDHLSRAMYQRISNIEDLPPL

YTLNKPLLSGISNAEARQPGKAPNFSVNWTVGDSAIEVINATTGKDELGRA

SRLCKHALYCRWMRVHGKVPSHLLRSKITKPNVYHESKLAAKEYQAAKARL

FTAFIKAGLGAWVEKP
```

A non-limiting, exemplary ADAR catalytic domain sequence comprising T375G and E488Q is SEQ ID NO: 29.

SEQ ID NO: 29

SVSTGGKCINGEYMSDRGLALNDCHAEIISRRSLLRFLYTQLELYLNNKDD

QKRSIFQKSERGGFRLKENVQFHLYISTSPCGDARIFSPHEPILEEPADRH

PNRKARGQLRTKIESGQGTIPVRSNASIQTWDGVLQGERLLTMSCSDKIAR

WNVVGIQGSLLSIFVEPIYFSSIILGSLYHGDHLSRAMYQRISNIEDLPPL

YTLNKPLLSGISNAEARQPGKAPNFSVNWTVGDSAIEVINATTGKDELGRA

SRLCKHALYCRWMRVHGKVPSHLLRSKITKPNVYHESKLAAKEYQAAKARL

FTAFIKAGLGAWVEKP

In some embodiments of any of the aspects, the RNA-editing enzyme is ABOPEC. As used herein, "ABOPEC" or "apolipoprotein B mRNA editing enzyme, catalytic polypeptide" refers to a protein or family of proteins that catalyzes cytidine to uridine deamination. Mammals have multiple ABOPECs, including APOBEC1; APOBEC2; APOBEC3A; APOBEC3B; APOBEC3C; APOBEC3D; APOBEC3F; APOBEC3G; APOBEC3H; APOBEC4; and AID. An APOBEC has an N-terminal catalytic domain (e.g. a catalytic deaminase domain) and a C-terminal pseudocatalytic domain. These structures are known in the art. For further discussion see, e.g., Knisbacher et al. Trends Genetics 2016 32:16-28 (PMID: 26608778); Navaratnam et al. Int. J Hematol 2006 83:195-200 (PMID 16720547); Brannan et al. Nat. Methods 2021 18:507-519 (PMID 33963355); Meyer et al. Nat Methods 2019 16:1275-1280 (PMID 31548708); and Grillo et al. Trends Pharmacol Sci 2022 43:362-377; each of which is incorporated by reference herein in its entirety. The structure, sequence, and function of numerous APOBECs are known in the art. Individual sequences and alignments of exemplary APOBEC catalytic domains are available in the NCBI database under NCBI ID Nos. 429866 and 444801 (e.g., Accession Nos. pfam08210, cl38258, and cl00269).

In some embodiments of any of the aspects, the APOBEC is a human APOBEC. In some embodiments of any of the aspects, the APOBEC is a mammalian APOBEC. In some embodiments of any of the aspects, the APOBEC is a vertebrate APOBEC.

A non-limiting, exemplary APOBEC catalytic domain sequence is SEQ ID NO: 17.

SEQ ID NO: 17

FYFHFKNLRKAYGRNESWLCFTMEVVKHHSPVSWKRGVFRNQVDPETGRHA

ERCFLSWFADDILSPNTNYEVTWYTSWSPCPECAGEVAEFLARHSNVNLTI

KTARLYYFDDTDAAEGLRSLSQEGASVEIMGYKDFKYCWENFVYNDDEPFK

PWDGLDYNFLDLDSKLQE

In some embodiments of any of the aspects, the RNA-editing enzyme is ABE. As used herein, "ABE" or "Adenosine Base Editor" refers to a synthetic protein or family of synthetic proteins that catalyzes catalyzes adenosine to inosine deamination. The development, activity, and structure of ABE, including ABE7.10, is described in Lin et al. Biorxiv 2022.09.06.506853; which is incorporated by reference herein in its entirety.

In some embodiments of any of the aspects, the RNA-editing enzyme is RESCUE. As used herein, "RESCUE" or "RNA Editing for Specific C-to-U Exchange" refers to a synthetic protein or family of synthetic proteins that catalyzes catalyzes cytidine to uridine deamination. The development, activity, and structure of RESCUE is described in Abudayyeh et al. Science 2019 365:382-6 (PMID 31296651); which is incorporated by reference herein in its entirety.

In some embodiments of any of the aspects, the RNA-editing enzyme is APOBEC, ADAR, ABE, or RESCUE. In some embodiments of any of the aspects, the RNA-editing enzyme is APOBEC or ADAR. In some embodiments of any of the aspects, the RNA-editing enzyme is an APOBEC or and ADAR. In some embodiments of any of the aspects, the catalytic domain of an RNA-editing enzyme comprises the catalytic domain of APOBEC, ADAR, ABE, or RESCUE. In some embodiments of any of the aspects, the catalytic domain of an RNA-editing enzyme comprises the catalytic domain of APOBEC or ADAR. In some embodiments of any of the aspects, the catalytic domain of an RNA-editing enzyme comprises the catalytic domain of an APOBEC or an ADAR. In some embodiments of any of the aspects, the polypeptide comprising a catalytic domain of an RNA-editing enzyme comprises a full-length APOBEC, ADAR, ABE, or RESCUE. In some embodiments of any of the aspects, the polypeptide comprising a catalytic domain of an RNA-editing enzyme comprises a full-length APOBEC or ADAR.

As used herein, a "cognate substrate site" for the catalytic domain of an RNA-editing enzyme refers to an RNA sequence or structure which is edited by a particular catalytic domain of an RNA-editing enzyme. As described herein, some catalytic domains of an RNA-editing enzyme can be at least partially sequence specific (e.g., APOBEC), while others recognize RNA structures such as adenines mismatches embedded in a segment of double-stranded RNA (e.g., ADAR). The cognate substrate sites for given catalytic domains of RNA-editing enzymes are known in the art, see e.g., the examples below.

ADAR is known to bind to double-stranded RNA structures, catalyzing the deamination of adenosine to inosine. Accordingly, in some embodiments of any of the aspects, a cognate substrate site for a catalytic domain of ADAR comprises a hairpin structure. In some embodiments of any of the aspects, a cognate substrate site for a catalytic domain of ADAR comprises a hairpin structure comprising one or more adenosine nucleotides. In some embodiments of any of the aspects, a cognate substrate site for a catalytic domain of ADAR comprises a hairpin structure comprising one or more adenosine nucleotides mismatched with a cytosine or guanosine nucleotide. The structure and sequence of ADAR cognate substrate sites are further discussed in, e.g., Rodrigues et al. Nature Biotechnology 2021 39:320-5 (PMID 33077959); and Kuttan et al. PNAS 2012 109:E3295-3304; each of which are incorporated by reference herein in their entireties.

APOBEC is known to bind to a TC or CC motif, catalyzing the deamination of cytidine to uridine deamination. Many APOBECs require at least a 5-mer target nucleotide. Many APOBECs bind to their target dimer when the nucleic acid can assume a U-shaped conformation at the dimer. Accordingly, in some embodiments of any of the aspects, a cognate substrate site for a catalytic domain of APOBEC comprises a cytosine nucleotide. In some embodiments of any of the aspects, a cognate substrate site for a catalytic domain of APOBEC comprises a TC or CC dimer motif. The structure and sequence of APOBEC cognate substrate sites are further discussed in, e.g., Knisbacher et al. Trends Genetics 2016 32:16-28 (PMID 26608778); Grillo et al. Trends Pharmacol Sci 2022 43:362-377 (PMID 35272863); Cervantes-Gracia et al. Trends Genet 2021 37:1028-43

(PMID 34353635); and Shi et al. Nature Structural & Molecular Biology 2016 24:131-9; each of which are incorporated by reference herein in their entireties.

In some embodiments of any of the aspects, a reporter gene comprises the cognate substrate site and an editing event will turn the reporter activity on or off, e.g., editing will introduce or remove a stop codon or an enzymatically active amino acid. In such embodiments, the detecting can comprise detection of the reporter gene activity, e.g., by any of the methods described herein.

In some embodiments of any of the aspects, a regulatory element of a reporter gene comprises the cognate substrate site and an editing event will turn the reporter activity on or off, e.g., editing will introduce or remove a ribosome binding site sequence. In such embodiments, the detecting can comprise detection of the reporter gene activity, e.g., by any of the methods described herein.

In some embodiments of any of the aspects, a single polypeptide (e.g., a single polypeptide strand or molecule) comprises the candidate RNA-binding domain and the catalytic domain of a RNA-editing enzyme. In some embodiments of any of the aspects, a pair of polypeptides comprises the candidate RNA-binding domain and the catalytic domain of a RNA-editing enzyme, and the pair of polypeptides are conjugated or bound to each other, e.g., via linker or substrate. In some embodiments of any of the aspects, a pair of polypeptides comprises the candidate RNA-binding domain and the catalytic domain of a RNA-editing enzyme, and the pair of polypeptides comprises:
  a) a bait polypeptide comprising: a first candidate interaction domain and the candidate RNA-binding domain; and
  b) a prey polypeptide comprising: a second candidate interaction domain and the catalytic domain of a RNA-editing enzyme.

As used herein, "interaction domain" refers to a domain that permits specific binding of two separate polypeptides to each other. A number of exemplary interaction domains, as well as pairs of interaction domains are provided elsewhere herein. In some embodiments, the interaction domains of the polypeptides can bind specifically, e.g. one of the interaction domains can bind specifically to the other interaction domain. Exemplary interaction domains are known in the art and can be used in embodiments of the aspects described herein. Non-limiting examples of interaction domains include leucine zippers (see further discussion in e.g., in Reinke et al. JACS 2010 132:6025-31 and Thompson et al. ACS Synth Biol 2012 1:118-129; each of which is incorporated by reference herein in its entirety), a streptavidin domain and a streptavidin binding protein (SBP) domain, a chemically-induced pair of interaction domains (see, further discussion in e.g., Miyamoto et al. Nat Chem Biol. 2012 Mar. 25; 8(5): 465-470 and Belshaw et al. PNAS 1996 93:4604-4607; each of which is incorporated herein by reference in its entirety). Interaction domains can also include an antibody, antigen-binding portion of an antibody, or a nanobody, and the cognate antigen. Large numbers of antibodies and their cognate antigens are known in the art and available commercially. For example, see the Antibody Registry, which provides 100s of thousands of antibodies with their cognate antigen identities. In some embodiments of any of the aspects, the first candidate interaction domain and the second candidate interaction domain comprise a nanobody and its cognate antigen (in either order).

In some embodiments of any of the aspects, the interaction domains are candidate interaction domains, e.g., the combinations and methods described herein can be used to screen for specific binding and/or binding strength of candidate interaction domains. In such embodiments, the combinations and methods described herein can be used to screen for new nanobodies or antibodies specific for a given target (e.g., antigen).

In some embodiments of any of the aspects, a polypeptide or pair of polypeptides described herein comprises a single instance or occurrence of the candidate RNA-binding domain, e.g., the polypeptide or pair of polypeptides is monomeric for the candidate RNA-binding domain. In some embodiments of any of the aspects, a polypeptide or pair of polypeptides described herein comprises a plurality of instances or occurrences of the candidate RNA-binding domain, e.g., the polypeptide or pair of polypeptides is polymeric for the candidate RNA-binding domain.

In some embodiments of any of the aspects, a polypeptide or pair of polypeptides described herein comprises a single instance or occurrence of the catalytic domain of an RNA-editing enzyme, e.g., the polypeptide or pair of polypeptides is monomeric for the catalytic domain of an RNA-editing enzyme. In some embodiments of any of the aspects, a polypeptide or pair of polypeptides described herein comprises a plurality of instances or occurrences of the catalytic domain of an RNA-editing enzyme, e.g., the polypeptide or pair of polypeptides is polymeric for the catalytic domain of an RNA-editing enzyme.

In some embodiments of any of the aspects, i) the candidate RNA-binding domain and ii) the catalytic domain of an RNA-editing enzyme are not found in the same naturally-occurring polypeptide. In some embodiments of any of the aspects, i) the candidate RNA-binding domain and ii) the catalytic domain of an RNA-editing enzyme are not found in a single naturally-occurring polypeptide. In some embodiments of any of the aspects, i) the candidate RNA-binding domain and ii) the catalytic domain of an RNA-editing enzyme are not found in the proteome of a single species.

In some embodiments of any of the aspects, a RNA described herein comprises a single instance or occurrence of the candidate cognate binding site, e.g., the RNA is monomeric for the candidate cognate binding site. In some embodiments of any of the aspects, a RNA described herein comprises a plurality of instances or occurrences of the candidate cognate binding site, e.g., the RNA is polymeric for the candidate cognate binding site. In some embodiments of any of the aspects, a RNA described herein comprises a plurality of tandem repeats of the candidate cognate binding site.

In some embodiments of any of the aspects, a RNA described herein comprises a single instance or occurrence of the cognate substrate site, e.g., the RNA is monomeric for the cognate substrate site. In some embodiments of any of the aspects, a RNA described herein comprises a plurality of instances or occurrences of the cognate substrate site, e.g., the RNA is polymeric for the cognate substrate site. In some embodiments of any of the aspects, a RNA described herein comprises a plurality of tandem repeats of the cognate substrate site.

In some embodiments of any of the aspects, the at least one RNA further comprises one or more sequencing adapter sequences. As used herein, a "sequencing adapter sequence" refers to a sequence in a target (transcribed as part of the target or ligated to the target) which can specifically hybridize with a sequencing primer, e.g., a next-generation sequencing primer, to permit amplification of a target. Sequencing adapter sequences for a variety of next-generation sequencing platforms are well known in the art. In some embodiments of any of the aspects, the at least one RNA comprises, from 5' to 3': at least one sequencing adapter sequence; the at least one candidate cognate binding site for the candidate RNA-binding domain and the at least one cognate substrate site for the catalytic domain, in either relative order; and at least one sequence adapter sequence.

Editing activity can also be detected without sequencing, e.g., by the use of reporter genes. For example, two distinguishable (e.g., differently colored fluorescent reporter genes) can be encoded in a mRNA molecule and separated by a domain comprising in any order: the at least one candidate cognate binding site for the candidate RNA-binding domain, and the at least one cognate substrate site for the catalytic domain, wherein the at least one cognate substrate site for the catalytic domain further comprises a stop codon. Editing of the cognate substrate will disrupt the stop codon, permitting transcription of the second reporter gene (e.g., as a polymeric protein). Detection of the second reporter gene's signal is thus indicative of editing activity.

A reporter gene encodes or produces a detectable signal or label. Detectable labels, methods of detecting them are well known in the art.

In some embodiments of any of the aspects, detectable labels can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). Detectable labels can include, but are not limited to radioisotopes, bioluminescent compounds, chromophores, antibodies, chemiluminescent compounds, fluorescent compounds, metal chelates, and enzymes. In some embodiments of any of the aspects, the detectable label or signal is a fluorescent compound, e.g, a fluorescent dye molecule or fluorophore. In some embodiments of any of the aspects, the detectable label or signal is a radiolabel. In some embodiments of any of the aspects, the detectable label or signal is a chemiluminescent compound. In some embodiments of any of the aspects, the detectable label or signal is a enzymatic label, e.g., a enzyme that can produce a chemiluminescent signal, a color signal, or a fluorescent signal. In some embodiments of any of the aspects, a detectable label can be a spectral colorimetric label including, but not limited to colloidal gold or colored glass or plastic (e.g., polystyrene, polypropylene, and latex) beads.

A reporter gene encoding any fluorescent protein can be applicable in the technology described herein. The fluorescent protein includes, but is not limited to, for example, GFP, mCherry, Venus, and Cerulean. Examples of genes encoding fluorescent proteins that can be used in accordance with the compositions and methods described herein include, without limitation, those proteins provided in U.S. Patent Application No. 2012/0003630 (see Table 59), incorporated herein by reference.

Similarly, a reporter gene encoding any enzyme can be applicable as well. Enzymes that produce colored substrates ("colorimetric enzymes") can also be used for visualization and/or quantification. Enzymatic products can be quantified using spectrophotometers or other instruments that can take absorbance measurements including plate readers. Examples of genes encoding colorimetric enzymes that can be used in accordance with the compositions and methods described herein include, without limitation, lacZ alpha fragment, lacZ (encoding beta-galactosidase, full-length), and xylE. An enzyme (e.g., glucose oxidase) can also change the conductivity of a reaction volume, permitting an electrical or electronic readout (Malitesta et al., Anal Chem 1990, 62, 2735-2740). In another example, a nuclease enzyme can cleave a nucleic acid sequence such that an electronic and optical signal is generated. In yet another example, an enzyme can separate a fluorescence resonance energy transfer (FRET) or quenching pair to induce a change in fluorescence.

A reporter gene encoding any antigen for which a specific antibody is available or can be made can also be applicable. By way of example only, as antigens are expressed by the reporter gene, the antigens bind to an electrode coated with complementary antibodies, which produces an electronic signal. Conversely, a reporter gene can encode an antibody, which when expressed, binds to an electrode coated with the complementary antigen. For non-limiting examples of reporter genes, see Reporter Genes: A Practical Guide, D. Anson (Ed.), 2007, Humana Press, the contents of which are incorporated by reference for examples on reporter genes.

A reporter gene encoding luciferases can also be used in the technology described herein. Luciferases produce luminescence, which can be readily quantified using a plate reader or luminescence counter. Examples of genes encoding luciferases for that can be used in accordance with the compositions and methods described herein include, without limitation, Rluc and firefly luciferase (from *Photinus pyralis*).

In some embodiments of any of the aspects, the at least one RNA further comprises a barcode sequence. As used herein, a "barcode" refers to a short sequence of nucleotides (e.g., fewer than 40, 30, 25, 20, 15, 13, 12, or fewer nucleotides) included in a which is unique to a particular RNA described herein, e.g., to a particular candidate cognate binding site, or to a particular pair of candidate cognate binding site and cognate substrate site. In some embodiments of any of the aspects, the barcode sequence is unique or distinguishable from at least one other barcode sequence comprised by other RNAs with a different candidate cognate binding site as described herein. In some embodiments of any of the aspects, the barcode is part of the sequencing adapter sequence, or contiguous with the sequencing adapter sequence.

In some embodiments of any of the aspects, the at least one RNA further comprises a nuclear enrichment sequence. Such embodiments are particularly useful when the RNA-binding protein is one that is localized to or found in the nucleus. As used herein, "nuclear enrichment sequence" refers to a nucleotide sequence that promote the trafficking, accumulation, or retention of a mRNA in the nucleus, such that the concentration or amount of the mRNA in the nucleus is higher than in the absence of the nuclear enrichment sequence. Nuclear enrichment sequences are known in the art. For further discussion, see, e.g., Shukla et al. EMBO J 2018 37:e98452 (PMID; 29335281, which describes more than 100 nuclear enrichment sequences); Tong et al. RNA Biol 2021 18:2073-86 (PMID: 33682620); Lubelsky et al. Nature 2018 555:107-111 (PMID: 29466324); each of which is incorporated herein by reference in its entirety).

In some embodiments of any of the aspects, the at least one RNA further comprises a 3' sequence. In some embodiments of any of the aspects, the at least one RNA further comprises a polyA sequence. PolyA sequences or tails are well known in the art. The 3' sequences can reduce or inhibit mRNA degradation, permitting more robust systems or assays, and/or counteracting degradation induced by the binding of a RNA-binding protein. Exemplary 3' sequences include:

```
                                          SEQ ID NO: 1
aaaaaaaaaaaaaaaaaaaaaaaaaaaaaaaaaaaaaaaaaaaaaaaaaaaa aaaaaatgcatctggtttcctggtctgtctcctctcggtttaagGCGGCCG
c SEQ ID NO: 2
axtgcatctggtttcctggtctgtctcctctcggtttaagGCGGCCGC;
wherein x is an integer from 1 to 100.

SEQ ID NO: 24
axny;
wherein x is an integer from 1 to 100, y is an
integer from 1 to 100 and each n is independently
any nucleotide.

SEQ ID NO: 25
axny;
wherein x is 60, y is 40 and each n is
independently any nucleotide.
```

In some embodiments of any of the aspects, the i) at least one candidate cognate binding site for the candidate RNA-binding domain and ii) at least one cognate substrate site for the catalytic domain are not found in the same naturally-occurring RNA. In some embodiments of any of the aspects, the i) at least one candidate cognate binding site for the candidate RNA-binding domain and ii) at least one cognate substrate site for the catalytic domain are not found in a single naturally-occurring RNA. In some embodiments of any of the aspects, the i) at least one candidate cognate binding site for the candidate RNA-binding domain and ii) at least one cognate substrate site for the catalytic domain are not found in the genome or transcriptome of a single species.

In some embodiments of the aspects, e.g., when the combination is intended for use in screening to identify or quantify interaction strength of a specific cognate binding site with a plurality of candidate RNA-binding domains, the combination comprises a plurality of polypeptides or pair of polypeptides collectively comprising a plurality of candidate RNA-binding domains, e.g., a plurality of different candidate RNA-binding domains.

Each of the plurality of polypeptides or pairs of polypeptides can comprise one or more different candidate RNA-binding domains. In some embodiments of any of the aspects, each polypeptide or pair of polypeptides of the plurality of polypeptides or pair of polypeptides comprises a single candidate RNA-binding domain. In some embodiments of any of the aspects, each polypeptide or pair of polypeptides of the plurality of polypeptides or pair of polypeptides comprises two or more different RNA-binding domains. In some embodiments of any of the aspects, the plurality of polypeptides or pair of polypeptides comprises at least 2 different RNA-binding domains. In some embodiments of any of the aspects, the plurality of polypeptides or pair of polypeptides comprises at least 3 different RNA-binding domains. In some embodiments of any of the aspects, the plurality of polypeptides or pair of polypeptides comprises at least 10 different RNA-binding domains. In some embodiments of any of the aspects, the plurality of polypeptides or pair of polypeptides comprises at least 20 different RNA-binding domains. In some embodiments of any of the aspects, the plurality of polypeptides or pair of polypeptides comprises at least 50 different RNA-binding domains. In some embodiments of any of the aspects, the plurality of polypeptides or pair of polypeptides comprises at least 100 different RNA-binding domains. In some embodiments of any of the aspects, the combination comprises a plurality of polypeptides or pair of polypeptides collectively comprising a plurality of candidate RNA-binding domains; and one RNA comprising a cognate binding site. In some embodiments of any of the aspects, the combination comprises a plurality of polypeptides or pair of polypeptides collectively comprising a plurality of different candidate RNA-binding domains; and one RNA comprising a cognate binding site.

In some embodiments of the aspects, e.g., when the combination is intended for use in screening to identify or quantify interaction strength of a specific RNA-binding domain with multiple cognate binding sites, the combination comprises a plurality of RNAs collectively comprising a plurality of candidate cognate binding sites, e.g., a plurality of different candidate cognate binding sites. Each of the plurality of RNAs can comprise one or more different candidate cognate binding sites. In some embodiments of any of the aspects, each RNA of the plurality of RNAs comprises a single candidate cognate binding site. In some embodiments of any of the aspects, each RNA of the plurality of RNAs comprises two or more different candidate cognate binding sites. In some embodiments of any of the aspects, the plurality of RNAs comprises at least 2 different candidate cognate binding sites. In some embodiments of any of the aspects, the plurality of RNAs comprises at least 3 different candidate cognate binding sites. In some embodiments of any of the aspects, the plurality of RNAs comprises at least 10 different candidate cognate binding sites. In some embodiments of any of the aspects, the plurality of RNAs comprises at least 20 different candidate cognate binding sites. In some embodiments of any of the aspects, the plurality of RNAs comprises at least 50 different candidate cognate binding sites. In some embodiments of any of the aspects, the plurality of RNAs comprises at least 100 different candidate cognate binding sites. In some embodiments of any of the aspects, the combination comprises one polypeptide or pair of polypeptides comprising a RNA-binding domain; and a plurality of RNAs collectively comprising a plurality of candidate cognate binding sites. In some embodiments of any of the aspects, the combination comprises one polypeptide or pair of polypeptides comprising a RNA-binding domain; and a plurality of RNAs collectively comprising a plurality of different candidate cognate binding sites.

In one aspect of any of the embodiments, described herein is a cell comprising or expressing the combination described herein. In one aspect of any of the embodiments, described herein is a cell comprising one or more nucleic acids encoding the combination described herein. In one aspect of any of the embodiments, described herein is a plurality of cells comprising or expressing the combination described herein, wherein each cell of the plurality comprises a different combination, e.g., combinations comprising different RNA-binding domains or different cognate binding sites. In one aspect of any of the embodiments, described herein is an organism comprising at least one cell comprising or expressing the combination described herein.

In some embodiments of any of the aspects, an element (e.g., a polypeptide or nucleic acid element) described herein is an element from, having a sequence naturally found in, or obtained from a virus, bacteria, plant, or animal. In some embodiments of any of the aspects, an element (e.g., a polypeptide or nucleic acid element) described herein is an element from, having a sequence naturally found in, or obtained from a vertebrate. In some embodiments of any of the aspects, an element (e.g., a polypeptide or nucleic acid element) described herein is an element from, having a sequence naturally found in, or obtained from a mammal. In some embodiments of any of the aspects, an element (e.g., a polypeptide or nucleic acid element) described herein is an element from, having a sequence naturally found in, or obtained from a primate. In some embodiments of any of the aspects, an element (e.g., a polypeptide or nucleic acid element) described herein is an element from, having a sequence naturally found in, or obtained from a human. In some embodiments of any of the aspects, an element (e.g., a polypeptide or nucleic acid element) described herein is an element from, having a sequence naturally found in, or obtained from *Danio rerio*. In some embodiments of any of the aspects, an element (e.g., a polypeptide or nucleic acid element) described herein is an element from, having a sequence naturally found in, or obtained from a yeast. In some embodiments of any of the aspects, an element (e.g., a polypeptide or nucleic acid element) described herein is an element from, having a sequence naturally found in, or obtained from *Saccharomyces cerevisiae*.

It is contemplated herein that interaction of a candidate RNA-binding domain and a candidate cognate binding site can be detected not only by the activity of the RNA editing enzyme, but also via the use of a reporter gene in the RNA. Accordingly, in some embodiments of any of the aspects, the candidate RNA-binding domain comprises a ribosomal protein and the at least one RNA further comprises a sequence encoding a reporter gene. As used herein, the term "reporter gene" refers to a nucleic acid that encodes a reporter molecule that can be detected by spectroscopic, photochemical, biochemical, immunochemical, electromagnetic, radiochemical, or chemical means, such as fluorescence, chemifluorescence, chemiluminescence, or bioluminescence or any other appropriate means. Reporter molecules generally produce a measurable signal such as fluorescence, color, or luminescence. Exemplary reporter molecules include, but are not limited to bioluminescent compounds, chromophores, antibodies, chemiluminescent compounds, fluorescent compounds, metal chelates, and enzymes. The reporter molecule can be a protein whose presence can be readily observed. For example, fluorescent proteins fluoresce when excited with light of a particular wavelength, luciferases catalyze a reaction that produces light, and enzymes such as β-galactosidase convert a substrate to a colored product.

In some embodiments, the reporter molecule is a fluorescent protein. In other words, the reporter gene encodes a fluorescent protein. Non-limiting examples of fluorescent proteins include: a UV fluorescent protein, a blue fluorescent protein (BFP), a cyan fluorescent protein (CFP), green fluorescent protein (GFP), a yellow fluorescent protein (YFP), an orange fluorescent protein (OFP), a red fluorescent protein (RFP), a far-red fluorescent protein, a near IR fluorescent protein, a Sapphire-type fluorescent protein, or a Long Stokes shift fluorescent protein. Typically, the indicated color of the fluorescent protein is set based on its emission wavelength. Additional examples of sequences and genes encoding fluorescent proteins that can be used in accordance with the invention include, without limitation, those proteins provided in U.S. Patent Application No. 2012/0003630 (see Table 59), incorporated herein by reference in its entirety.

Examples of UV fluorescent proteins include, but are not limited to, Sirius, Sandercyanin, and shBFP-N158S/L173I. Examples of blue fluorescent proteins include, but are not limited to, Azurite, EBFP2, mKalama1, mTagBFP2, and tagBFP. Examples of cyan fluorescent proteins include, but are not limited to, ECFP, Cerulean, mCerulean3, SCFP3A, CyPet, mTurquoise, mTurquoise2, TagCFP, Mtfp1, monomeric Midoriishi-Cyan, and Aquamarine. Examples of green fluorescent proteins include, but are not limited to, TurboGFP, TagGFP2, mUKG, Superfolder GFP, Emerald, EGFP, Monomeric Azami Green, mWasabi, Clover, and mNeonGreen. Examples of yellow fluorescent proteins include, but are not limited to, TagYFP, EYFP, Topaz, Venus, SYFP2, Citrine, Ypet, IanRFP-ΔS83, and mPapaya1. Examples of orange fluorescent proteins include, but are not limited to, Monomeric Kusabira-Orange, mOrange, mOrange2, mKOκ, and Mko2. Examples of red fluorescent proteins include, but are not limited to, TagRFP, TagRFP-T, mRuby, mRuby2, mTangerine, mApple, mStrawberry, FusionRed, mCherry, and mNectarine. Examples of far red fluorescent proteins include, but are not limited to, mKate2, HcRed-Tandem, mPlum, mRaspberry, mNeptune, NirFP, TagRFP657, TagRFP675, and mCardinal. Examples of near IR fluorescent proteins include, but are not limited to, iFP1.4, iRFP713 (iRFP), iRFP670, iRFP682, iRFP702, iRFP720, and iFP2.0. Examples of sapphire-type fluorescent proteins include, but are not limited to, Sapphire, T-Sapphire, and mAmetrine. Examples of long Stokes shift fluorescent proteins include, but are not limited to, mKeima Red, mBeRFP, LSS-mKate2, LSS-mKate1, LSSmOrange, CyOFP1, and Sandercyanin.

Luciferases can also be used as reporter molecules, as cells tend to have little to no background luminescence in the absence of a luciferase. Luminescence can be readily quantified using a plate reader or luminescence counter. Examples of genes encoding luciferases that can be used in the systems described herein include, without limitation, dmMyD88-linker-Rluc, dmMyD88-linker-Rluc-linker-PEST191, *Renilla luciferase*, Nanuluciferase (e.g., from the deep sea shrimp *Oplophorus gracilirostris* (see, e.g., Hall et al. ACS Chem Biol 2012 7:1848-1857 (PMID 22894855); which is incorporated by reference herein in its entirety); and firefly luciferase (from *Photinus pyralis*).

Enzymes that produce colored substrates ("colorimetric enzymes") can also be used as reporter molecules. Enzymatic products can be quantified using spectrophotometers or other instruments that can take absorbance measurements including plate readers. Like luciferases, enzymes such as β-galactosidase can be used for measuring low levels of gene expression because they tend to amplify low signals. Examples of genes encoding colorimetric enzymes that can be used in accordance with the systems described herein include, without limitation, lacZ alpha fragment, lacZ (encoding β-galactosidase, full-length), and xylE.

In some embodiments of any of the aspects, a cell described herein is a vertebrate cell. In some embodiments of any of the aspects, a cell described herein is a mammalian cell. In some embodiments of any of the aspects, a cell described herein is a primate cell. In some embodiments of any of the aspects, a cell described herein is a human cell. In some embodiments of any of the aspects, a cell described herein is a *D. rero* cell. In some embodiments of any of the aspects, a cell described herein is a yeast cell. In some embodiments of any of the aspects, a cell described herein is a *S. cerevisiae* cell. In some embodiments of any of the aspects, a cell described herein is a plant cell. In some embodiments of any of the aspects, a cell described herein is a bacterial cell.

As described herein, the combinations of polypeptides and RNAs described herein rely on the interaction of a RNA-binding domain and cognate binding site to associate the polypeptide(s) and the RNA. Once in association, the catalytic domain of an RNA editing enzyme has the opportunity to edit the cognate substrate site. The stronger the interaction of the RNA-binding domain and cognate binding site, the greater the amount of editing that will be performed on the RNA's cognate substrate site. Accordingly, described herein is a method of detecting the strength of the binding of a candidate RNA-binding domain to a candidate cognate binding site, the method comprising:
  a) contacting the at least one polypeptide as described herein with the at least one RNA as described herein for a period of time; and
  b) detecting the amount of editing present in the cognate substrate site; wherein the amount of editing generated during the period of time correlates to the strength of the binding.

In some embodiments of any of the aspects, the strength of interaction can refer to binding affinity. In some embodiments of any of the aspects, the strength of interaction can refer to avidity. In some embodiments of any of the aspects, the strength of interaction can refer to specificity. In some embodiments of any of the aspects, the strength of interaction can refer to $K_d$.

In some embodiments of any of the aspects, the strength of interaction can refer to relative strength, e.g., relative to the strength of interaction in a pool of candidate elements. Accordingly, in some embodiments the methods described herein further comprises performing steps a) and b) for a plurality of different polypeptides and RNAs to determine relative binding strength or editing activity.

In some embodiments of any of the aspects, the period of time is at least 2 hours. In some embodiments of any of the aspects, the period of time is at least 3 hours. In some embodiments of any of the aspects, the period of time is at least 4 hours. In some embodiments of any of the aspects, the period of time is less than 24 hours.

In some embodiments of any of the aspects, the candidate RNA-binding domain and the candidate cognate binding site comprise: one or more RNA-binding domains of lambda N and a viral hairpin B-Box and the period of time is at least 2 hours. In some embodiments of any of the aspects, the candidate RNA-binding domain and the candidate cognate binding site comprise: one or more RNA-binding domains of lambda N and a viral hairpin B-Box and the period of time is at least 3 hours. In some embodiments of any of the aspects, the candidate RNA-binding domain and the candidate cognate binding site comprise: one or more RNA-binding domains of lambda N and a viral hairpin B-Box and the period of time is at least 4 hours. In some embodiments of any of the aspects, the period of time is less than 24 hours.

As described elsewherein herein, several types of RNA editing are known and detecting the amount of editing can comprise detecting one or more forms of editing. The detection can be qualitative or quantitative. Exemplary detection methods include sequencing, fluorescence detection, or reporter gene detection.

Methods of detecting RNA editing are known in the art, e.g., RNA editing events can be detected by mass spectrometry (e.g., NAIL-MS) and sequencing. A number of techniques adapted for detecting RNA editing by sequencing are known and include but are not limited to MeRIP-seq, m6A-seq, PA-m5C-seq, methylation-iCLIP, m6A-CLIP, Pseudo-seq, T-seq, CeU-seq, Aza-IP, and RiboMeth-seq.

In some embodiments of any of the aspects, the detecting comprises sequencing of the RNA. As used herein, "sequencing" refers to the determination of the exact order of nucleotide bases in a strand of DNA (deoxyribonucleic acid) or RNA (ribonucleic acid) or the exact order of amino acids residues or peptides in a protein. Nucleic acid sequencing can be done using Sanger sequencing, dideoxy chain termination, or next-generation high-throughput sequencing.

Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized.

In some embodiments of any of the aspects, the detecting comprises high-throughput sequencing of the RNA. In some embodiments of any of the aspects, the detecting comprises next generation sequencing of the RNA. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore.

As used herein "next-generation sequencing" refers to oligonucleotide sequencing technologies that have the capacity to sequence oligonucleotides at speeds and throughputs above those possible with conventional sequencing methods (e.g. Sanger sequencing), due to performing and reading out thousands to millions of sequencing reactions in parallel. Next-generation sequencing includes third and fourth generation sequencing technologies. Non-limiting examples of next-generation sequencing methods/platforms include bridge amplication (Illumina's MiniSeq, MiSeq, NextSeq, NovaSeq, and HiSeq); Massively Parallel Signature Sequencing (Lynx Therapeutics/Illumina); 454 pyro-sequencing (454 Life Sciences/Roche Diagnostics); solid-phase, reversible dye-terminator sequencing (Solexa/Illumina): SOLiD technology (Applied Biosystems); Ion semiconductor sequencing (ION Torrent); DNA nanoball sequencing (Complete Genomics); small molecule realtime (SMRT (Pacific Biosciences), nanopore-based DNA sequencing (Oxford Nanopore Technologies's MinION, GridION, and PremethION), and technologies available from Intelligen Bio-systems, and Helicos Biosciences. Next-generation sequencing technologies and the constraints and design parameters of associated sequencing primers are well known in the art (see, e.g. Shendure, et al., "Next-generation DNA sequencing," Nature, 2008, vol. 26, No. 10, 1135-1145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11(3):333-43; Zhang et al., "The impact of next-generation sequencing on genomics", J Genet Genomics, 2011, 38(3):95-109; (Nyren, P. et al. Anal Biochem 208: 17175 (1993); Bentley, D. R. Curr Opin Genet Dev 16:545-52 (2006); Strausberg, R. L., et al. Drug Disc Today 13:569-77 (2008); U.S. Pat. Nos. 7,282,337; 7,279,563; 7,226,720; 7,220,549; 7,169,560; 6,818,395; 6,911,345; US Pub. Nos. 2006/0252077; 2007/0070349; and 20070070349; which are incorporated by reference herein in their entireties). Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humana Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

In some embodiments of any of the aspects, a reporter gene comprises the cognate substrate site and an editing event will turn the reporter activity on or off, e.g., editing will introduce or remove a stop codon or an enzymatically active amino acid. In such embodiments, the detecting can comprise detection of the reporter gene activity, e.g., by any of the methods described herein.

In some embodiments of any of the aspects, a regulatory element of a reporter gene comprises the cognate substrate site and an editing event will turn the reporter activity on or off, e.g., editing will introduce or remove a ribosome binding site sequence. In such embodiments, the detecting can comprise detection of the reporter gene activity, e.g., by any of the methods described herein.

In some embodiments of any of the aspects, the catalytic domain is a catalytic domain of ADAR and the amount of editing is the number of A to I edits (or A to G edits if present in a DNA molecule and/or in many sequencing readouts). In some embodiments of any of the aspects, the catalytic domain is a catalytic domain of APOBEC and the amount of editing is the number of C to U edits (or C to T edits if present in a DNA molecule and/or in many sequencing readouts).

As described elsewhere herein, the methods described herein can be used to identify a cognate binding site for a particular RNA-binding domain, and/or to identify candidate RNA-binding domains that bind a particular cognate binding site. Accordingly, in some embodiments the methods described herein further comprises performing steps a) and b) for a plurality of different RNAs. In some embodiments the methods described herein further comprises performing steps a) and b) for a plurality of different polypeptides. The different polypeptides or RNA can comprise entirely different sequences obtained from different original proteins/mRNAs, or they can comprise variants, e.g., in some embodiments of any of the aspects, the plurality of different polypeptides comprise different sequences or modifications in the RNA-binding domain. In some embodiments of any of the aspects, the plurality of different polypeptides comprise different post-translational modifications in the RNA-binding domain. In some embodiments of any of the aspects, the plurality of different RNAs comprise different sequences or modifications in the cognate binding site.

In addition to detecting the strength of interaction of a RNA-binding domain and cognate binding site, the methods described herein can also detect the effect of other agents on the strength of this interaction. Accordingly, in some embodiments, the methods described herein can further comprise contacting the polypeptide and RNA with an test agent, e.g., a drug candidate, a candidate RNA-editing inhibitor, or a candidate RNA-editing agonist, in step a). Alternatively, the methods described herein can comprise performing steps a) and b) for two samples, one in the presence of the test agent and one in the absence of the test agent. Alternatively, the methods described herein can comprise contacting the polypeptide and RNA with an test agent, e.g., a drug candidate, a candidate RNA-editing inhibitor, or a candidate RNA-editing agonist, in step a) and comparing the detected level of activity to a previously detected level of activity of the same polypeptide and RNA in the absence of the test agent. Multiple test agents can be screened simultaneously, e.g., in a high-throughput and/or pooled manner. The contacting step can occur in vitro or in vivo. In some embodiments of any of the aspects, the contacting step occurs in a cell. In some embodiments of any of the aspects, the contacting step occurs in an organism.

Nucleic acid and ribonucleic acid (RNA) molecules can be isolated from a particular biological sample using any of a number of procedures, which are well-known in the art, the particular isolation procedure chosen being appropriate for the particular biological sample. For example, Trizol and chloroform extraction, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)). Suitable lysis preparations and methods for lysis are known in the art and can include those described in Shatzkes et al. Sci Rep 2014 4:4659 (PMID 24722424); Svec et al. Front Oncol 2013 3:274 (PMID 24224157); and Ho et al. PLoS One 2013 8:e72463 (PMID 24039771); each of which is incorporated by reference herein in its entirety.

In one respect, the present invention relates to the herein described compositions, methods, and respective component(s) thereof, as essential to the technology, yet open to the inclusion of unspecified elements, essential or not ("comprising). In some embodiments of any of the aspects, other elements to be included in the description of the composition, method or respective component thereof are limited to those that do not materially affect the basic and novel characteristic(s) of the technology (e.g., the composition, method, or respective component thereof "consists essentially of" the elements described herein). This applies equally to steps within a described method as well as compositions and components therein. In other embodiments of any of the aspects, the compositions, methods, and respective components thereof, described herein are intended to be exclusive of any element not deemed an essential element to the component, composition or method (e.g., the composition, method, or respective component thereof "consists of" the elements described herein). This applies equally to steps within a described method as well as compositions and components therein.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein "combination" refers to a group of two or more substances for use together, e.g., for use in an assay to measure protein-RNA interaction(s). The two or more substances can be present in the same formulation in any molecular or physical arrangement, e.g, in an admixture, in a solution, in a mixture, in a suspension, in a colloid, in an emulsion. The formulation can be a homogeneous or heterogenous mixture. In some embodiments of any of the aspects, the two or more substances active compound(s) can be comprised by the same or different superstructures, e.g., nanoparticles, liposomes, vectors, cells, scaffolds, or the like, and said superstructure is in solution, mixture, admixture, suspension with a solvent, carrier, or some of the two or more substances. Alternatively, the two or more substances can be present in two or more separate formulations, e.g., in a kit or package comprising multiple formulations in separate containers, to be mixed or brought into contact with each other when an assay is to be performed.

A kit is an assemblage of materials or components, including at least one reagent described herein. The exact nature of the components configured in the kit depends on its intended purpose. In some embodiments of any of the aspects, a kit includes instructions for use. "Instructions for use" typically include a tangible expression describing the technique to be employed in using the components of the kit, e.g., to measure protein-mRNA interactions. Still in accordance with the present invention, "instructions for use" may include a tangible expression describing the preparation of at least one reagent described herein, such as dilution, mixing, or incubation instructions, and the like, typically for an intended purpose. Optionally, the kit also contains other useful components, such as, measuring tools, diluents, buffers, syringes, pharmaceutically acceptable carriers, or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging may also preferably provide an environment that protects from light, humidity, and oxygen. As used herein, the term "package" refers to a suitable solid matrix or material such as glass, plastic, paper, foil, polyester (such as polyethylene terephthalate, or Mylar) and the like, capable of holding the individual kit components. Thus, for example, a package can be a glass vial used to contain suitable quantities of a composition containing a volume of at least one reagent described herein. The packaging material generally has an external label which indicates the contents and/or purpose of the kit and/or its components.

As used herein, the term "agonist" refers to an agent which increases the expression and/or activity of the target by at least 10% or more, e.g. by 10% or more, 50% or more, 100% or more, 200% or more, 500% or more, or 1000% or more. The efficacy of an agonist, e.g. its ability to increase the level and/or activity of the target can be determined, e.g. by measuring the level of an expression product of the target and/or the activity of the target, and/or the editing of a system described herein. Methods for measuring the level of a given mRNA and/or polypeptide are known to one of skill in the art, e.g. RT-PCR with primers can be used to determine the level of RNA, and Western blotting with an antibody can be used to determine the level of a polypeptide. Suitable primers for a given target are readily identified by one of skill in the art, e.g., using software widely available for this purpose (e.g., Primer3 or PrimerBank, which are both available on the world wide web). Antibodies to polypeptide gene expression products of the genes described herein are commercially available, e.g., from AbCam (Cambridge, MA). Assays for measuring the activity of the targets described herein are provided elsewhere herein. In some embodiments of any of the aspects, an agonist can be a polypeptide, a nucleic acid encoding a polypeptide, or a small molecule.

As used herein, "inhibitor" refers to an agent which can decrease the expression and/or activity of a target, e.g. by at least 10% or more, e.g. by 10% or more, 50% or more, 70% or more, 80% or more, 90% or more, 95% or more, or 98% or more. The efficacy of an inhibitor of one or more targets, e.g. its ability to decrease the level and/or activity of the target can be determined, e.g. by measuring the level of an expression product of the target and/or the activity of the target and/or the level of editing of a system described herein. In some embodiments of any of the aspects, the inhibitor can be an inhibitory nucleic acid; an aptamer; an antibody reagent; an antibody; or a small molecule. An inhibitor of a target described herein can inhibit the activity, expression, or accumulation of the target polypeptide. Inhibitors can include inhibitors that act directly on the target itself (e.g., that bind to the protein or transcript, e.g., direct inhibitors). In some embodiments of any of the aspects, an inhibitor of a specified target is an antibody, antibody reagent, or antigen-binding fragment thereof, that specifically binds to the target.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing. The terms also refer to fragments or variants of the polypeptide that maintain at least 50% of the activity or effect, e.g. binding or editing activity, of the full length polypeptide, e.g., a wild-type sequence of one of the proteins described herein. Conservative substitution variants that maintain the activity of wildtype proteins will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants, fragments, and/or fusion proteins can be tested for activity, for example, in the systems and methods described herein. Further discussion of the structure of the relevant proteins can be found elsewhere herein.

In some embodiments, a polypeptide or domain of a polypeptide can be a variant of a sequence described herein, e.g. a variant of a wildtype polypeptide described herein. In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., can bind or edit at least 50% as well as wildtype. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of wildtype, e.g. 110%, 125%, 150%, 175%, 200%, 500%, 1000% or more.

One method of identifying amino acid residues which can be substituted is to align, for example, human to a homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence, or a nucleic acid encoding one of those amino acid sequences. The degree of homology (percent identity) between a native and a mutant sequence can be determined, for example, by comparing the two sequences using freely available computer programs commonly employed for this purpose on the world wide web, e.g, CLUSTAL OMEGA. Alignments are also provided at some of the NCBI entries provided elsewhere herein. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp or BLASTn (available on the world wide web at blast.ncbi.nlm.nih.gov), with default parameters set.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. binding or editing activity and specificity of a native or reference polypeptide is retained.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Typically conservative substitutions for one another also include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments of any of the aspects, the substitution is a mutation to Glu or Asp, e.g., to mimic phosphorylation.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. In some embodiments, the variant is a codon-optimized variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

In some embodiments, a polypeptide or domain of a polypeptide can comprise one or more amino acid substitutions or modifications. In some embodiments, the substitutions and/or modifications can prevent or reduce proteolytic degradation and/or prolong half-life of the polypeptide in a subject. In some embodiments, a polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a polypeptide or domain of a polypeptide as described herein can comprise at least one peptide bond replacement. A polypeptide or domain of a polypeptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a polypeptide or domain of a polypeptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, a polypeptide or domain of a polypeptide as described herein can comprise alternative amino acids. Non-limiting examples of alternative amino acids include phosphorylated amino acids (e.g., that can be incorporated directly in in vitro synthesis); D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statin, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide or domain of a polypeptide can be modified, e.g. by addition of a moiety to one or more of the amino acids that together comprise the peptide. In some embodiments, a polypeptide as described herein can comprise one or more moiety molecules, e.g. 1 or more moiety molecules per polypeptide, 2 or more moiety molecules per polypeptide, 5 or more moiety molecules per polypeptide, 10 or more moiety molecules per polypeptide or more moiety molecules per polypeptide. In some embodiments, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a polypeptide can be increased by the addition of moieties, e.g. PEG, albumin, or other fusion partners (e.g. Fc fragment of an immunoglobin).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established. Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Khudyakov et al. "Artificial DNA: Methods and Applications" CRC Press, 2002; Braman "In Vitro Mutagenesis Protocols" Springer, 2004; and Rapley "The Nucleic Acid Protocols Handbook" Springer 2000; which are herein incorporated by reference in their entireties. In some embodiments, a polypeptide as described herein can be chemically synthesized and mutations and phosphorylated residues can be incorporated as part of the chemical synthesis process.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

In some embodiments of any of the aspects, an RNA is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments of any of the aspects, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2- [known as a methylene (methylimino) or MMI backbone], —CH2-O—N(CH3)-CH2-, —CH2-N(CH3)-N(CH3)-CH2- and —N(CH3)-CH2-CH2- [wherein the native phosphodiester backbone is represented as —O—P—O—CH2-].

In other RNA mimetics suitable or contemplated for use, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

An RNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. For example, the addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12):3185-3193).

Modified RNAs can also contain one or more substituted sugar moieties. The RNAs described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO]mCH3, O(CH2)·nOCH3, O(CH2) nNH2, O(CH2) nCH3, O(CH2)nONH2, and O(CH2)nON [(CH2)nCH3)]2, where n and m are from 1 to about 10. In some embodiments of any of the aspects, RNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an RNA, or a group for improving the pharmacodynamic properties of an RNA, and other substituents having similar properties. In some embodiments of any of the aspects, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON (CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the RNA, particularly the 3' position of the sugar on the 3' terminal nucleotide or in 2'-5' linked dsRNAs and the 5' position of 5' terminal nucleotide. RNAs may also have sugar mimetics such as cyclobutyl moieties in place of the pentofuranosyl sugar.

A nucleic acid can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the nucleic acids featured in the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

The preparation of the modified nucleic acids, backbones, and nucleobases described above are well known in the art.

Another modification of a nucleic acid featured in the invention involves chemically linking to the nucleic acid to one or more ligands, moieties or conjugates that enhance the activity, cellular distribution, pharmacokinetic properties, or cellular uptake of the RNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-

237), or an octadecylamine or hexylamino-carbonyloxycholesterol moiety (Crooke et al., J. Pharmacol. Exp. Ther., 1996, 277:923-937).

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

In some embodiments, the expression of a biomarker(s), target(s), or gene/polypeptide described herein is/are tissue-specific. In some embodiments, the expression of a biomarker(s), target(s), or gene/polypeptide described herein is/are global. In some embodiments, the expression of a biomarker(s), target(s), or gene/polypeptide described herein is systemic.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

In some embodiments, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, the polypeptide(s) or RNA described herein is exogenous. In some embodiments of any of the aspects, the polypeptide(s) or RNA described herein is ectopic. In some embodiments of any of the aspects, the polypeptide(s) or RNA described herein is not endogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

In some embodiments, a nucleic acid encoding a polypeptide as described herein is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, "contacting" refers to any suitable means for delivering, or exposing, an first agent/element to at least a second agent/element. Exemplary delivery methods include, but are not limited to, mixing, pipetting, fluidics delivery (including microfluidics), direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

In all embodiments where a sample is obtained or has been obtained or provided, the sample can be sample taken, obtained, or provided via minimally invasive methods and/or involves only a minor intervention. In some embodiments of any of the aspects, a sample is taken, obtained, or provided by one or more of a blood draw or prick, an epidermal or mucus membrane swab, buccal sampling, saliva sample, a epidermal skin sampling technique, and/or collection of a secreted or expelled bodily fluid (e.g., mucus, urine, sweat, etc), fecal sampling, semen/seminal fluid sampling, or clippings (e.g., of hair or nails). In some embodiments of any of the aspects, the sample comprises, consists of, or consists essentially of blood (or any fraction or component thereof), serum, urine, mucus, epithelial cells, saliva, buccal cells, a secreted or expelled bodily fluid, and/or hair or nail clippings.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

In some embodiments, the present technology may be defined in any of the following numbered paragraphs:

1. A combination comprising
    a) at least one polypeptide or pair of polypeptides comprising i) a candidate RNA-binding domain and ii) a catalytic domain of an RNA-editing enzyme; and
    b) at least one RNA comprising i) at least one candidate cognate binding site for the candidate RNA-binding domain and ii) at least one cognate substrate site for the catalytic domain.
2. The combination of paragraph 1, comprising:
    a plurality of polypeptides or pair of polypeptides collectively comprising a plurality of candidate RNA-binding domains.
3. The combination of paragraph 1, comprising:
    a plurality of polypeptides or pair of polypeptides collectively comprising a plurality of candidate RNA-binding domains; and
    one RNA comprising a cognate binding site.
4. The combination of paragraph 1, comprising:
    a plurality of RNAs collectively comprising a plurality of candidate cognate binding sites.
5. The combination of paragraph 1, comprising:
    one polypeptide or pair of polypeptides comprising a RNA-binding domain; and
    a plurality of RNAs collectively comprising a plurality of candidate cognate binding sites.
6. The combination of any of the preceding paragraphs, wherein the i) at least one candidate cognate binding site for the candidate RNA-binding domain and ii) at least one cognate substrate site for the catalytic domain are not found in the same naturally-occurring RNA.
7. The combination of any one of the preceding paragraphs, wherein the candidate RNA-binding domain comprises: one or more PUF domains, one or more RNA-binding domains of Argonaute, one or more RNA-binding domains of lambda N, one or more REC domains of Cas, or a ribosomal protein.
8. The combination of any one of the preceding paragraphs, wherein the candidate RNA-binding domain and the candidate cognate binding site comprise:
    a) one or more RNA-binding domains of lambda N and a viral hairpin B-Box;
    b) a series of 6 to 16 PUF domains (preferably 8 or 9 domains) and a corresponding series of nucleotides;
    c) a series of 8 to 9 PUF domains and a corresponding series of nucleotides;
    d) one or more RNA-binding domains of Argonaute and a reverse complement sequence of the small non-coding RNA bound by the RNA-binding domain of Argonaute;

e) one or more REC domains of Cas and a CRISPR sequence, guideRNA, or sgRNA; or f) a YTH domain and a m6A methylation site.

9. The combination of any one of the preceding paragraphs, wherein the candidate RNA-binding domain comprises a RNA-binding domain of Argonaute, the candidate cognate binding site comprises a reverse complement sequence of the small non-coding RNA bound by the RNA-binding domain of Argonaute, and the combination further comprises the small non-coding RNA.

10. The combination of any one of the preceding paragraphs, wherein the candidate RNA-binding domain comprises a ribosomal protein and the at least one RNA further comprises a sequence encoding a reporter gene.

11. The combination of any one of the preceding paragraphs, wherein the catalytic domain comprises the catalytic domain of ADAR, APOBEC, Abe7.10, or Cas (e.g., Cas13).

12. The combination of any one of the preceding paragraphs, wherein the catalytic domain comprises ADAR or APOBEC.

13. The combination of paragraph 7, wherein the ADAR is *Danio rerio* ADAR.

14. The combination of paragraph 7, wherein the ADAR is human ADAR.

15. The combination of any one of the preceding paragraphs, wherein the catalytic domain and the cognate substrate site comprise:
   a) the catalytic domain of ADAR and a hairpin substrate site comprising adenosine nucleotides;
   b) the catalytic domain of ADAR and a hairpin substrate site comprising at least one adenosine nucleotide mismatched with a cytosine nucleotide;
   c) the catalytic domain of APOBEC and a single-stranded substrate site comprising at least one cytosine nucleotide.

16. The combination of any one of the preceding paragraphs, wherein the at least one RNA comprises a plurality of tandem repeats of the cognate substrate site.

17. The combination of any one of the preceding paragraphs, wherein the at least one RNA comprises a plurality of tandem repeats of the cognate binding site.

18. The combination of any one of the preceding paragraphs, wherein the at least one RNA further comprises one or more sequencing adaptor sequences.

19. The combination of paragraph 18, wherein the at least one RNA comprises, from 5' to 3':
   a) at least one sequencing adaptor sequence;
   b) the at least one candidate cognate binding site for the candidate RNA-binding domain and the at least one cognate substrate site for the catalytic domain, in either relative order; and
   c) at least one sequence adaptor sequence.

20. The combination of any one of the preceding paragraphs, wherein the at least one RNA further comprises a barcode sequence.

21. The combination of any one of the preceding paragraphs, wherein the at least one RNA further comprises a nuclear enrichment or nuclear localization sequence.

22. The combination of any one of the preceding paragraphs, wherein the at least one RNA further comprises a polyA sequence.

23. The combination of any one of the preceding paragraphs, wherein the polyA sequence comprises SEQ ID NO: 1 or 2.

24. The combination of any one of the preceding paragraphs, wherein a single polypeptide comprises the candidate RNA-binding domain and the catalytic domain of a RNA-editing enzyme.

25. The combination of any one of the preceding paragraphs, wherein a pair of polypeptides comprises the candidate RNA-binding domain and the catalytic domain of a RNA-editing enzyme, and the pair of polypeptides comprises:
   a) a bait polypeptide comprising: a first candidate interaction domain and the candidate RNA-binding domain; and
   b) a prey polypeptide comprising: a second candidate interaction domain and the catalytic domain of a RNA-editing enzyme.

26. A cell comprising or expressing the combination of any one of the preceding paragraphs.

27. A method of detecting the strength of the binding of a candidate RNA-binding domain to a candidate cognate binding site, the method comprising:
   a) contacting the at least one polypeptide of any one of paragraphs 1-26 with the at least one RNA of any one of paragraphs 1-26 for a period of time; and
   b) detecting the amount of editing present in the cognate substrate site.

28. A method of detecting the strength of the binding of a candidate RNA-binding domain to a candidate cognate binding site, the method comprising:
   a) contacting the at least one polypeptide of any one of paragraphs 1-26 with the at least one RNA of any one of paragraphs 1-26 for a period of time; and then
   b) detecting the amount of editing present in the cognate substrate site.

29. The method of any one of the preceding paragraphs, wherein the amount of editing generated during the period of time correlates to the strength of the binding.

30. The method of any one of the preceding paragraphs, wherein:
   a) the catalytic domain is a catalytic domain of ADAR and the amount of editing is the number of A to I edits;
   b) the catalytic domain is a catalytic domain of APOBEC and the amount of editing is the number of C to U edits.

31. The method of any one of the preceding paragraphs, wherein the detecting comprises sequencing of the at least one RNA; fluorescence detection; reporter gene detection.

32. The method of any one of the preceding paragraphs, wherein the detecting comprises high-throughput sequencing of the at least one RNA.

33. The method of any one of the preceding paragraphs, wherein step a) further comprises contacting the polypeptide and RNA with a drug candidate, a candidate RNA-editing inhibitor, or a candidate RNA-editing agonist.

34. The method of any one of the preceding paragraphs, wherein the method further comprises performing steps a) and b) for a plurality of different polypeptides or RNAs to determine relative binding strength or editing activity.

35. The method of paragraph 34, wherein the plurality of different polypeptides comprise different sequences or modifications in the RNA-binding domain.

36. The method of paragraph 34, wherein the plurality of different polypeptides comprise different post-translational modifications in the RNA-binding domain.

37. The method of paragraph 34, wherein the plurality of different RNAs comprise different sequences or modifications in the cognate binding site.
38. The method of any one of the preceding paragraphs, wherein the contacting step occurs in a cell or organism.

In some embodiments, the present technology may be defined in any of the following numbered paragraphs:

1. A combination comprising
   a) at least one polypeptide or pair of polypeptides comprising i) a candidate RNA-binding domain and ii) a catalytic domain of an RNA-editing enzyme; and
   b) at least one RNA comprising i) at least one candidate cognate binding site for the candidate RNA-binding domain and ii) at least one cognate substrate site for the catalytic domain.
2. The combination of paragraph 1, comprising:
   a plurality of polypeptides or pair of polypeptides collectively comprising a plurality of candidate RNA-binding domains.
3. The combination of paragraph 1, comprising:
   a plurality of polypeptides or pair of polypeptides collectively comprising a plurality of candidate RNA-binding domains; and
   one RNA comprising a cognate binding site.
4. The combination of paragraph 1, comprising:
   a plurality of RNAs collectively comprising a plurality of candidate cognate binding sites.
5. The combination of paragraph 1, comprising:
   one polypeptide or pair of polypeptides comprising a RNA-binding domain; and
   a plurality of RNAs collectively comprising a plurality of candidate cognate binding sites.
6. The combination of any of the preceding paragraphs, wherein the i) at least one candidate cognate binding site for the candidate RNA-binding domain and ii) at least one cognate substrate site for the catalytic domain are not found in the same naturally-occurring RNA.
7. The combination of any one of the preceding paragraphs, wherein the candidate RNA-binding domain comprises: one or more PUF domains, one or more RNA-binding domains of Argonaute, one or more RNA-binding domains of lambda N, one or more REC domains of Cas, Embryonic Lethal Abnormal Vision (ELAV) RNA recognition motif (RRM), or a ribosomal protein.
8. The combination of any one of the preceding paragraphs, wherein the candidate RNA-binding domain and the candidate cognate binding site comprise:
   a) one or more RNA-binding domains of lambda N and a viral hairpin B-Box;
   b) a series of 6 to 16 PUF domains (preferably 8 or 9 domains) and a corresponding series of nucleotides;
   c) a series of 8 to 9 PUF domains and a corresponding series of nucleotides;
   d) one or more RNA-binding domains of Argonaute and a reverse complement sequence of the small non-coding RNA bound by the RNA-binding domain of Argonaute;
   e) one or more REC domains of Cas and a CRISPR sequence, guideRNA, or sgRNA;
   f) one or more ELAV RRMs and an AU-rich element (ARE);
   g) one or more TDP-43 RRMs and one or more U G/T G repeats; or
   h) a YTH domain and a m6A methylation site.
9. The combination of any one of the preceding paragraphs, wherein the candidate RNA-binding domain comprises a RNA-binding domain of Argonaute, the candidate cognate binding site comprises a reverse complement sequence of the small non-coding RNA bound by the RNA-binding domain of Argonaute, and the combination further comprises the small non-coding RNA.
10. The combination of any one of the preceding paragraphs, wherein the candidate RNA-binding domain comprises a ribosomal protein and the at least one RNA further comprises a sequence encoding a reporter gene.
11. The combination of any one of the preceding paragraphs, wherein the catalytic domain comprises the catalytic domain of ADAR, APOBEC, Abe7.10, or Cas (e.g., Cas13).
12. The combination of any one of the preceding paragraphs, wherein the catalytic domain comprises ADAR or APOBEC.
13. The combination of paragraph 7, wherein the ADAR is *Danio rerio* ADAR.
14. The combination of paragraph 7, wherein the ADAR is human ADAR.
15. The combination of any one of the preceding paragraphs, wherein the catalytic domain and the cognate substrate site comprise:
    a) the catalytic domain of ADAR and a hairpin substrate site comprising adenosine nucleotides;
    b) the catalytic domain of ADAR and a hairpin substrate site comprising at least one adenosine nucleotide mismatched with a cytosine nucleotide;
    c) the catalytic domain of APOBEC and a single-stranded substrate site comprising at least one cytosine nucleotide.
16. The combination of any one of the preceding paragraphs, wherein the at least one RNA comprises a plurality of tandem repeats of the cognate substrate site.
17. The combination of any one of the preceding paragraphs, wherein the at least one RNA comprises a plurality of tandem repeats of the cognate binding site.
18. The combination of any one of the preceding paragraphs, wherein the at least one RNA further comprises one or more sequencing adaptor sequences.
19. The combination of paragraph 18, wherein the at least one RNA comprises, from 5' to 3':
    a) at least one sequencing adaptor sequence;
    b) the at least one candidate cognate binding site for the candidate RNA-binding domain and the at least one cognate substrate site for the catalytic domain, in either relative order; and
    c) at least one sequence adaptor sequence.
20. The combination of paragraph 18, wherein the at least one RNA comprises, from 5' to 3':
    a) at least one sequence encoding a first reporter gene;
    b) a domain comprising, in any order: the at least one candidate cognate binding site for the candidate RNA-binding domain, and the at least one cognate substrate site for the catalytic domain wherein the at least one cognate substrate site for the catalytic domain further comprises a stop codon; and
    c) at least one sequence encoding a second reporter gene.
21. The combination of any one of the preceding paragraphs, wherein the at least one RNA further comprises a barcode sequence.

22. The combination of any one of the preceding paragraphs, wherein the at least one RNA further comprises a nuclear enrichment or nuclear localization sequence.
23. The combination of any one of the preceding paragraphs, wherein the at least one RNA further comprises a polyA sequence.
24. The combination of any one of the preceding paragraphs, wherein the polyA sequence comprises SEQ ID NO: 1, 2, 24, or 25.
25. The combination of any one of the preceding paragraphs, wherein a single polypeptide comprises the candidate RNA-binding domain and the catalytic domain of a RNA-editing enzyme.
26. The combination of any one of the preceding paragraphs, wherein a pair of polypeptides comprises the candidate RNA-binding domain and the catalytic domain of a RNA-editing enzyme, and the pair of polypeptides comprises:
    a) a bait polypeptide comprising: a first candidate interaction domain and the candidate RNA-binding domain; and
    b) a prey polypeptide comprising: a second candidate interaction domain and the catalytic domain of a RNA-editing enzyme.
27. A cell comprising or expressing the combination of any one of the preceding paragraphs.
28. A method of detecting the strength of the binding of a candidate RNA-binding domain to a candidate cognate binding site, the method comprising:
    a) contacting the at least one polypeptide of any one of paragraphs 1-26 with the at least one RNA of any one of paragraphs 1-26 for a period of time; and
    b) detecting the amount of editing present in the cognate substrate site.
29. A method of detecting the strength of the binding of a candidate RNA-binding domain to a candidate cognate binding site, the method comprising:
    a) contacting the at least one polypeptide of any one of paragraphs 1-26 with the at least one RNA of any one of paragraphs 1-26 for a period of time; and then
    b) detecting the amount of editing present in the cognate substrate site.
30. The method of any one of the preceding paragraphs, wherein the amount of editing generated during the period of time correlates to the strength of the binding.
31. The method of any one of the preceding paragraphs, wherein:
    a) the catalytic domain is a catalytic domain of ADAR and the amount of editing is the number of A to I edits;
    b) the catalytic domain is a catalytic domain of APOBEC and the amount of editing is the number of C to U edits.
32. The method of any one of the preceding paragraphs, wherein the detecting comprises sequencing of the at least one RNA; fluorescence detection; reporter gene detection.
33. The method of any one of the preceding paragraphs, wherein the detecting comprises high-throughput sequencing of the at least one RNA.
34. The method of any one of the preceding paragraphs, wherein step a) further comprises contacting the polypeptide and RNA with a drug candidate, a candidate RNA-editing inhibitor, or a candidate RNA-editing agonist.
35. The method of any one of the preceding paragraphs, wherein the method further comprises performing steps a) and b) for a plurality of different polypeptides or RNAs to determine relative binding strength or editing activity.
36. The method of paragraph 34, wherein the plurality of different polypeptides comprise different sequences or modifications in the RNA-binding domain.
37. The method of paragraph 34, wherein the plurality of different polypeptides comprise different post-translational modifications in the RNA-binding domain.
38. The method of paragraph 34, wherein the plurality of different RNAs comprise different sequences or modifications in the cognate binding site.
39. The method of any one of the preceding paragraphs, wherein the contacting step occurs in a cell or organism.

In some embodiments, the present technology may be defined in any of the following numbered paragraphs:

1. A combination comprising
    a) at least one polypeptide or pair of polypeptides comprising i) a candidate RNA-binding domain and ii) a catalytic domain of an RNA-editing enzyme; and
    b) at least one RNA comprising i) at least one candidate cognate binding site for the candidate RNA-binding domain and ii) at least one cognate substrate site for the catalytic domain.
2. The combination of paragraph 1, comprising:
    a plurality of polypeptides or pair of polypeptides collectively comprising a plurality of candidate RNA-binding domains.
3. The combination of paragraph 1, comprising:
    a plurality of polypeptides or pair of polypeptides collectively comprising a plurality of candidate RNA-binding domains; and
    one RNA comprising a cognate binding site.
4. The combination of paragraph 1, comprising:
    a plurality of RNAs collectively comprising a plurality of candidate cognate binding sites.
5. The combination of paragraph 1, comprising:
    one polypeptide or pair of polypeptides comprising a RNA-binding domain; and
    a plurality of RNAs collectively comprising a plurality of candidate cognate binding sites.
6. The combination of paragraph 1, wherein the i) at least one candidate cognate binding site for the candidate RNA-binding domain and ii) at least one cognate substrate site for the catalytic domain are not found in the same naturally-occurring RNA.
7. The combination of paragraph 1, wherein the candidate RNA-binding domain comprises: one or more PUF domains, one or more RNA-binding domains of Argonaute, one or more RNA-binding domains of lambda N, one or more REC domains of Cas, Embryonic Lethal Abnormal Vision (ELAV) RNA recognition motif (RRM), or a ribosomal protein.
8. The combination of paragraph 1, wherein the candidate RNA-binding domain and the candidate cognate binding site comprise:
    a) one or more RNA-binding domains of lambda N and a viral hairpin B-Box;
    b) a series of 6 to 16 PUF domains (preferably 8 or 9 domains) and a corresponding series of nucleotides;
    c) a series of 8 to 9 PUF domains and a corresponding series of nucleotides;

d) one or more RNA-binding domains of Argonaute and a reverse complement sequence of the small non-coding RNA bound by the RNA-binding domain of Argonaute;
e) one or more REC domains of Cas and a CRISPR sequence, guideRNA, or sgRNA;
f) one or more ELAV RRMs and an AU-rich element (ARE);
g) one or more TDP-43 RRMs and one or more U G/T G repeats; or
h) a YTH domain and a m6A methylation site.

9. The combination of paragraph 1, wherein the candidate RNA-binding domain comprises a RNA-binding domain of Argonaute, the candidate cognate binding site comprises a reverse complement sequence of the small non-coding RNA bound by the RNA-binding domain of Argonaute, and the combination further comprises the small non-coding RNA.

10. The combination of paragraph 1, wherein the candidate RNA-binding domain comprises a ribosomal protein and the at least one RNA further comprises a sequence encoding a reporter gene.

11. The combination of paragraph 1, wherein the catalytic domain comprises the catalytic domain of ADAR, APOBEC, Abe7.10, or Cas.

12. The combination of paragraph 1, wherein the catalytic domain and the cognate substrate site comprise:
a) the catalytic domain of ADAR and a hairpin substrate site comprising adenosine nucleotides;
b) the catalytic domain of ADAR and a hairpin substrate site comprising at least one adenosine nucleotide mismatched with a cytosine nucleotide;
c) the catalytic domain of APOBEC and a single-stranded substrate site comprising at least one cytosine nucleotide.

13. The combination of paragraph 1, wherein the at least one RNA comprises at least one of: a plurality of tandem repeats of the cognate substrate site and a plurality of tandem repeats of the cognate binding site.

14. The combination of paragraph 1, wherein the at least one RNA further comprises one or more sequencing adaptor sequences.

15. The combination of paragraph 14, wherein the at least one RNA comprises, from 5' to 3':
a) at least one sequence encoding a first reporter gene;
b) a domain comprising, in any order: the at least one candidate cognate binding site for the candidate RNA-binding domain, and the at least one cognate substrate site for the catalytic domain wherein the at least one cognate substrate site for the catalytic domain further comprises a stop codon; and
c) at least one sequence encoding a second reporter gene.

16. The combination of paragraph 1, wherein the at least one RNA further comprises at least one of: a barcode sequence, a nuclear enrichment sequence, a nuclear localization sequence, and a polyA sequence.

17. The combination of paragraph 1, wherein a single polypeptide comprises the candidate RNA-binding domain and the catalytic domain of a RNA-editing enzyme.

18. The combination of paragraph 1, wherein a pair of polypeptides comprises the candidate RNA-binding domain and the catalytic domain of a RNA-editing enzyme, and the pair of polypeptides comprises:
a) a bait polypeptide comprising: a first candidate interaction domain and the candidate RNA-binding domain; and
b) a prey polypeptide comprising: a second candidate interaction domain and the catalytic domain of a RNA-editing enzyme.

19. A cell comprising or expressing the combination of paragraph 1.

20. A method of detecting the strength of the binding of a candidate RNA-binding domain to a candidate cognate binding site, the method comprising:
a) contacting the at least one polypeptide of paragraph 1 with the at least one RNA of paragraph 1 for a period of time; and
b) detecting the amount of editing present in the cognate substrate site.

21. The method of paragraph 20, wherein the amount of editing generated during the period of time correlates to the strength of the binding.

22. The method of paragraph 20, wherein:
a) the catalytic domain is a catalytic domain of ADAR and the amount of editing is the number of A to I edits;
b) the catalytic domain is a catalytic domain of APOBEC and the amount of editing is the number of C to U edits.

23. The method of paragraph 20, wherein the detecting comprises sequencing of the at least one RNA; fluorescence detection; reporter gene detection.

24. The method of paragraph 20, wherein the detecting comprises high-throughput sequencing of the at least one RNA.

25. The method of paragraph 20, wherein step a) further comprises contacting the polypeptide and RNA with a drug candidate, a candidate RNA-editing inhibitor, or a candidate RNA-editing agonist.

26. The method of paragraph 20, wherein the method further comprises performing steps a) and b) for a plurality of different polypeptides or RNAs to determine relative binding strength or editing activity.

27. The method of paragraph 26, wherein the plurality of different polypeptides comprise different sequences or modifications in the RNA-binding domain.

28. The method of paragraph 26, wherein the plurality of different polypeptides comprise different post-translational modifications in the RNA-binding domain.

29. The method of paragraph 26, wherein the plurality of different RNAs comprise different sequences or modifications in the cognate binding site.

30. The method of paragraph 20, wherein the contacting step occurs in a cell or organism.

The technology described herein is further illustrated by the following examples which in no way should be construed as being further limiting.

EXAMPLES

Example 1—Reporter System to Record the Strength of RNA Protein Interactions Regulation of mRNA processing, translation and decay by RNA-binding proteins are universal and fundamental processes of biological systems. Deep understanding of RNA-protein interactions in health and disease will facilitate the development of therapeutic interventions in the affected systems. Described herein is a reporter system that records the cumulative time that an RNA-binding protein (RBP) spends bound to its target RNA.

This is achieved by using a split reporter, consisting of
1) an RBP (polypeptide) fused to the catalytic domain of ADAR, an RNA-editing enzyme, and
2) an RNA containing a potential RBP binding site and an optimal RNA substrate for ADAR (recorder).

When the two elements are expressed together, the amount of editing in the recorder is proportional to the strength of the RNA-RBP interaction. This technology can be applied towards discovery of better RNA-target sites for the RBP of interest or to assess the impact of drugs or RBP modifications on the strength of the RNA-protein interaction.

TRIBE (Targets of RNA-binding proteins identified by editing, US20190390186A1) (PMID: 27040499) and STAMP (Surveying Targets by APOBEC-Mediated Profiling) (PMID: 33963355) are two high-throughput techniques that identify RBP target sites in mRNAs. Both techniques express the RBP of interest fused to the catalytic domain of an RNA-editing enzyme, ADAR in TRIBE and APOBEC in STAMP. Upon binding to the endogenous mRNAs, mediated by the RBP, the attached editing enzyme will edit the RNA neighboring sequences. The edited sites are subsequently identified by sequencing as mutations from the reference sequence.

The currently described interactome recorder also uses an RBP fused to ADAR, but unlike the prior art, the methods and compositions described herein comprise a second element, a reporter mRNA that encodes a potential RBP binding site and an optimal substrate of ADAR. The advantages of this strategy over the prior art is that 1) the present technology is not limited by the presence of adequate ADAR substrates in the endogenous target mRNAs and 2) the editing will only occur if the binding site is actually a good substrate for the RBP, facilitating the identification of the binding sites.

The TimeSTAMP technique (WO2020018509A2), uses an ADAR substrate to record the age of mRNAs. The currently described technology is different from TimeSTAMP at least because the technology described herein relates to the binding of different RBPs to the recorder to measure their RNA-protein interaction strength, while TimeSTAMP always uses the same RBP to measure how long the recorder RNA has been expressed.

Ultimately, the unique combination of RBP-ADAR with the recorder permits testing of modifiers of RNA-protein interactions, and is amenable to be used as a screening method for small molecules that modify these interactions.

Potential Applications

The main application of the currently described technology is its use as a screening method to identify small molecules that modify RBP-RNA interactions. This recorder system has high specificity, and the signal is time-responsive and dose-responsive, providing the system with a broad dynamic range. A main advantage versus prior art is that this technique is in vivo, capturing all the nuances of the RBP-RNA interaction in the context of a living cell, and therefore is closer to the therapeutic scenario.

An additional product of the technology described herein is a dataset of a RBP's target sites across the transcriptome of different cell types. Prior art has identified the consensus binding motifs of multiple RBPs but the direct identification of their binding sites in the cellular transcriptome is limited to a few RBPs in few cell types. The technology described herein streamlines the recovery of endogenous RBP binding sites for multiple cell types and conditions. An experimentally validated dataset of RBP binding sites will be of interest to design therapeutic interventions targeting RBPs.

The technology described herein can also be utilized to monitor the binding of RBP involved in epitranscriptomics. These proteins write, read, or erase modifications in the RNA such as m6A methylation, and are relevant for development and cancer. The technology described herein, contrary to prior art, can measure the interaction of these RBPs with modified RNA in vivo, to identify preferred binding sites or the stochiometry of methylated and non-methylated sites.

The technology described herein can also be utilized to engineer designer proteins that bind to RNA targets of interest. These artificial proteins are based on the array of PUF RNA-binding domains of Pumilio protein. Each PUF domain recognizes one nucleotide, and the PUF domains are arranged in a scaffold containing up to 8 PUF domains. The technology described herein can be used to screen a library of PUF arrays to determine which one binds to a sequence of interest.

The technology described herein can also be used to determine microRNA activity in vivo. The fusion of Argonaute protein to ADAR permits determination of the strength of binding to the microRNA target site of interest in the cellular context. The higher the editing of the recorder, the stronger is the binding of the microRNA to the target site. This configuration of the technology can also be used to interrogate which microRNAs are most active in the cells, by combining Argonaute-ADAR with a library of recorders with 8-nucleotide randomized sequence. By determining which 8-nucleotide sequence motif drives recorder editing, it can be determined which microRNAs are more expressed and active in the cell.

The technology described herein can also be used to determine protein-protein interactions. In such embodiments, for two proteins of interest, one is the bait and the other is the prey. The bait protein is tethered to the recorder RNA by fusion to a RNA-binding peptide (lambda) that recognizes a viral hairpin B-Box. Alternatively, the recoder RNA can be fused to Ms2 (which recognizes a cognate hairpin). The prey protein is fused to catalytic domain of, e.g., ADAR. The co-expression of the bait and prey chimeras, together with the recorder, will allow the introduction of edits in the recorder if the two proteins interact and bring in close contact the recorder RNA molecule with the recorder.

The technology described herein can also be used to determine the structural determinants of the interaction between an RNA-binding protein and a structured target. In this scenario the binding site in the recorder mRNA is a structured RNA. Cloning of RNAs with different structure variants in the recorder will permit dissection of which specific structural features are required for the RNA-protein interaction.

The technology described herein can also be used to determine translation efficiency. The cells of interest are modified in a way that an endogenous ribosomal protein is fused to ADAR catalytic domain. This fusion will generate ribosomes tagged with ADAR catalytic domain. When the ribosomes translate the reporter gene encoded in the reporter, they will be in close proximity to the ADAR substrate in the 3'UTR of the recorder, which will facilitate RNA editing. The more ribosomes translate the reporter gene, more edited the reporter will be. A variant of this approach will incorporate random sequences that may modulate translation efficiency. These sequences are cloned next to the ADAR substrate, so that it is possible to determine how much each sequence modulates translation and which sequence is responsible.

The technology described herein can also be used to determine how post-translational modifications of RNA-binding proteins modulate their RNA-binding activity. Using a recorder that contains the preferred RNA-binding site for the protein of interest, wild-type and mutant RNA-binding protein fused to the catalytic domain of ADAR are expressed. The mutations in the RNA-binding protein are designed to mimic or prevent post-translational modifications of the protein of interest. By determining the number of edits in the recorder RNA, it will be elucidated if the post-translational modifications act as activators or inhibitors of the RNA-binding protein of interest.

Technical Description

Rationale: Current in vivo reporters only evaluate the binding of a RBP through their impact on a reporter mRNA (enhanced translation, stabilization, decay, and localization) but lack the granularity to distinguish differences in binding strength. Described herein is a new reporter system that tracks RNA-protein interactions through RNA edits, where the number of positions edited are proportional to the cumulative time that the RBP is bound to the target mRNA.

An exemplary current reporter design has two parts (FIG. 1): i) the writer: the RBP of interest fused to the catalytic domain of zebrafish ADAR; and ii) the recorder: mRNA that contains the RBP binding site followed by a hairpin substrate for ADAR editing. The rationale of the RBP-Adar fusion derives from the TRIBE technique (1), which looks for editing sites across the transcriptome. The difference here is that the technology described herein provides an optimal substrate for the RBP-Adar fusion attached the consensus RBP binding site. This configuration will permit testing mutations in the protein that may affect RNA-binding, which will read out as the number of adenine to inosine (A-to-I)x' edits in the recorder hairpin.

Cloning of the Interactome Recorder System:

To generate the writer (FIG. 1), the catalytic domain of zebrafish Adarb1a (aminoacids 318-720 (SEQ ID NO: 3) was cloned into the pCS2+ vector, with a multicloning site at the 5' of the Adar catalytic domain to insert the selected and prioritized RBP coding sequences. Finally, the RBP-Adar fusion will be transcribed with Sp6 RNA polymerase (mMessage Machine Sp6 transcription kit, ThermoFisher), to generate the mRNA for injection into zebrafish embryos or transfection in mammalian cell lines.

Figure 2A:
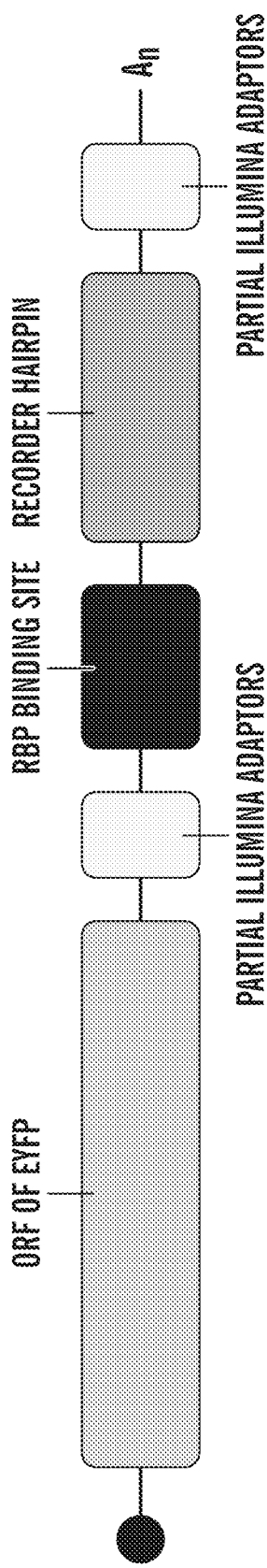
Figure 2B:
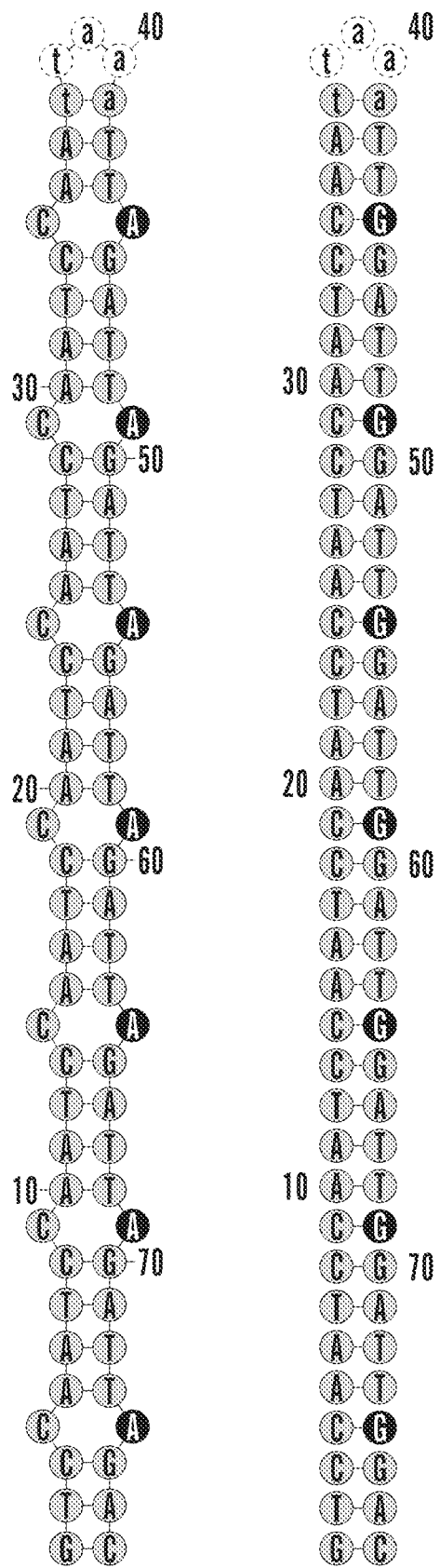
Figure 2C:
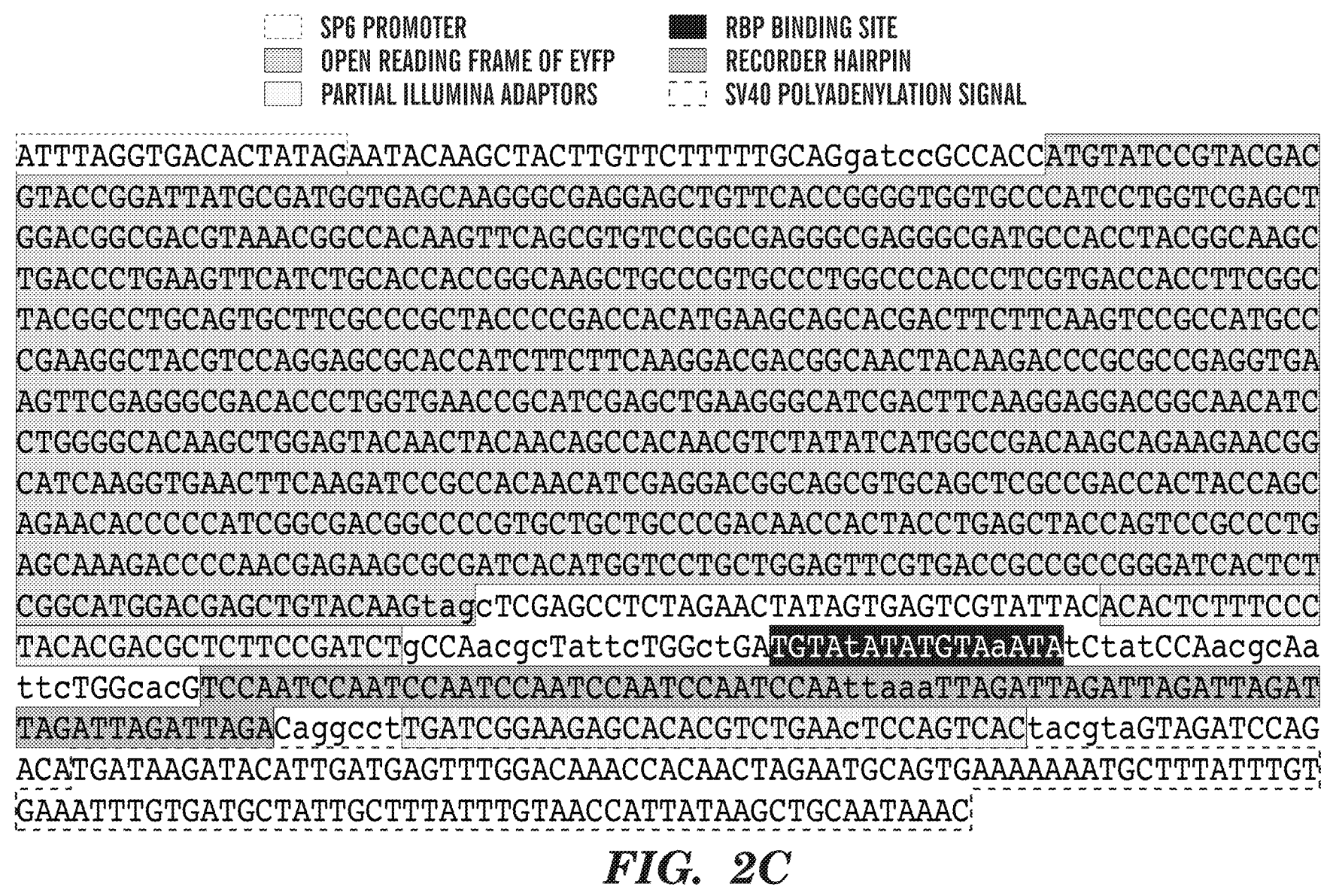

This exemplary recorder comprises two main modules: i) the RBP binding motif and ii) the Adar-substrate hairpin (FIG. 1), all flanked by partial TruSeq Illumina adaptors and imbedded on the 3'UTR of EYFP, to facilitate subsequent cloning of libraries for Illumina sequencing. For the RBP motifs, up to 5× tandem repeats of the consensus sequence of the most enriched 6-mer sequences inferred from public databases will be used. The Adar substrate is a 75-nucleotide hairpin with 6 mismatches(2), where the A to be edited is flanked by U and G (FIG. 2B). This UAG substrate increases the base-flipping of the central adenine(3), resulting in an increased catalytic rate compared to other sequence configurations(3). The final construct was cloned on pCS2+ vector, to facilitate transcription with Sp6 RNA polymerase.

General Usage of the Interactome Recorder System:

To quantify RNA-protein interactions with this reporter system, for each RBP the writer and recorder mRNA pair will be co-injected into one-cell stage zebrafish embryos (100 pg per embryo of each mRNA) and incubated at 28.5° C. for 4 hours. Next, 25 embryos per sample will be collected in triplicate and extract total RNA with TRIzol. The RNA will be retrotranscribed using LunaScript RT SuperMix (New England Biolabs) and the cDNA amplified with oligos matching the TruSeq adaptors. The PCR product will be submitted for Illumina sequencing at the Boston University Microarray and Sequencing core. When the interactome recorder assay is performed in cells, the mRNA will be transfected directly into the desired cell line.

Sequencing Analysis:

Raw reads will be adapter and quality trimmed using Trim Galore! (v.0.5.0). The reads passing quality control with FastQC (v.0.11.6) will be then aligned to the recorder using bowtie2 (v.2.3)(4), allowing up to 6 mismatches to account for the edits. Next, all the A-to-G transitions from all reads will be aggregated and this number normalized by the total number of reads. This result will be the interaction score. The larger the score, the more cumulative time that the RBP has been bound to the recorder mRNA. As a control, the catalytic domain of Adar will be injected alone to determine the background editing activity.

Figure 3A:
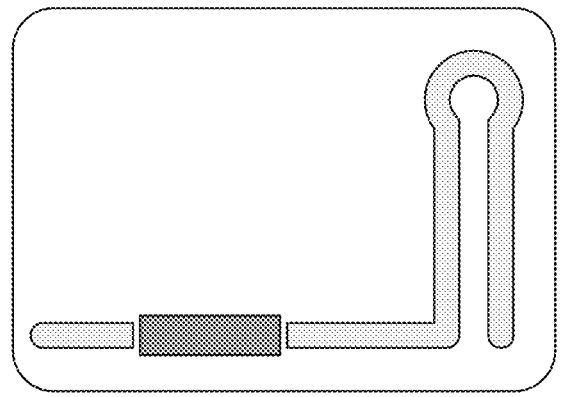
FIGS. 3A-3D depict quality controls to ensure the specificity of the interactome recorder assay.

Quality Controls of the Interactome Recorder System:

To ensure that the read out of the interactome recorder system for a given RBP is proportional to the RNA-RBP interaction, it must first be determined that the editing of the recorder is driven by the specific interaction of the chosen RBP and its target RNA sequence. To this end, the following controls will be conducted by introducing the corresponding mRNAs in zebrafish embryos or mammalian cell lines:

Recorder only: This transfection tests the background levels of endogenous ADAR-mediated editing of the recorder in the cells of interest (FIG. 3A).

Figure 3B:
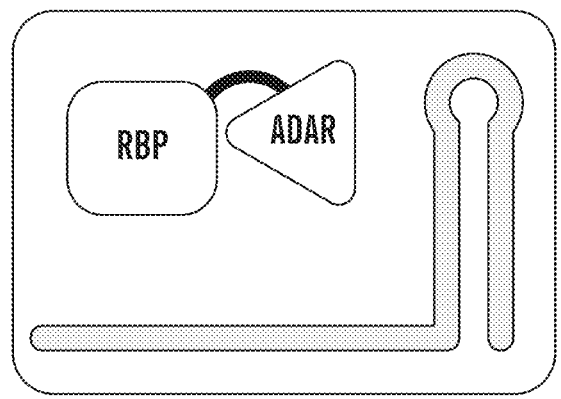
Figure 3C:
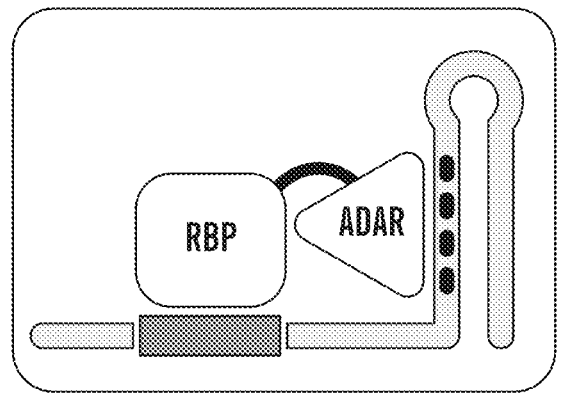
Figure 3D:
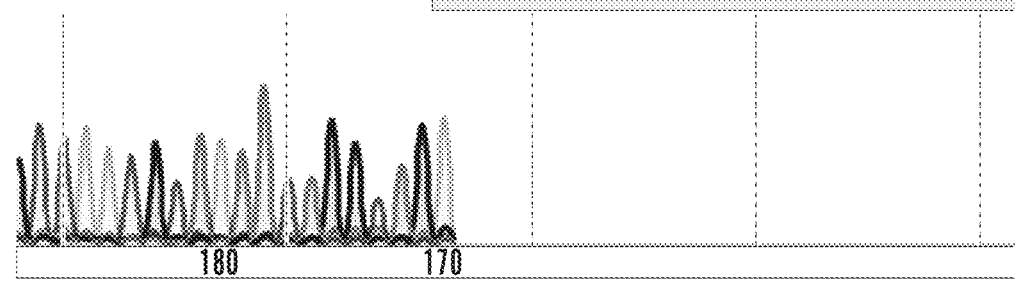
Figure 3D:
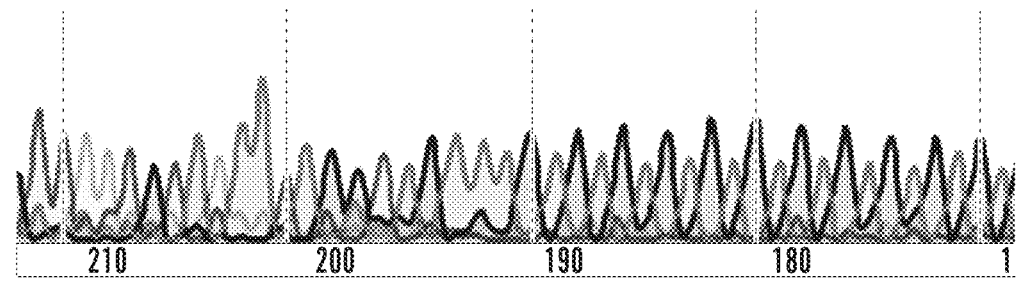
Figure 3D:
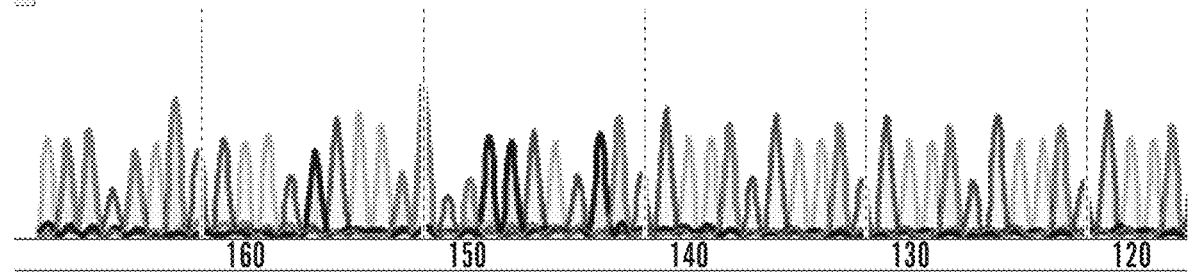
Figure 3D:
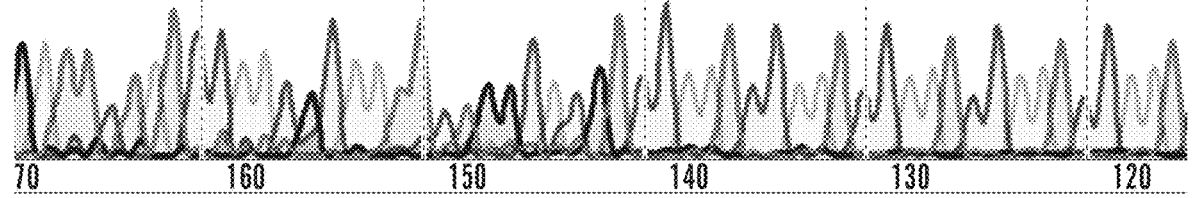
Figure 3D:
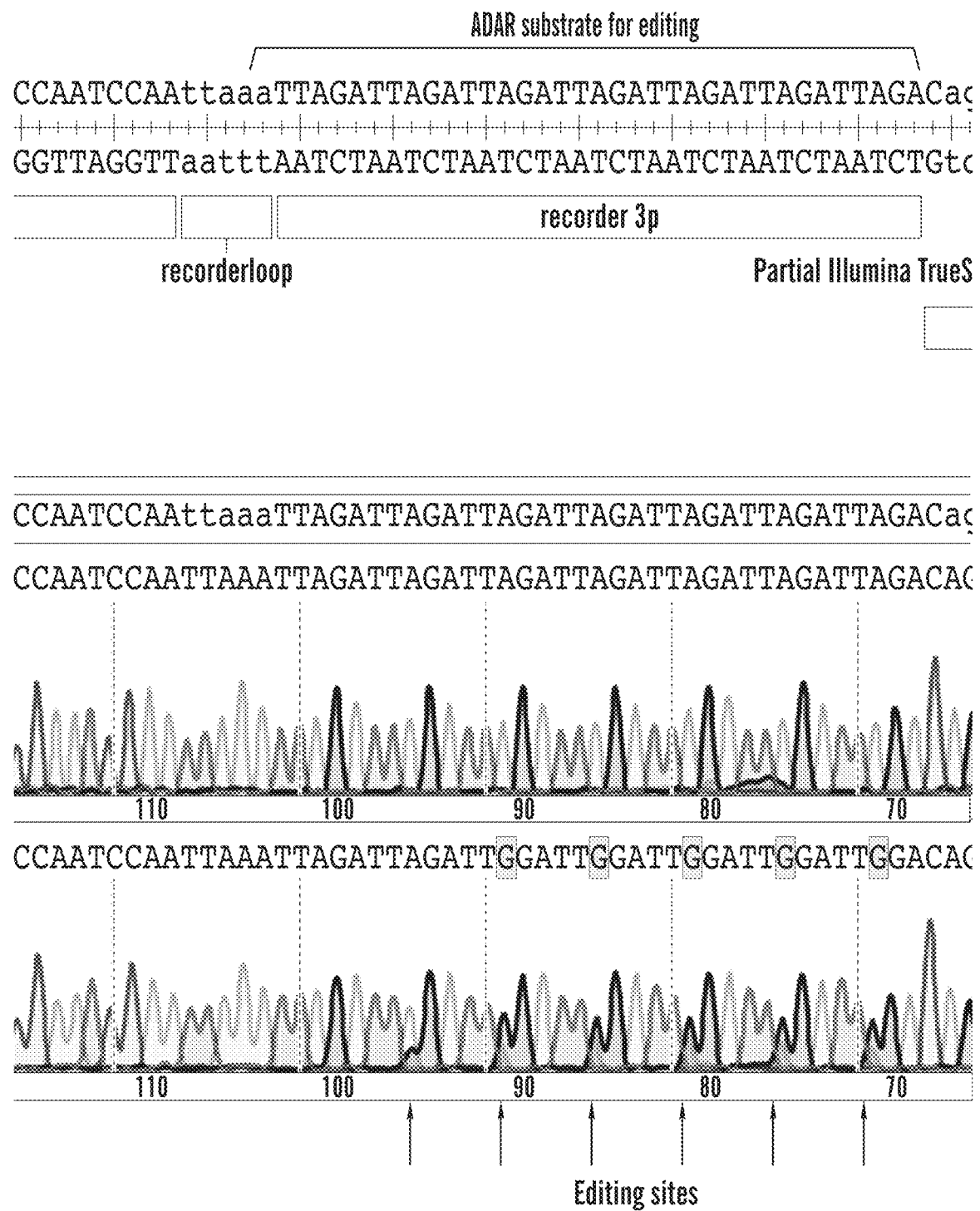

Writer+recorder without binding site: This transfection will test if the binding of the RBP is sequence dependent (FIG. 3B). If we detect editing without the binding site, the interactome recorder cannot be used with that RBP.

Additional controls involve testing that the editing of the recorder is i) proportional to the time of incubation by collecting samples at different timepoints, and ii) proportional to the dose of writer, by transfecting different amounts of RBP-Adar fusion.

Figure 4:
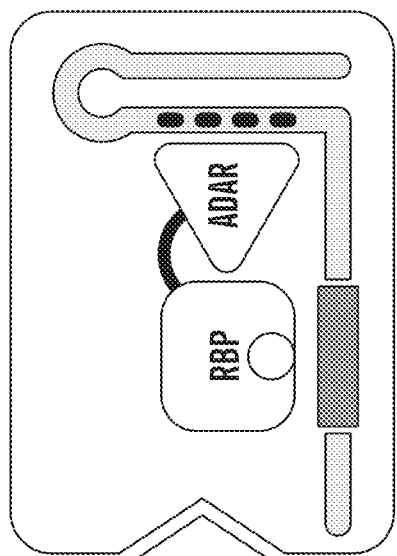
FIG. 4 depicts a schematic of the concept of how interactome recorder can be used to determine the impact of small molecules in the RNA-protein binding. The cartoon shows how a small molecule (circle) activates the RBP- RNA interactions and facilitates editing. An alternative scenario would contemplate that the small molecule disrupts the RBP-RNA interaction.
Figure 4:
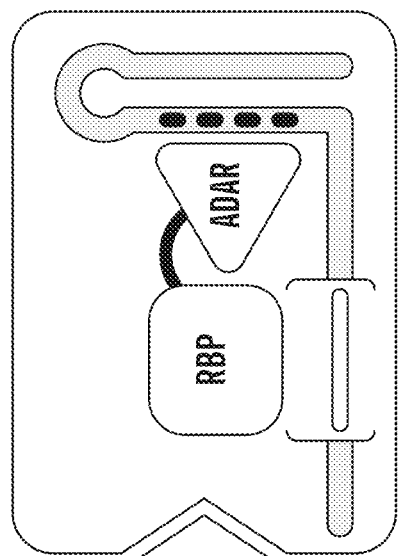

Usage of the interactome recorder system to screen small molecules modulating RNA-protein interactions (FIG. 4):

When a validated pair of writer and recorder for a given RBP is identified, the transfection of the paired mRNAs is repeated, but the cells or the embryos are now incubated with different test drugs at different concentrations. The number of edits in the control without drug is a reference to determine if the drug enhances or interferes with the RNA-RBP interaction.

Figure 5:
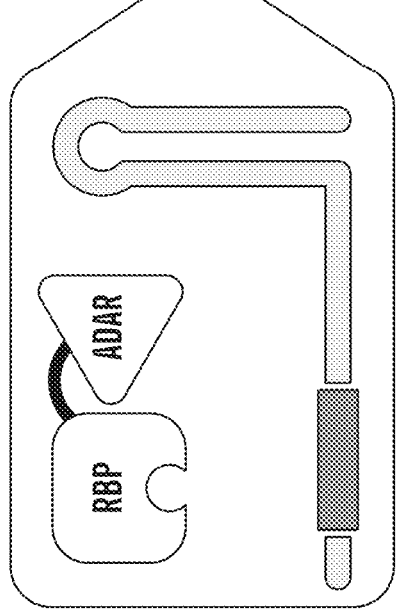
FIG. 5 depict a schematic of the concept of how interactome recorder can be used to determine the binding sites of a given RBP, using a library of recorder molecules, each encoding a different sequence in the RBP landing site. This sequence can be derived from the cloning of a randomized oligo or derived form fragments of mRNA of a cell or tissue of interest. Only the recorder molecules encoding the appropriate sequence, will recruit the RBP-Adar fusion and become edited.
Figure 5:
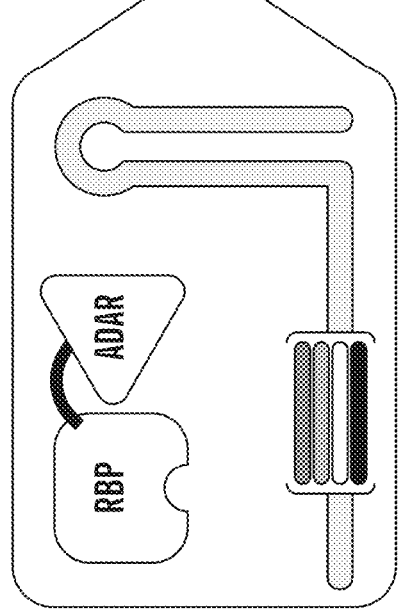

Usage of the interactome recorder system to determine the RNA binding motif of a given RBP (FIG. 5):

Once an RBP-Adar fusion that has passed the quality controls for specificity, its consensus RNA-binding sequence can be determined in a way that is independent of antibodies or UV-mediated cross-linking. In cells or zebrafish embryos, the selected RBP-Adar fusion is transfected together with a recorder library where the corresponding RBP-binding site is fully randomized. This usually corresponds to a stretch of 8 nucleotides between the Illumina adaptors. Upon transfection and processing, only the recorder molecules containing a sequence that is conducive to the binding of the RBP will show some degree of editing. Next, the 8-mer sequence motifs are arrange according to the total number of edits in their corresponding recorder sequences. A consensus sequence can be extracted from this list, and the level of stringency can be adjusted be setting editing thresholds to the sequences that will be included to calculate the consensus sequence.

Figure 6:
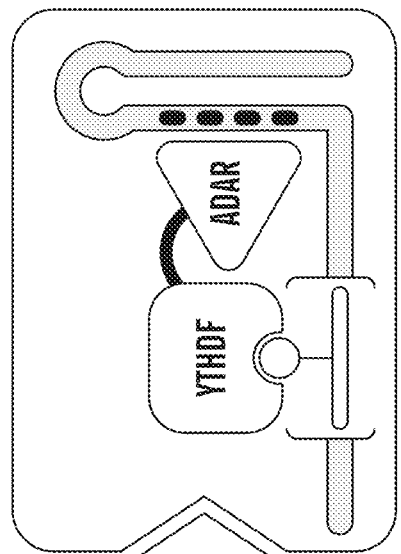
FIG. 6 depicts a schematic of the concept of how interactome recorder can be used to determine epitranscriptomic modification sites in mRNAs. This embodiment involves using a library of recorder molecules, each encoding a different sequence in the RBP landing site. This sequence is derived from a fragment of mRNA of a cell or tissue of interest. This library is then co-transfected with a reader of the epitranscriptomic mark fused to Adar. In this case, the cartoon shows the fusion of YTHDF, the reader of m6A methylation mark. Only the recorder molecules encoding the appropriate sequence or RNA modification, will recruit the RBP-Adar fusion and become edited.
Figure 6:
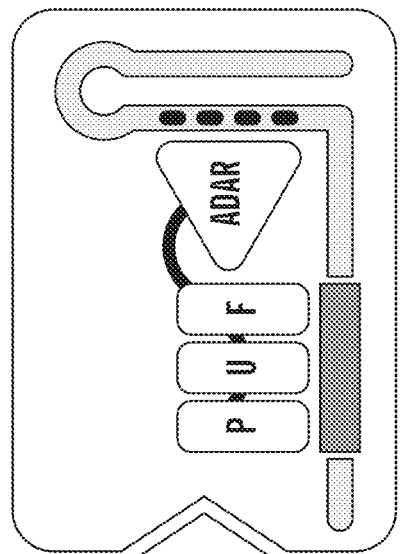

Usage of the interactome recorder system to determine the binding sites of a given RBP in the transcriptome (FIG. 6):

Once an RBP-Adar fusion has passed the quality controls for specificity, it can be determined what are its target mRNAs and where it binds in these RNAs. The technology described herein permits this determination to be done in vivo, and independent of antibodies and UV-mediated cross-linking, which is a significant improvement compared to prior art. In this instance, a library of recorder molecules can be created, where in lieu of the RBP-consensus binding site a fragment of the transcriptome of a cell or tissue of interest is cloned. To this end, total RNA is purified and polyadenylated RNA selected from the cell or tissue of interest and then fragmented randomly. After conversion of the fragments to cDNA, the pool of fragments is then clone into a plasmid vector encoding the recorder system. The entire library pool is amplified by PCR after cloning and then transcribed to RNA.

The selected RBP-Adar fusion is transfected in cells or zebrafish embryos together with the recorder library where each molecule contains a different fragment of mRNA from the cells or tissues of interest. Upon transfection and processing, only the recorder molecules containing a sequence that is conducive to the binding of the RBP will show some degree of editing. By analyzing the sites that accumulate more editings, the RBP binding sites in the transcriptome can be inferred.

Usage of the interactome recorder system to determine the sites modified with the epitranscriptomic methylation m6A:

For this application we will use YTHDF2, the RBP that recognizes and binds to RNAs modified with m6A. We fused YTHDF2 (or any of the other two paralogs, YTHDF1 and YTHDF3) to catalytic domain of ADAR. The substrate for this chimeric protein will be a library of fragments of the transcriptome of the cell or tissue of interest ligated to the recorder hairpin RNA and enzymatically capped. Each RNA molecule in this library of non-coding RNAs that contain a piece of cellular mRNA fused to the recorder hairpin. This approach will maintain intact all RNA modifications present in the original transcripts, including m6A. When we transfect in cells or zebrafish embryos the selected YTHDF2-Adar fusion together with the recorder library with transcriptome fragments, YTHDF2 will bind to the m6A-modified RNAs which will allow ADAR to modify the recorder RNA. We will sequence the library of recorder RNAs to identify which fragments directed the editing and identify m6A sites. The proportion of RNA molecules containing a m6A sites whose recorder is edited versus non-edited, will allow us to calculate, for first time, the percentage of modification at any given sites. This will be extremely useful to monitor changes on the levels m6A modifications that are at the basis of certain cancers and neurological disorders.

Figure 7:
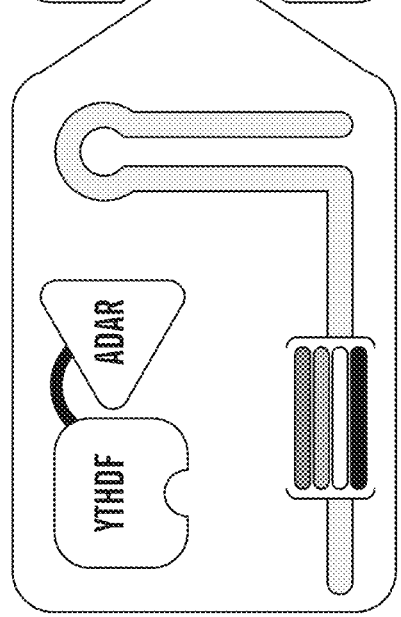
FIG. 7 depicts a schematic of the concept of how interactome recorder can be used to engineer designer proteins. These proteins are artificial modular proteins build with the aggregation of different RNA-binding domains, usually based on the domains from Pumillio protein, the Puf domain. Each domain recognizes and binds to a single nucleotide, and a single protein contains and array of up to 8 of these domains. This embodiment of the technology combines the expression of recorder mRNA with a target sequence of interests together with a library of randomly-assembled PUF domains arrays fused to the catalytic domain of an RNA-editing enzyme like Adar. In this case, the EYFP encoded in the recorder is substituted by the array of PUF domains, so long-read sequencing determine if a certain PUF array was able to bind to the target site and edit the recorder. This approach will permit identification of artificial chimeric proteins that bind to mRNA sequences of interest.
Figure 7:
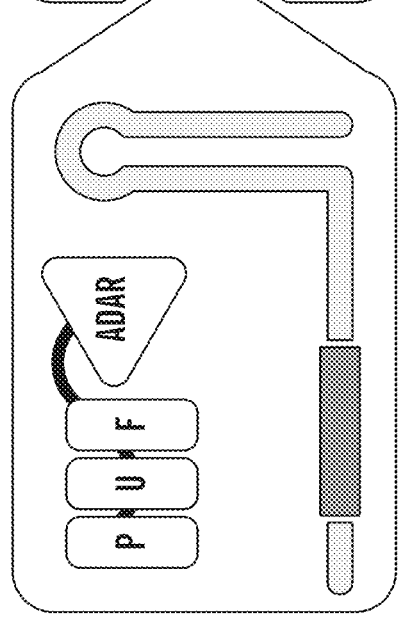

Usage of the interactome recorder system to engineer designer proteins (FIG. 7). These proteins are artificial modular proteins built with the aggregation of different RNA-binding domains, usually based on the domains from Pumillio protein, the Puf domain. Each domain recognizes and binds to a single nucleotide, and a single protein contains an array of up to 8 of these domains. The technology described herein combines the expression of recorder mRNA with a target sequence of interest together with a library of randomly-assembled PUF domains arrays fused to the catalytic domain of an RNA-editing enzyme like Adar. In this case, the EYFP encoded in the recorder will be substituted with the array of PUF domains, so long-read sequencing will permit determination of whether a certain PUF array was able to bind to the target site and edit the recorder. This approach will permit identification of artificial chimeric proteins that bind to mRNA sequences of interest.

Figure 8A:
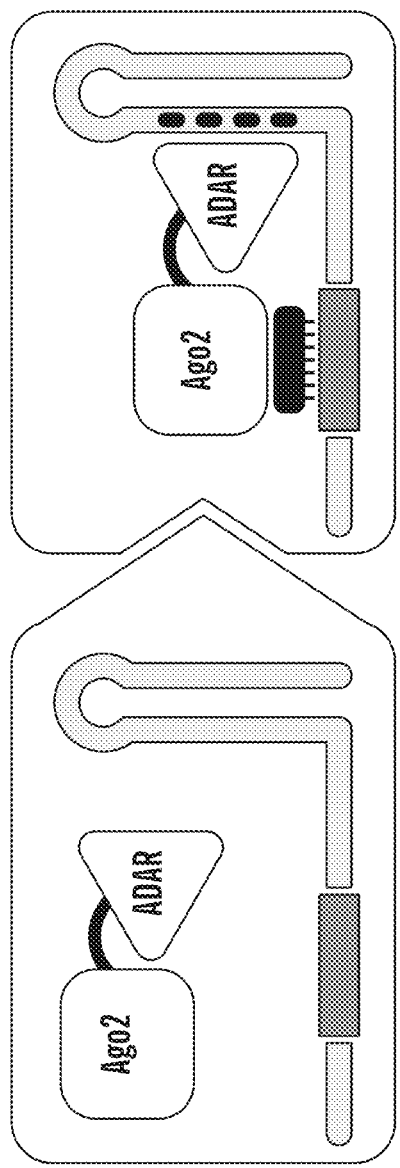
FIG. 8A depicts a schematic of the concept of how interactome recorder can be used to determine microRNA activity in vivo. In this case, the writer comprises a protein fusion between a protein from the Argonaute family and the catalytic domain of the RNA-editing enzyme ADAR. The recorder must contain the target site of the microRNA of interest, usually the 6 to 8 nucleotides complementary to the miRNA seed region. In the presence of the writer, the recorder and the miRNA of interest, the ternary interaction is recorded as RNA editing in the recorder mRNA. The number of edits will be proportional to the strength of the microRNA-target site interaction. Other variants of this approach include expressing the Ago-Adar writer together with a library of recorders that containing all possible 8-nucleotide sequences as binding site. Only the recorder molecules containing sites complementary to the microRNA will be edited if the microRNA is present, helping with the identification of miRNA preferred sites or the identification of which microRNAs are present in the cell.
Figure 8B:
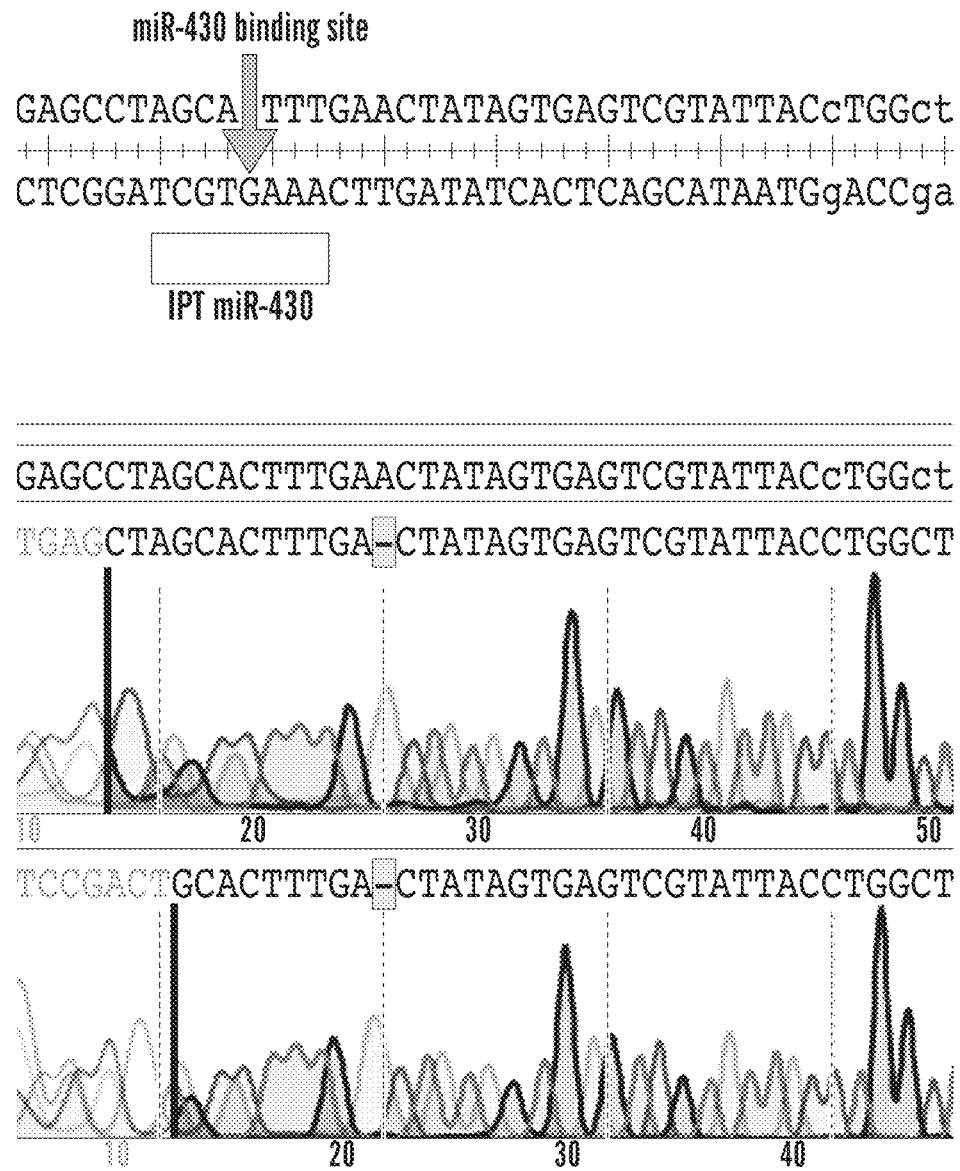
FIG. 8B depicts data from interactome recorder with Ago2 and the microRNA miR-430. Only in the presence of the miR-430 target site and miR-430 microRNA, is editing of the recorder seen. The editing is shown in the Sanger sequencing trace by a double peak of adenine and guanosines at the indicated positions. The higher the guanosine peak, the higher the editing.
Figure 8B:
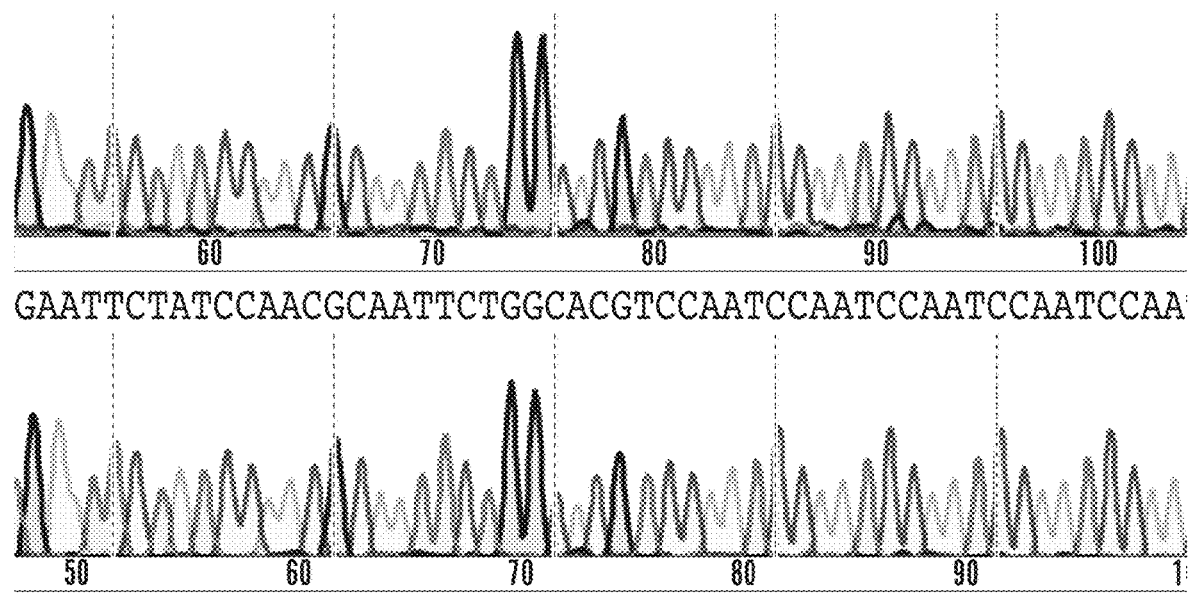
Figure 8B:
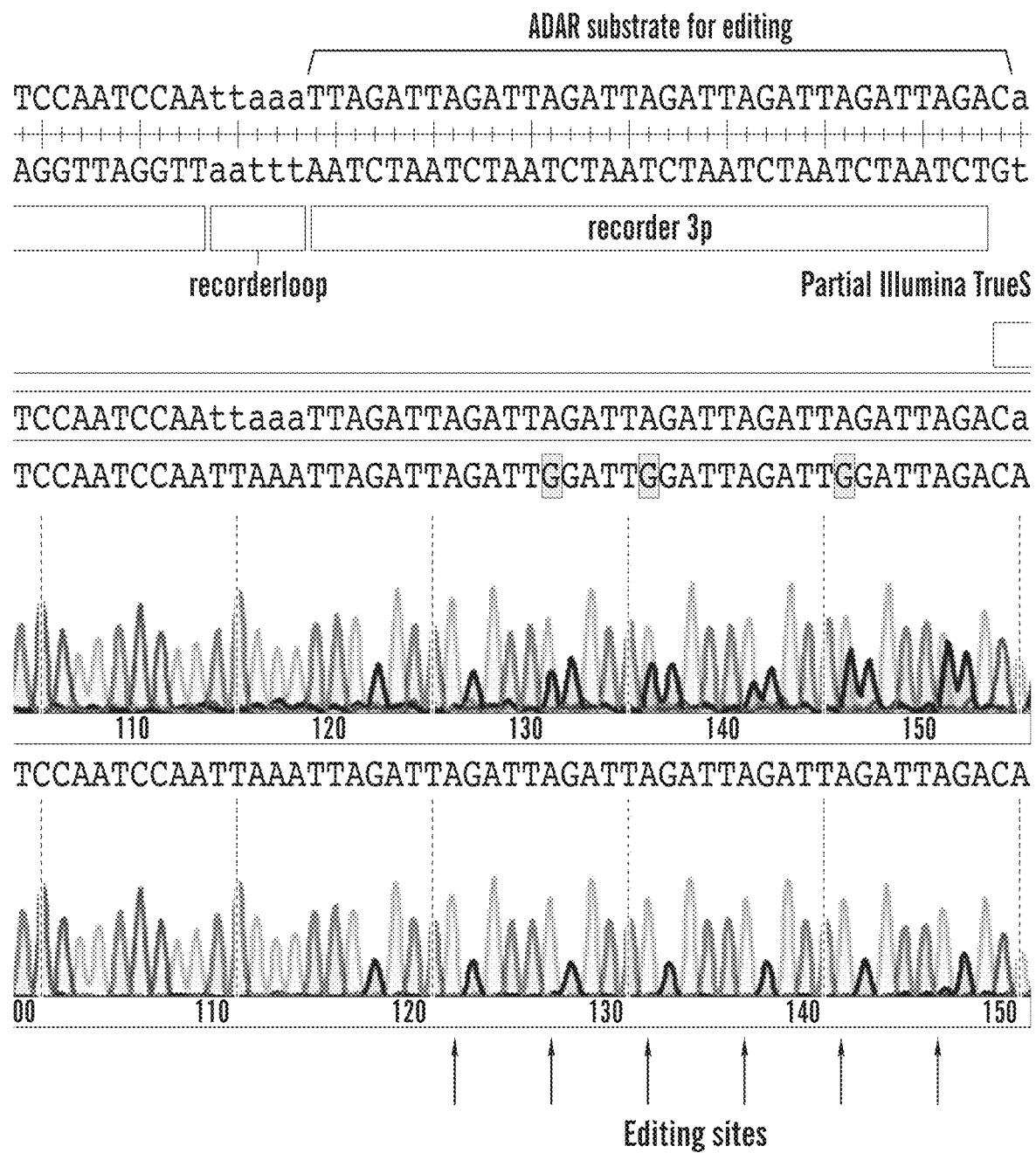
Figure 9A:
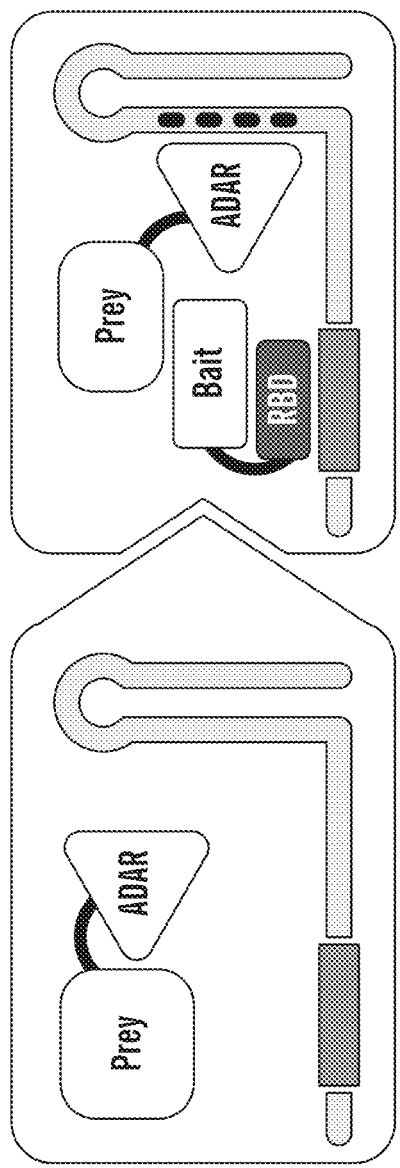
FIG. 9A depicts a schematic of the concept of how interactome recorder can be used to determine protein-protein interactions in vivo. One of the proteins of interest is fused to an RNA-binding domain peptide, while the other protein is fused to ADAR catalytic domain. The editing of the recorder will be possible only when both proteins interact in vivo, because it will bring together the recorder RNA and the ADAR catalytic domain.
Figure 9B:
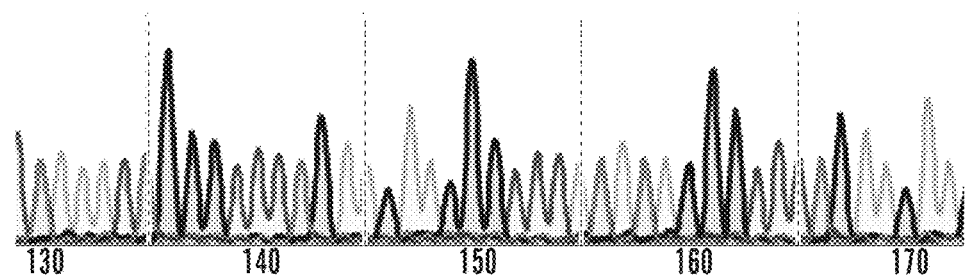
FIG. 9B depicts data from interactome recorder detecting the interaction between GFP and a nanobody against GFP. The GFP is tethered to the recorder via the lambda peptide that recognizes the BBox RNA hairpin cloned in the recorder portion of the reporter. The expression of GFP and GFP nanobody leads to the editing of the recorder. The editing is show in the Sanger sequencing trace by a double peak of adenine and guanosines at the indicated positions. The higher the guanosine peak, the higher the editing.
Figure 9B:
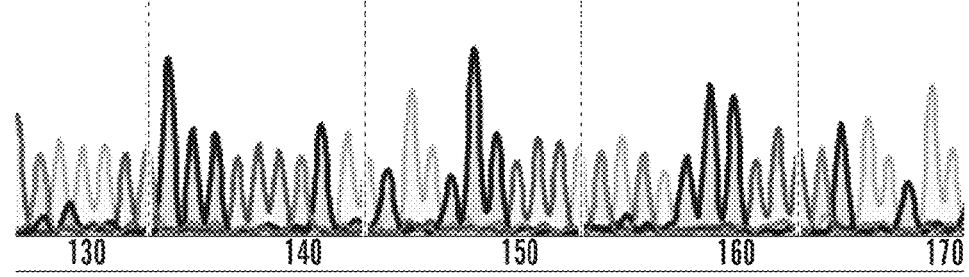
Figure 9B:
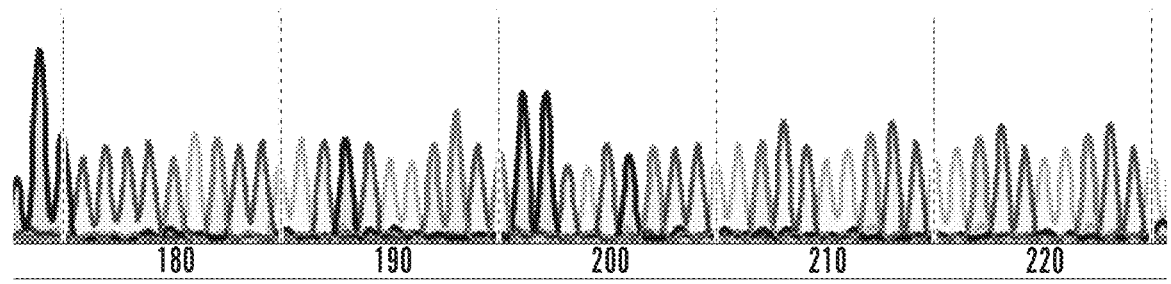
Figure 9B:
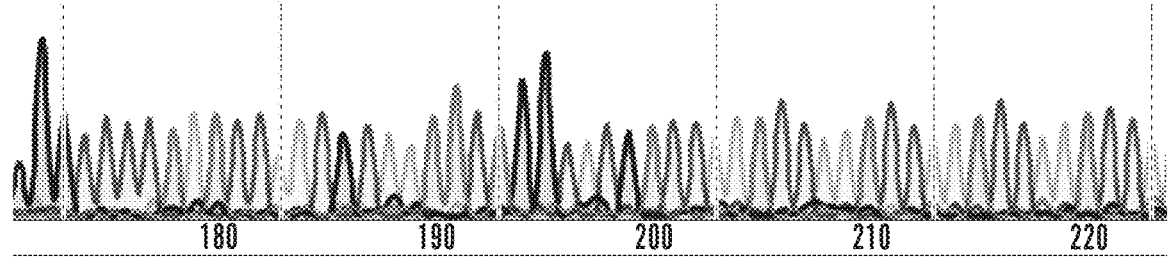

Usage of the interactome recorder system to determine microRNA activity in vivo (FIG. 8A). In this case, the writer comprises a protein fusion between a protein from the Argonaute family and the catalytic domain of the RNA-editing enzyme ADAR. The recorder must contain the target site of the microRNA of interest, usually the 6 to 8 nucleotides complementary to the miRNA seed region. In the presence of the writer, the recorder and the miRNA of interest, the ternary interaction is recorded as RNA editing in the recorder mRNA. The number of edits will be proportional to the strength of the microRNA-target site interaction. Other variants of this approach include expressing the Ago-Adar writer together with a library of recorders that containing all possible 8-nucleotide sequences as binding site. Only the recorder molecules containing sites complementary to the microRNA will be edited if the microRNA is present, helping with the identification of miRNA preferred sites or the identification of which microRNAs are present in the cell.

Usage of the interactome recorder system to determine protein-protein interactions in vivo (FIG. 9). One of the proteins of interest is fused to an RNA-binding domain peptide, while the other protein is fused to ADAR catalytic domain. The recorder will contain an RNA landing site that is recognized and bound by the RNA-binding domain fused to the protein of interest. The pair of RNA-protein interactors used here to tether the protein of interest to the recorder RNA can be the BBox hairpin and lambda peptide. The editing of the recorder will be possible only when both proteins interact in vivo, because it will bring together the recorder RNA and the ADAR catalytic domain.

Figure 10:
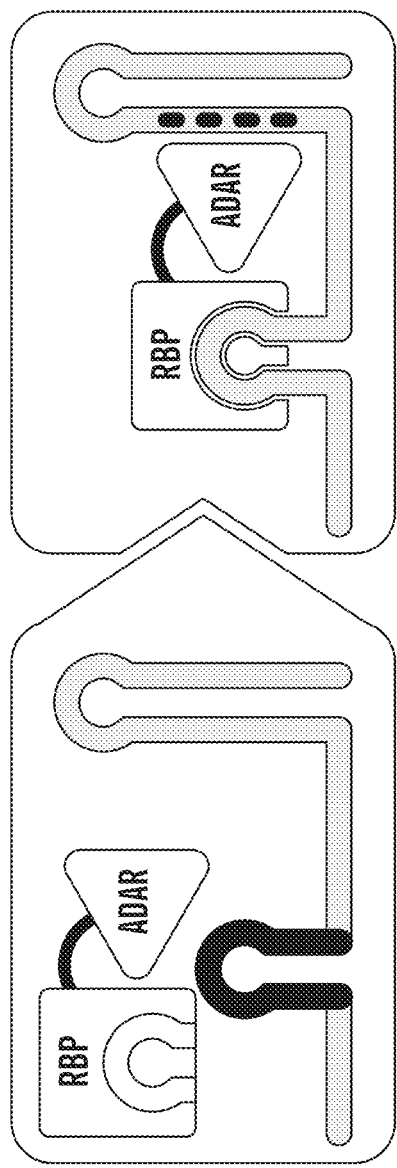
FIG. 10 depicts a schematic of the concept of how interactome recorder can be used to determine the structural determinants of the interaction between an RNA-binding protein and a structured target. The RNA-binding protein is fused to the catalytic subunit of the RNA-editing enzyme Adar to generate the writer component of the reporter. Then a structured RNA is cloned as the RNA-binding site in the recorder. RNA editing of the recorder will be observed after sequencing it only if the RNA structure and sequence are conducive to the RNA-protein interaction. A variation of this assay will interrogate a library of structures embedded in the recorder for their ability to recruit the RNA-binding protein of interest. Only those structures that interact with the RNA-binding protein will induce RNA editing of the recorder.

Usage of the interactome recorder system to determine the structural determinants of the interaction between an RNA-binding protein and a structured target (FIG. 10). The RNA-binding protein is fused to the catalytic subunit of the RNA-editing enzyme Adar to generate the writer component of the reporter. Then a structured RNA is cloned as the RNA-binding site in the recorder. RNA editing of the recorder will be observed after sequencing it only if the RNA structure and sequence are conducive to the RNA-protein interaction. A variation of this assay will interrogate a library of structures embedded in the recorder for their ability to recruit the RNA-binding protein of interest. Only those structures that interact with the RNA-binding protein will induce RNA editing of the recorder.

Figure 11:
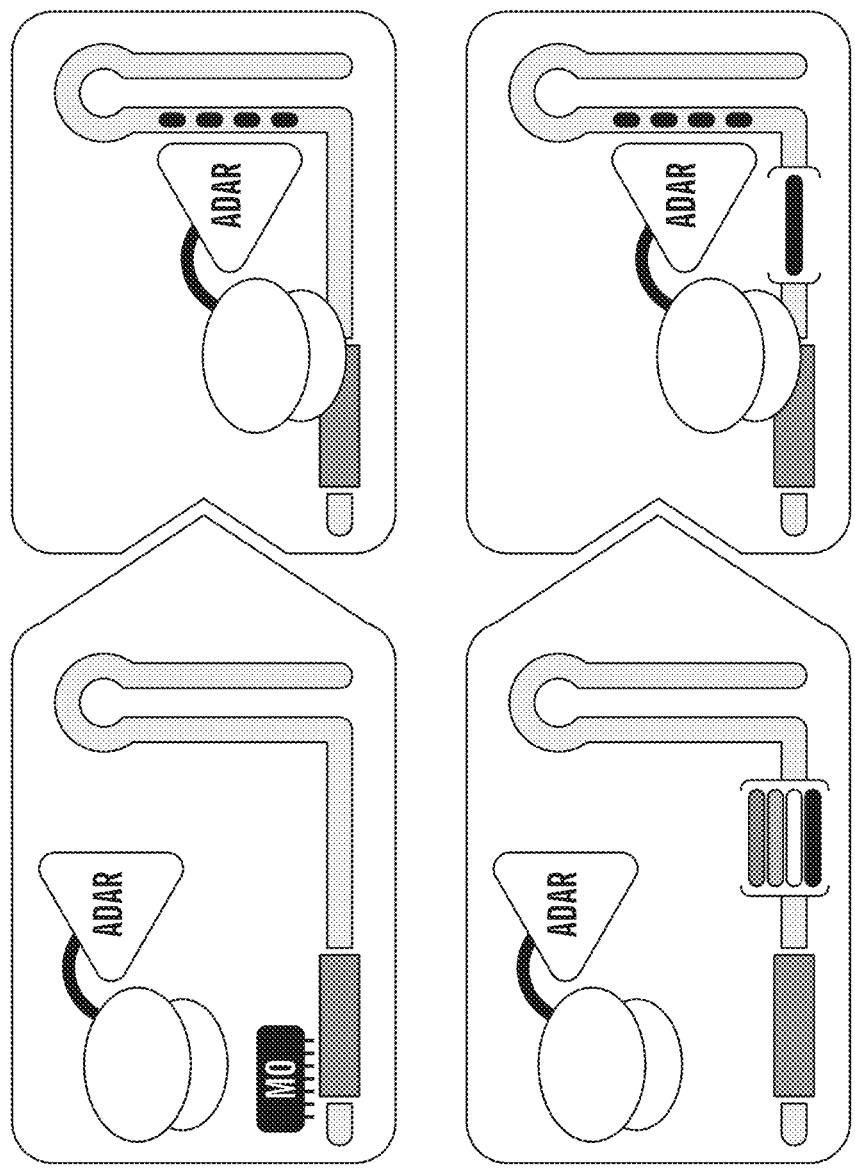
FIG. 11 depicts a schematic of the concept of how interactome recorder can be used to determine translation efficiency. The assay comprises creating a protein fusion between an endogenous ribosomal protein or translation factor or termination factor and the catalytic domain of the RNA-editing enzyme Adar. This chimeric protein constitutes the writer portion of the reporter. In addition, the recorder is generated by encoding the gene of interest for which it is desired to determine its translation efficiency with the perfect Adar substrate hairpin at its 3' UTR. Once the dual reporter system of writer and recorder are coexpressed in the cell, editing on the recorder will only be detected via sequencing only if the gene encoded in the recorder is translated. The editing of the recorder will be directly proportional to the level of translation. Specificity of the editing due to translation can be tested by blocking translation of the recorder with antisense modified oligonucleotides or morpholinos. A variant of this assay interrogates a library of elements for enhancers or repressors of translation. These sequence elements are cloned downstream a fixed coding sequence and before the Adar substrate. The editing of the recorder will increase or decreased from a basal level depending on the effect of the sequence elements on translation.

Usage of the interactome recorder system to determine translation efficiency (FIG. 11). This assay comprises creating a protein fusion between an endogenous ribosomal protein and the catalytic domain of the RNA-editing enzyme Adar. This chimeric protein constitutes the writer portion of the reporter. In addition, the recorder is generated by encoding the gene of interest for which it is desired to determine its translation efficiency with the perfect Adar substrate hairpin at its 3' UTR. Once the dual reporter system of writer and recorder are coexpressed in the cell, editing on the recorder will be detected via sequencing only if the gene encoded in the recorder is translated. The editing of the recorder will be directly proportional to the level of translation. Specificity of the editing due to translation can be tested by blocking translation of the recorder with antisense modified oligonucleotides or morpholinos. A variant of this assay interrogates a library of elements for enhancers or repressors of translation. These sequence elements are cloned downstream a fixed coding sequence and before the Adar substrate. The editing of the recorder will increase or decreased from a basal level depending on the effect of the sequence elements on translation.

Figure 12:
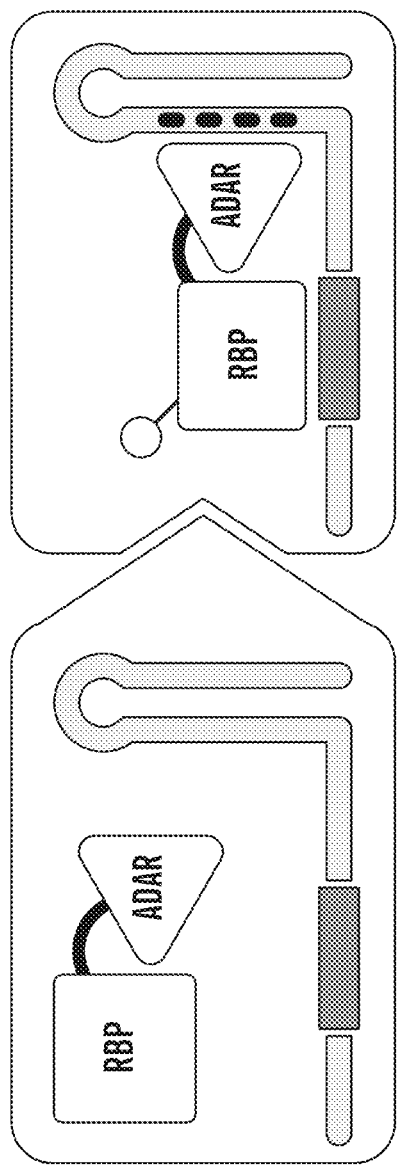
FIG. 12 depicts a schematic of the concept of how interactome recorder can be used to determine how post-translational modifications (PTMs) of RNA-binding proteins can modulate their activity. PTMs include but are not restricted to phosphorylation, SUMOylation, acetylation, methylation, etc. A RNA-binding protein of interest is mutated to mimic or preclude PTMs, and it is fused to the Adar catalytic domain. When this chimeric protein is co-expressed with the recorder RNA, the editing of the recorder RNA will only occur if the PTM modification of the RNA-binding protein is conducive to facilitate RNA-protein interactions.

Usage of the interactome recorder system to determine how post-translational modifications (PTMs) modulate RNA-binding protein activity (FIG. 12). PTMs include but are not restricted to phosphorylation, SUMOylation, acetylation, methylation, etc. A RNA-binding protein of interest is mutated to mimic or preclude PTMs, and it is fused to the Adar catalytic domain. When this chimeric protein is co-expressed with the recorder RNA, the editing of the recorder RNA will only occur if the PTM modification of the RNA-binding protein is conducive to facilitate RNA-protein interactions.

Possible Variations

The exemplary interactome recorders presented here are based on the fusion between an RNA binding protein and the catalytic domain of Adar. In some instances, it will be necessary to use a mutant version of Adar with the E488Q mutation that increases the catalytic rate. Other mutations known in the art or described elsewhere herein can be used in alternative embodiments. The interactome recorder is based on RNA editing, and as such, in principle any RNA-editing enzyme like (but not limited to) APOBEC could be used in lieu of ADAR. When the writer comprises ADAR, the recorder that can comprise an optimal substrate for ADAR. ADAR substrate preferences are well stablished in the public scientific literature and different sequence and structural variations can be designed. If a different RNA-editing enzyme were to be used instead of ADAR, the sequence of the recorder should be adapted to the substrate requirements of the new RNA-editing enzyme.

Example 2

The technology described herein is referred to at times as an "Interactome Recorder." The Interactome Recorder system comprises a writer and a recorder.

Figure 13A:
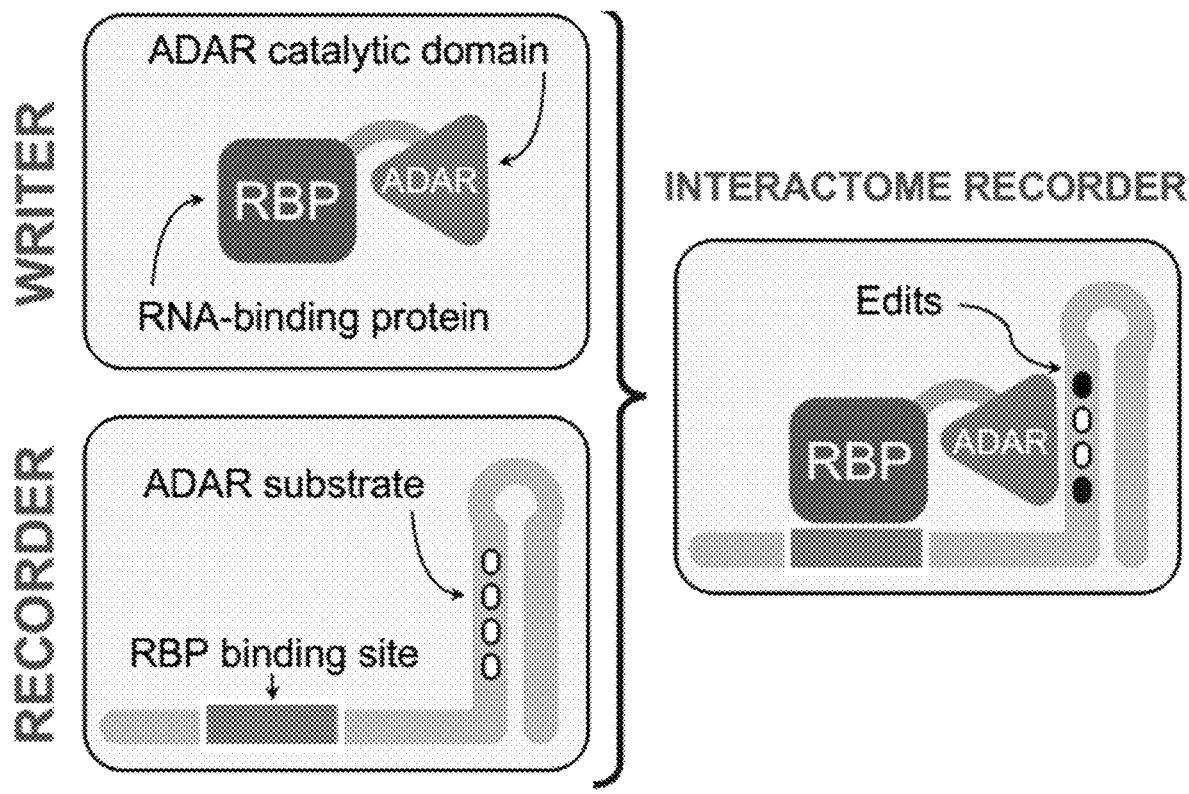
FIGS. 13A-13B depict schematics describing the components of an exemplary embodiment.
Figure 13B:
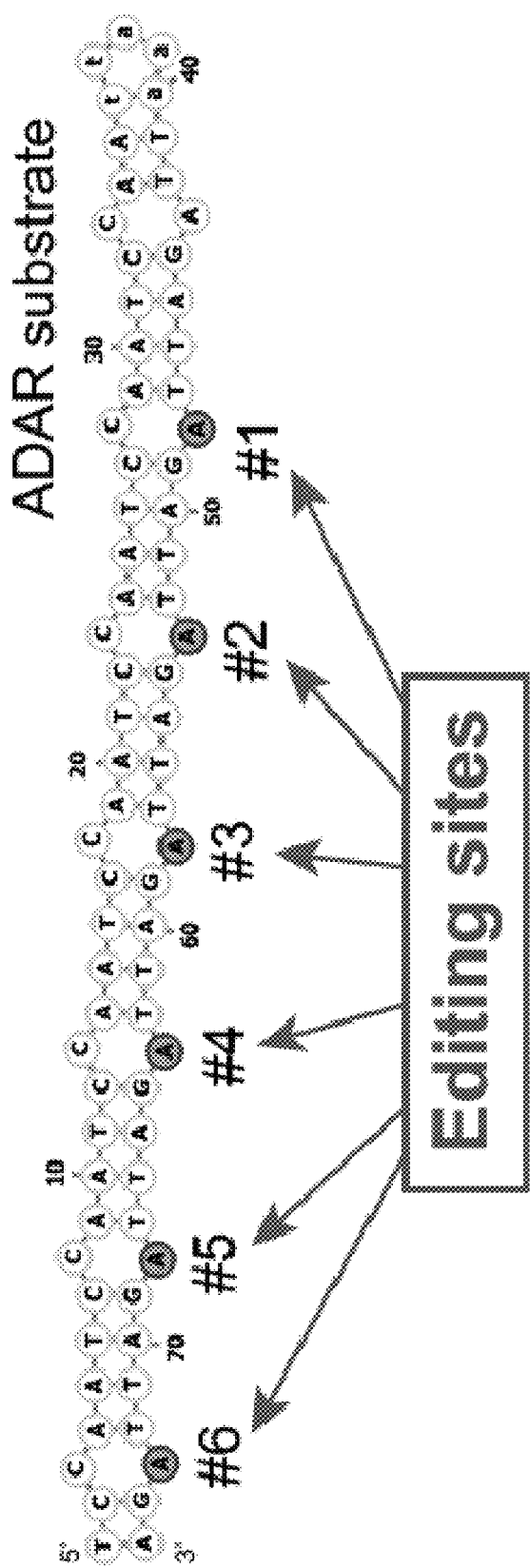

In some embodiments, only when both components are brought together via the interaction between an RNA-binding domain of a protein and a RNA motif, is editing of the Adar substrate observed (FIG. 13A). The editing comprises A-to-G mutations in the sequence of the Adar substrate.

Figure 14:
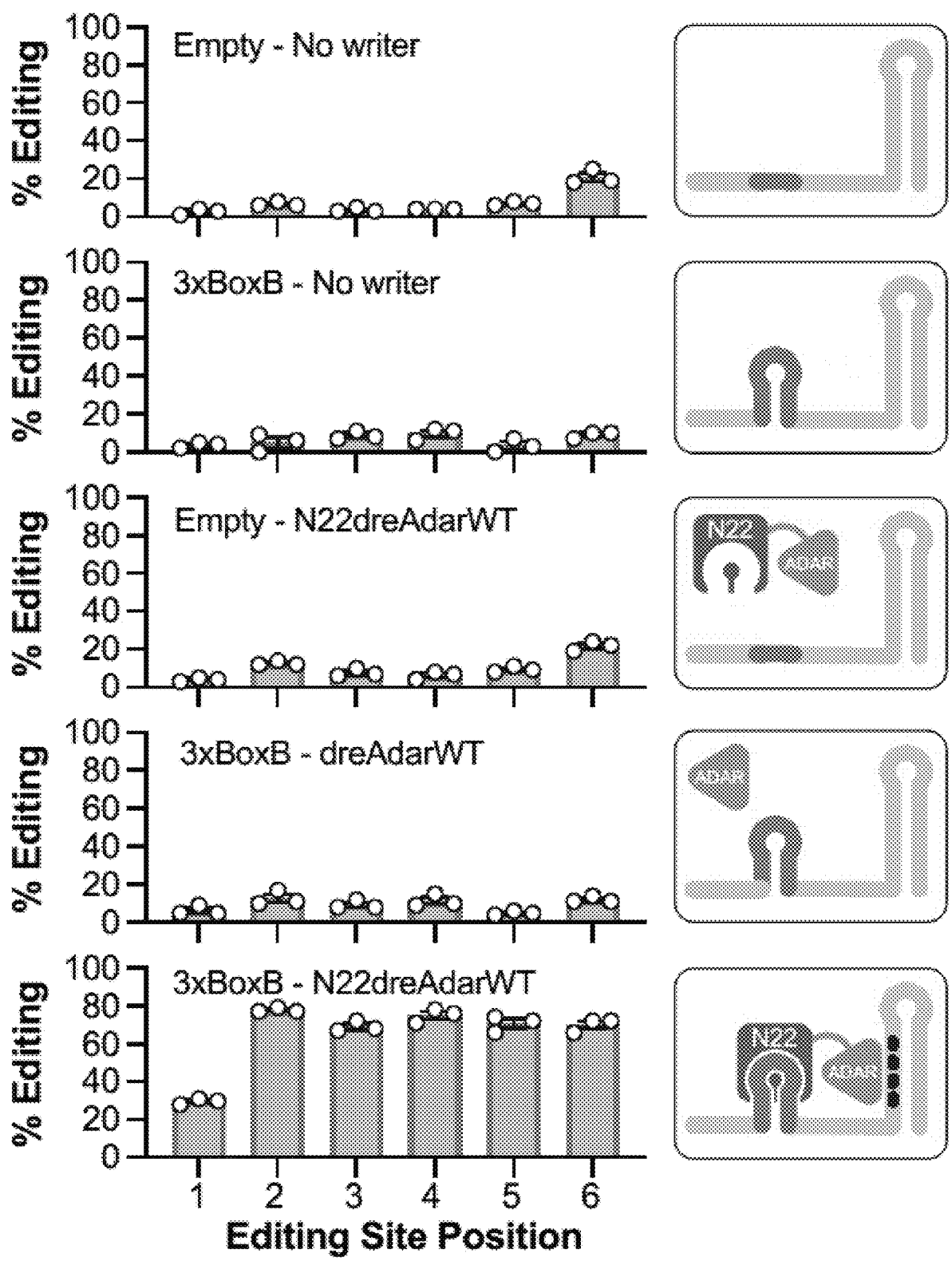
FIG. 14 depicts proof of specificity. To demonstrate the specificity of the Interactome Recorder, the interaction of a well-known protein-RNA pair was tested: BoxB RNA and lambda N22 peptide. There recorder alone, with or without the BoxB site, it is not edited. Similarly, Adar alone or N22 fused to Adar but in absence of BoxB can not edit the recorder. Only when N22-Adar is expressed in the same cell as the recorder with the BoxB, was editing observed in all sites. The bar plots indicate the % of editing of each site in the recorder. This experiment is performed in zebrafish embryos. N22dreAdarWt: lambda N22 peptide fused to wild-type Adar catalytic subunit from zebrafish (*Danio rerio*).

The systems described herein are specific in their activity. To demonstrate the specificity of the Interactome Recorder, the interaction of a well-known protein-RNA pair was tested: BoxB RNA and lambda N22 peptide. There recorder alone, with or without the BoxB site, it is not edited. Similarly, Adar alone or N22 fused to Adar but in absence of BoxB can not edit the recorder. Only when N22-Adar is expressed in the same cell as the recorder with the BoxB, was editing observed in all sites (FIG. 14).

Figure 15:
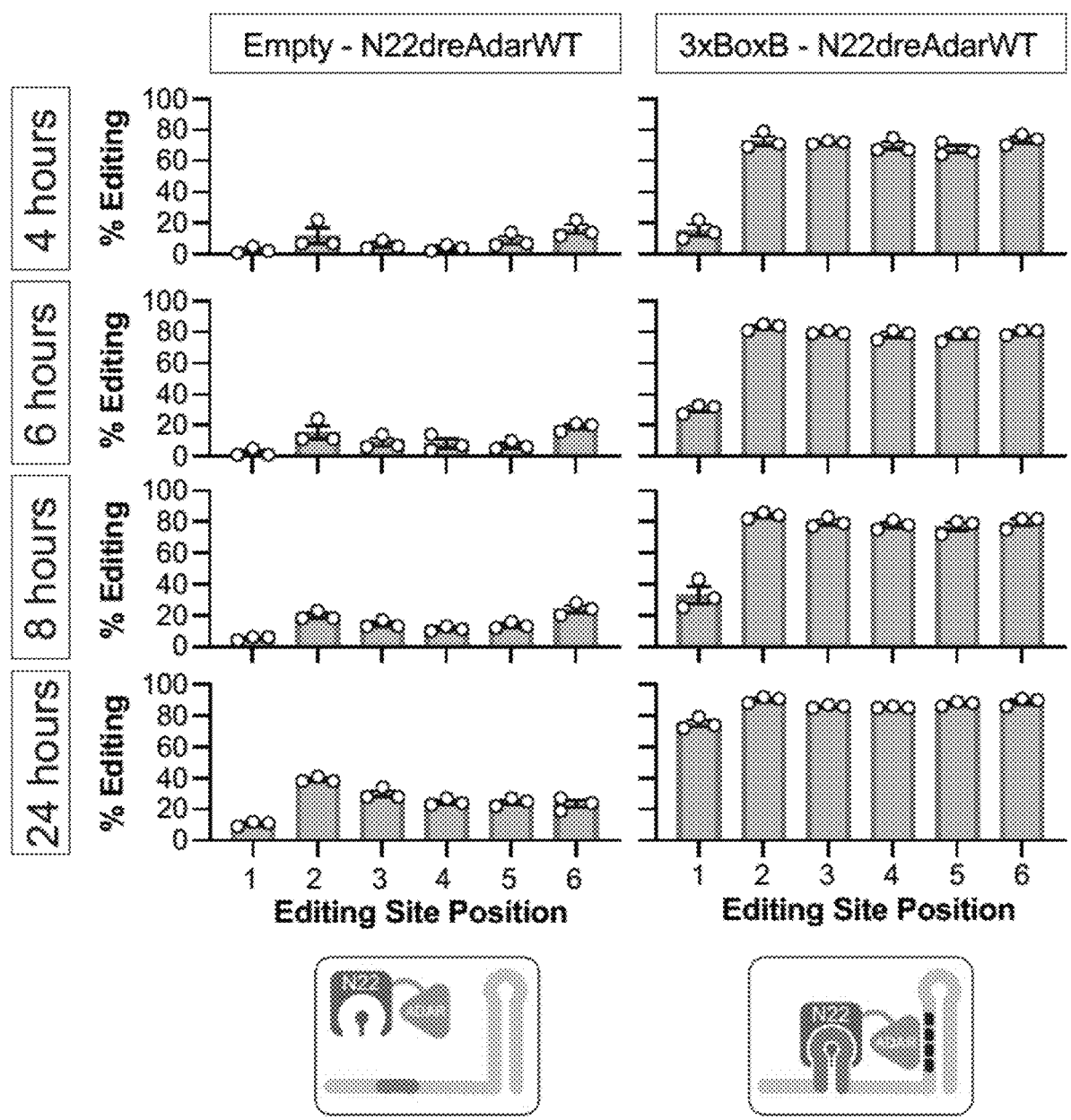
FIG. 15 depicts a time course. The amount of editing of the recorder triggered by the BoxB-N22Adar interaction in increasing incubation times was determined. Editing of the reporter occurs as early as 4 hours after injection. Editing of the control without BoxB binding site remains low, only increasing after 24 hours. The bar plots indicate the % of editing of each site in the recorder. This experiment is performed in zebrafish embryos. N22dreAdarWt: lambda N22 peptide fused to wild-type Adar catalytic subunit from zebrafish (*Danio rerio*).
Figure 16:
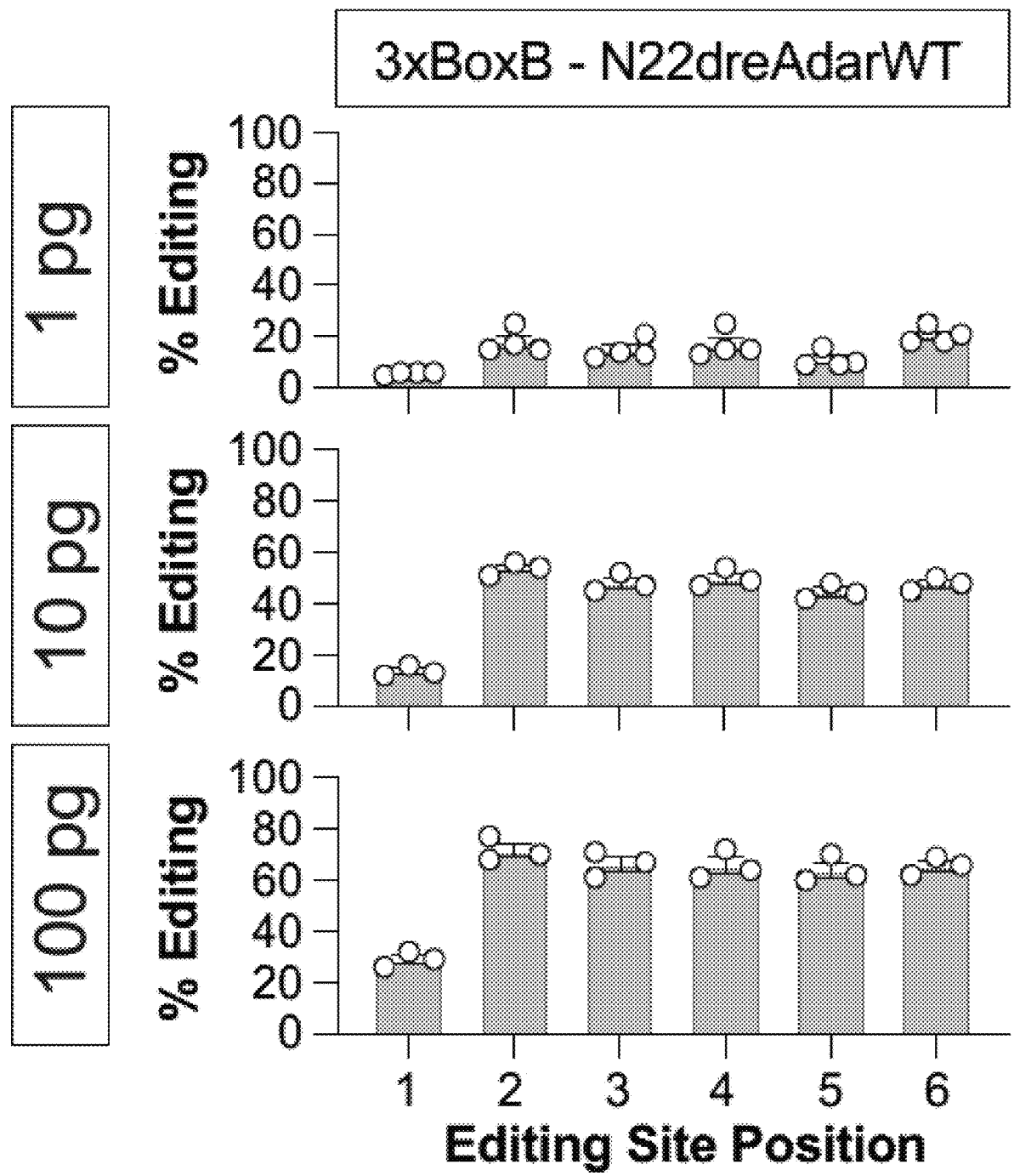
FIG. 16 depicts a dose response. The amount of editing of the recorder triggered by the BoxB-N22Adar interaction in increasing doses of the N22-Adar fusion was determined. Editing of the reporter occurs with as little as 10 pg of N22-Adar mRNA injected per zebrafish embryo. The bar plots indicate the % of editing of each site in the recorder. This experiment is performed in zebrafish embryos. N22dreAdarWt: lambda N22 peptide fused to wild-type Adar catalytic subunit from zebrafish (*Danio rerio*).

Editing of the reporter occurs as early as 4 hours after injection (FIG. 15). Editing of the control without BoxB binding site remains low, only increasing after 24 hours. Editing of the reporter occurs with as little as 10 pg of N22-Adar mRNA injected per zebrafish embryo (FIG. 16).

Figure 17:
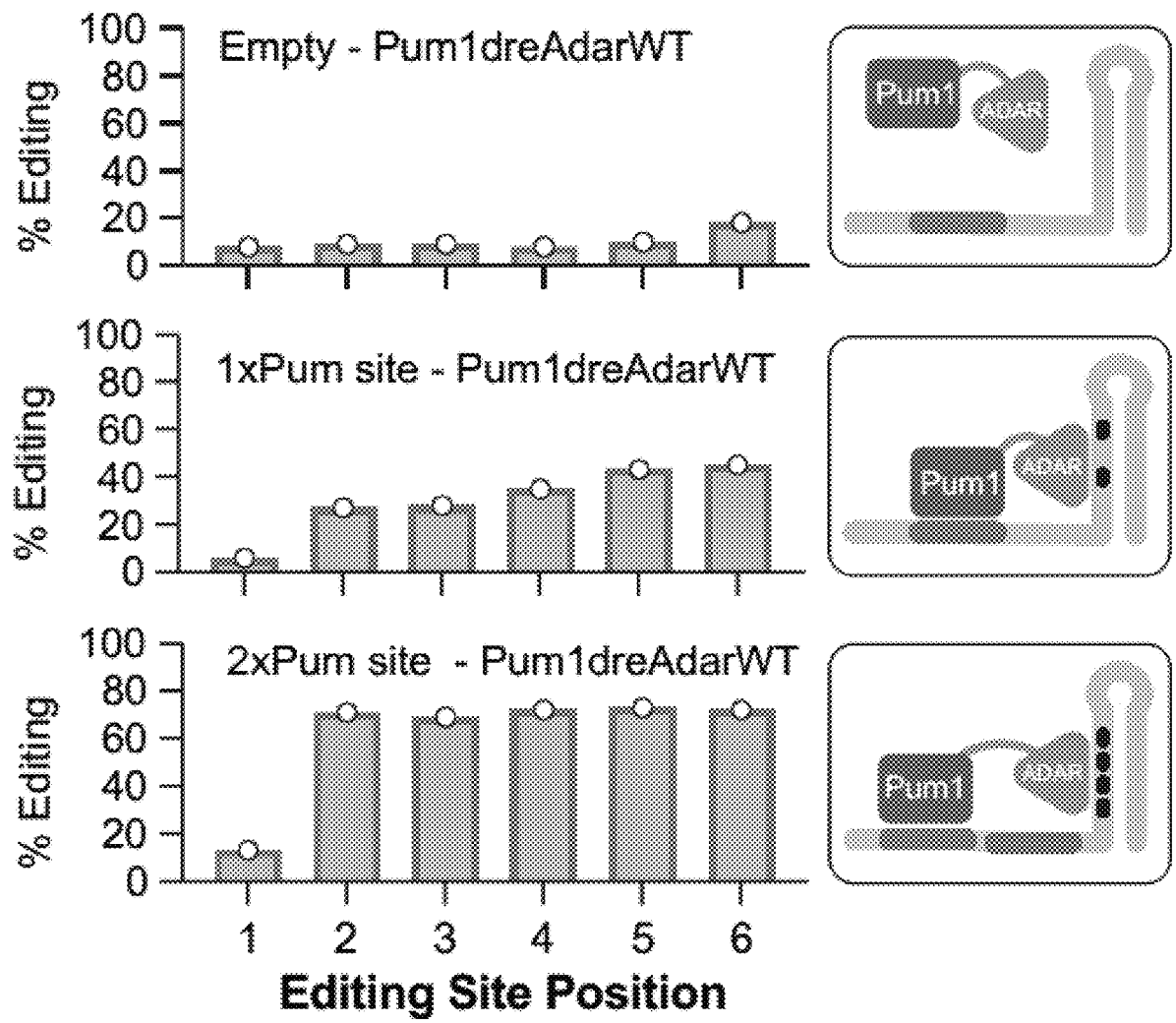
FIG. 17 depicts a dynamic range. It was tested whether increasing the number of binding sites in the recorder mRNA does increase editing of the recorder. Pumilio fused to Adar (Pum1dreAdarWT) was co-injected with a recorder that contains 0, 1 or 2 binding sites for Pumilio. Editing of the recorder increases proportionally with the number of Pumillio binding sites embedded in the recorder. The bar plots indicate the % of editing of each site in the recorder. This experiment is performed in zebrafish embryos.

Pumilio fused to Adar (PumldreAdarWT) was co-injected with a recorder that contains 0, 1 or 2 binding sites for Pumilio. Editing of the recorder increases proportionally with the number of Pumillio binding sites embedded in the recorder (FIG. 17).

Figure 18:
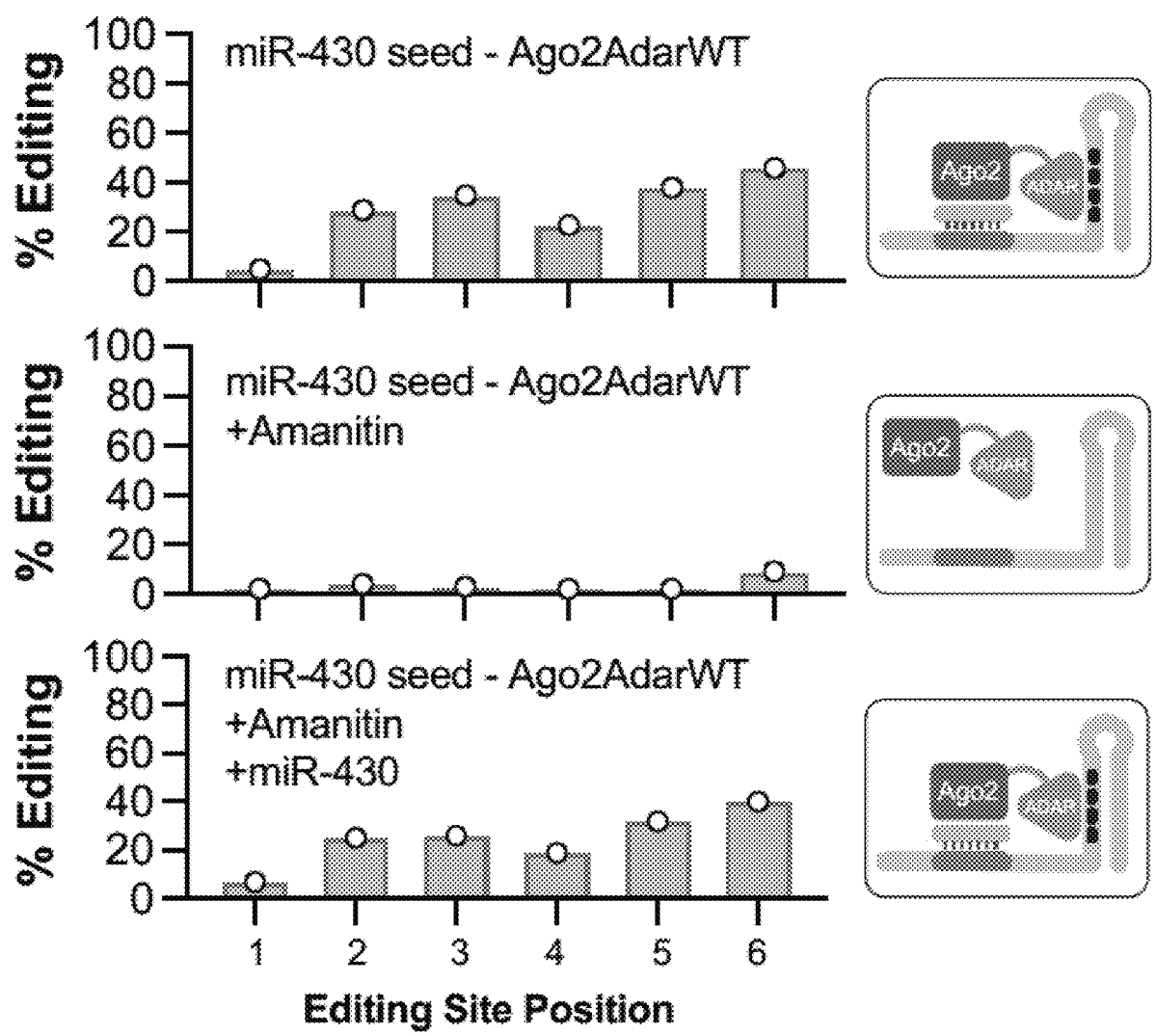
FIG. 18 depicts a microRNA sensor. miR-430 is a small non-coding regulatory microRNA that recognize their targets mRNAs trough interaction and pairing. miR-430 binds to the effector protein Ago2 and together form a riboprotein complex that recognizes and binds to target mRNAs. miR-430 is the only microRNA expressed during early embryogenesis. Injection of alpha-Amanitin prevents its expression. A sensor of microRNA activity was generated by fusing Ago2 to Adar catalytic subunit. Only with the tertiary interaction between Ago2, a microRNA, and the target is reconstituted, is editing detected. After injection of the interactome recorder in zebrafish embryos, editing occurs in wild-type embryos but not when endogenous miR-430 expression is inhibited by alpha-Amanitin. However, editing can be restored by injection and providing miR-430 exogenously.

The technology described herein can be used to detect microRNAs. miR-430 is a small non-coding regulatory microRNA that recognize their targets mRNAs trough interaction and pairing. miR-430 binds to the effector protein Ago2 and together form a riboprotein complex that recognizes and binds to target mRNAs. miR-430 is the only microRNA expressed during early embryogenesis. Injection of alpha-Amanitin prevents its expression. A sensor of microRNA activity was generated by fusing Ago2 to Adar catalytic subunit. Only with the tertiary interaction between Ago2, a microRNA, and the target is reconstituted, is editing detected. After injection of the interactome recorder in zebrafish embryos, editing occurs in wild-type embryos but not when endogenous miR-430 expression is inhibited by alpha-Amanitin. However, editing can be restored by injection and providing miR-430 exogenously (FIG. 18).

Figure 19:
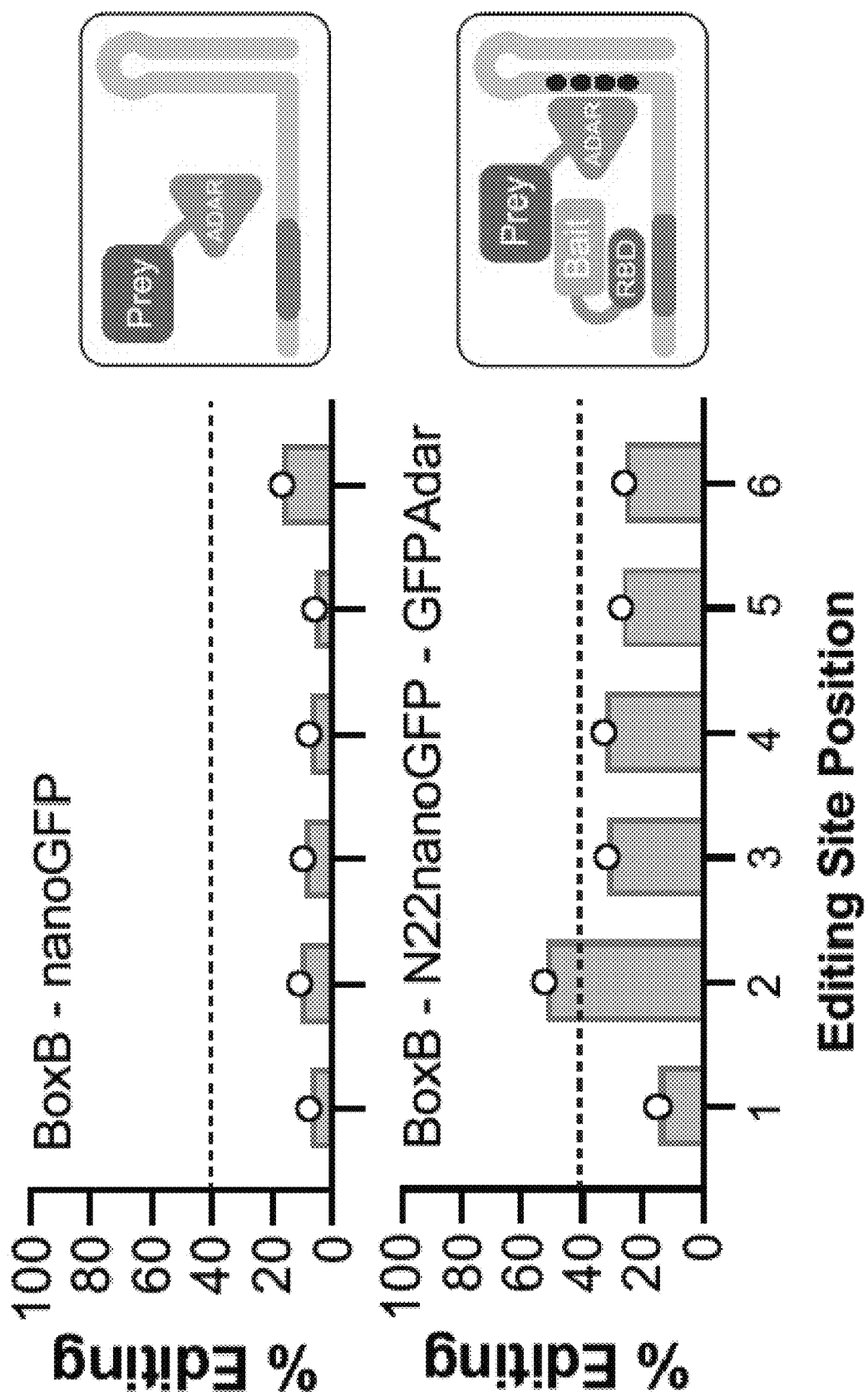
FIG. 19 depicts a protein-protein interaction sensor. In this scenario, the recorder and the catalytic subunit of Adar are bought in close proximity via the interaction of a pair of bait-prey proteins. The bait protein is tethered to the recorder RNA via a BoxB-N22 interaction. Only when the bait and prey proteins interact, is there editing of the recorder mRNA. This experiment is performed in zebrafish embryos.

The technology described herein can be used to detect protein-protein interactions. In this scenario, the recorder and the catalytic subunit of Adar are bought in close proximity via the interaction of a pair of bait-prey proteins. The bait protein is tethered to the recorder RNA via a BoxB-N22 interaction. Only when the bait and prey proteins interact, is there editing of the recorder mRNA (FIG. 19).

Figure 20:
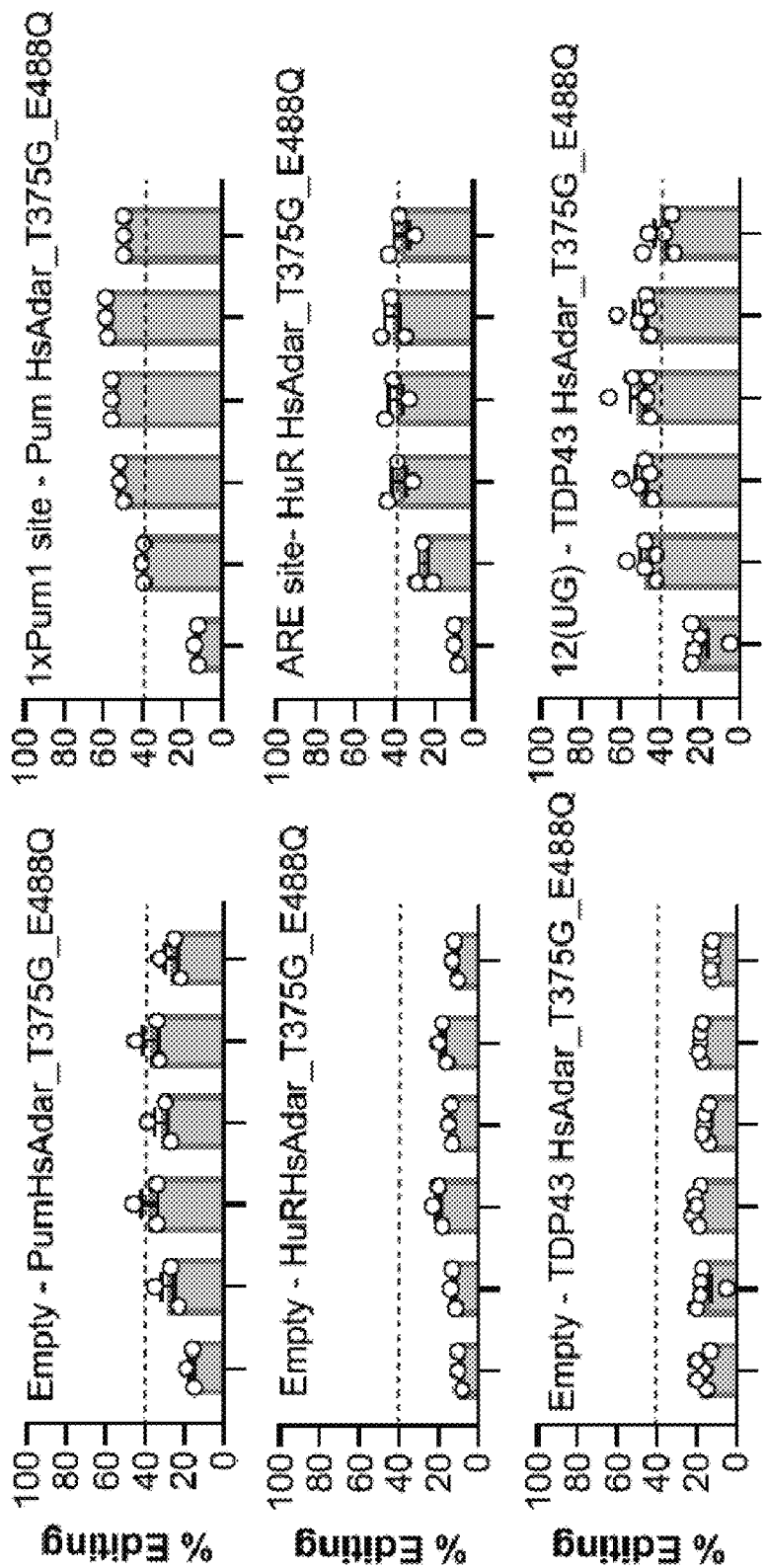
FIG. 20 demonstrates sensing RNA-binding proteins in human cells. Three RNA-binding proteins (Pumilio, Hur, and TDP-43) were fused to the catalytic subunit of Adar and their capacity to bind and edit the recorder in human cell tested. Adar contains two mutations (5F75F, E488Q) designed to maximize activity while minimizing background. In all three cases, more editing is observed when the RBP-Adar fusion is co-transfected with a recorder containing the correct RBP binding site in human HEK 293 cells.
Figure 20:
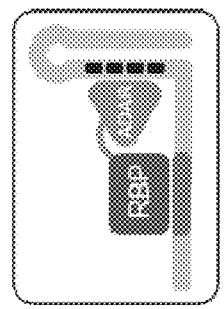
Figure 20:
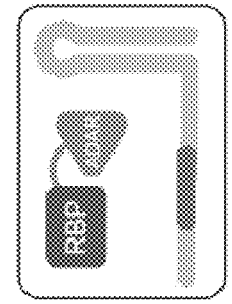

The technology described herein can be used to detect RNA-binding proteins in human cells. Three RNA-binding proteins (Pumilio, Hur, and TDP-43) were fused to the catalytic subunit of Adar and their capacity to bind and edit the recorder in human cell tested. Adar contains two mutations (T375G, E488Q) designed to maximize activity while minimizing background. In all three cases, more editing is observed when the RBP-Adar fusion is co-transfected with a recorder containing the correct RBP binding site in human HEK 293 cells (FIG. 20).

Figure 21:
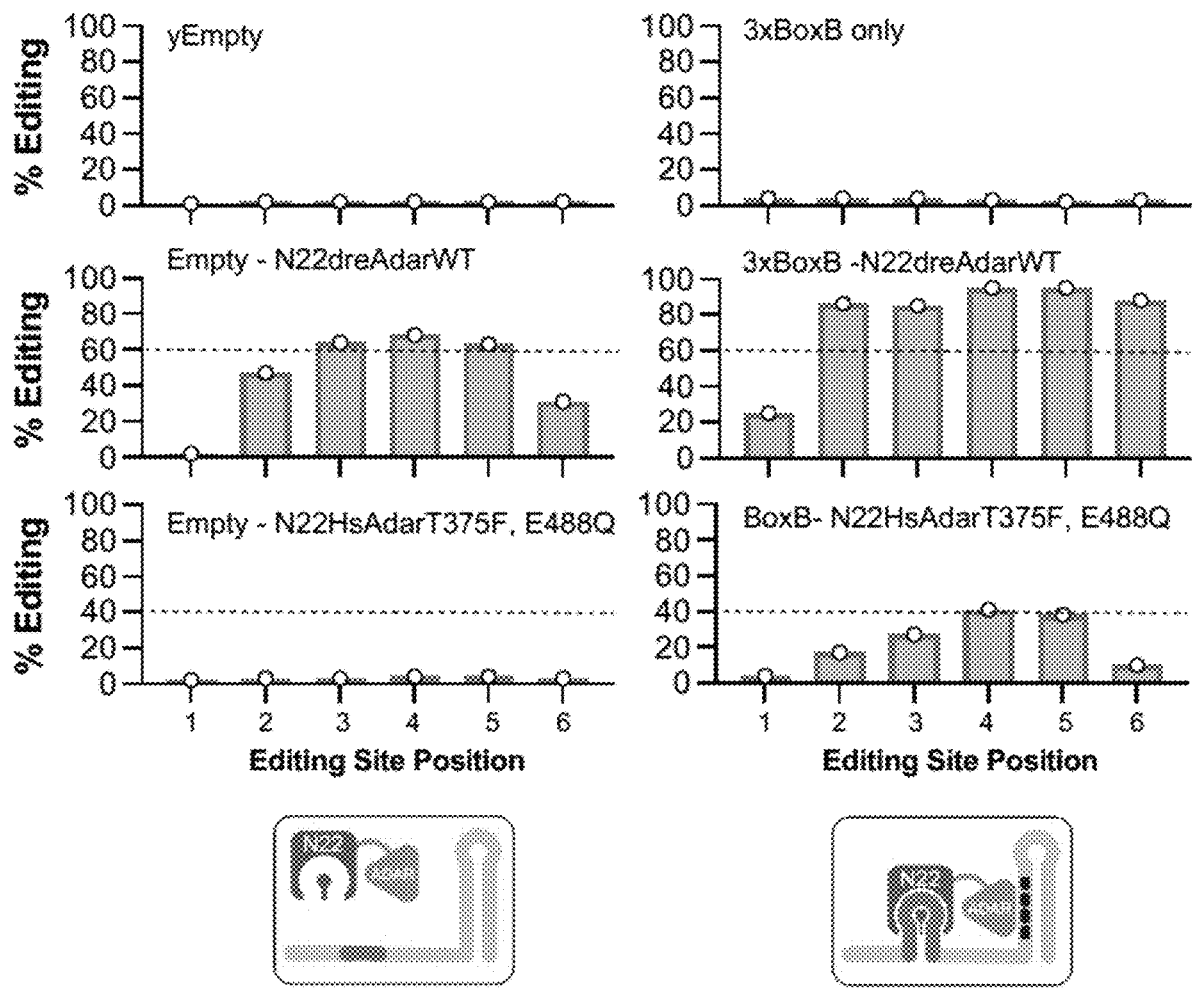
FIG. 21 depicts sensing RNA-binding proteins in yeast. The BoxB-N22 interaction was used to demonstrate that the Interactome Recorder system also works in yeast (*Saccharomyces cerevisiae*). Two Adar catalytic subunits were tested: one derived from zebrafish Adar1 and another from human Adar with the mutations T375G, E488Q. Comparing the editing of the recorder with and without BoxB site, it was found that human Adar T375G, E488Q maximizes the signal while minimizing the background editing.

The technology described herein can be used to detect RNA-binding proteins in yeast. The BoxB-N22 interaction was used to demonstrate that the Interactome Recorder system also works in yeast (*Saccharomyces cerevisiae*). Two Adar catalytic subunits were tested: one derived from zebrafish Adar1 and another from human Adar with the mutations T375G, E488Q. Comparing the editing of the recorder with and without BoxB site, it was found that human Adar T375G, E488Q maximizes the signal while minimizing the background editing (FIG. 21).

Figure 22A:
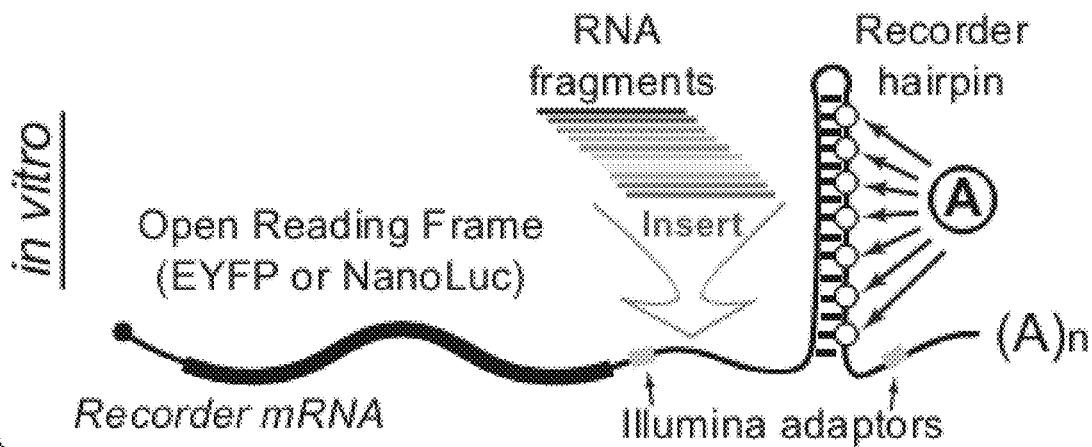
FIGS. 22A-22C demonstrate motif enrichment.
Figure 22A:
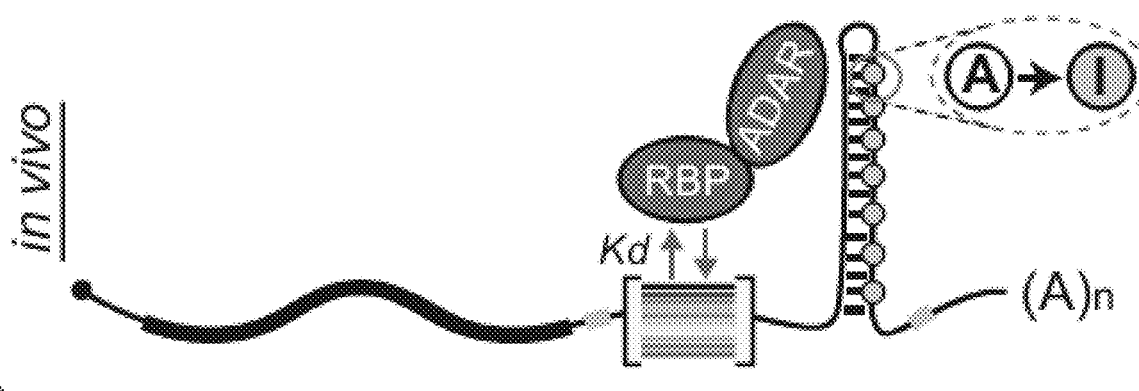
Figure 22A:
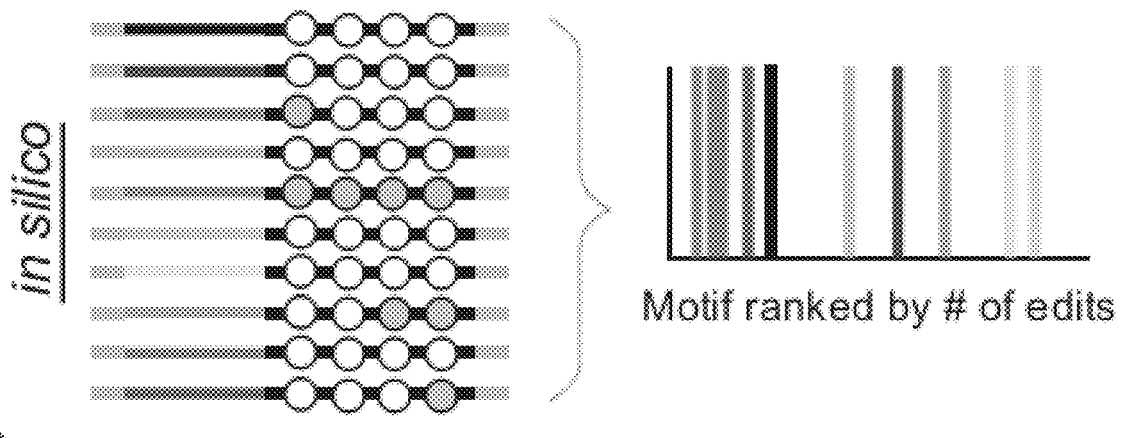
Figures 22B, 22C:

The technology described herein can be used to detect preferred motifs. A library of recorders containing all 65,536 possible 8 nucleotides long motifs was generated (FIG. 22A). Next, the recorder library together with a RBP-Adar fusion of interest was injected into zebrafish embryos or transfected into cells. High-throughput sequencing of the recorder after incubation and ranking according to the number of edits reveals which motifs are preferentially bound by the RBP of interest. Only when the motif recorder library is co-injected with Pumilio, are the Pumilio motifs observed rising to the top edited positions (FIG. 22C).

Figure 23:
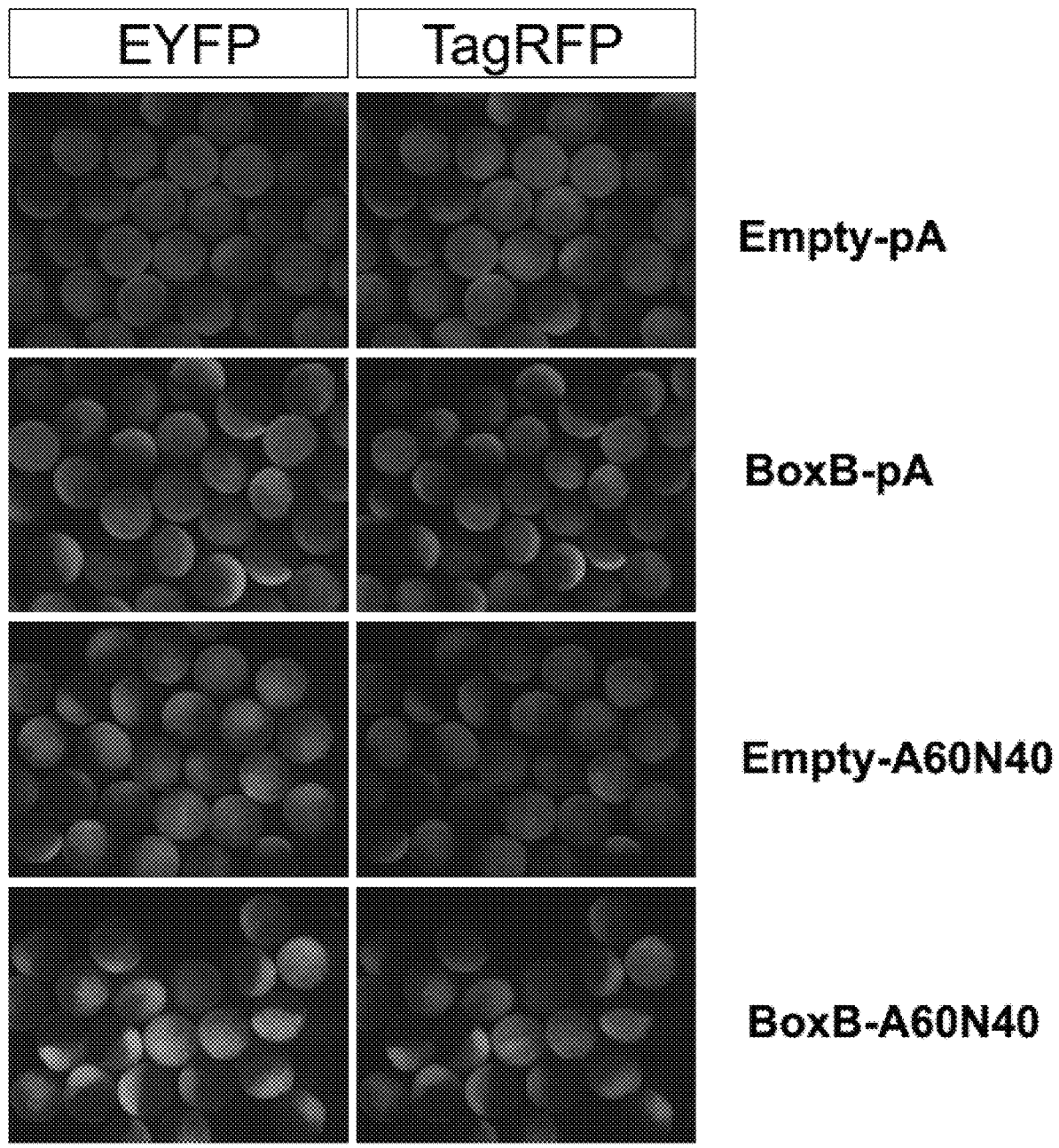
FIG. 23 depicts a test of stable polyA tails. In certain embodiments, the technology described herein can be used to evaluate the binding activity of RBPs whose binding to their target RNA induces their degradation. In such embodiments, that could represent losing the recorder, and a depletion of reads of edited recorder. To avoid the degradation of the recorder mRNA, a synthetic polyA tail consisting of 60 adenosines followed by 40 random nucleotides was have added. These 40 random nucleotides prevent 3' to 5' degradation of the mRNA. In this figure it is demonstrated that this synthetic polyA tail does not affect the translation and performance of the recorder, compared to a control recorder that contains a standard SV40 polyadenylation signal. Empty is a recorder without any RBP binding site. BoxB is a recorder with a BoxB site.

In certain embodiments, the technology described herein can be used to evaluate the binding activity of RBPs whose binding to their target RNA induces their degradation. In such embodiments, that could represent losing the recorder, and a depletion of reads of edited recorder. To avoid the degradation of the recorder mRNA, a synthetic polyA tail consisting of 60 adenosines followed by 40 random nucleotides was have added (FIG. 23). These 40 random nucleotides prevent 3' to 5' degradation of the mRNA. This synthetic polyA tail does not affect the translation and performance of the recorder, compared to a control recorder that contains a standard SV40 polyadenylation signal.

Figure 24A:
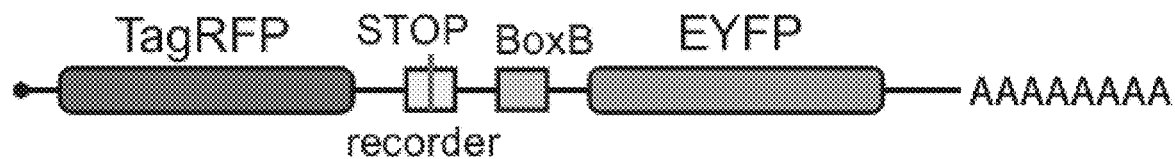
FIGS. 24A-24C depict a recorder with fluorescent read-out. In some embodiments, the read-out of the RBP-RNA interaction with the Interactome recorder systems requires sequencing of the recorder to determine the number of edits triggered by the interaction. Here the system was adapted to express a fluorescent read-out dependent on editing. This recorder was designed to comprise two fluorescent proteins (TagRFP, red, and EYFP, green) separated by a stop codon embedded in a hairpin structure that is amenable for Adar activity. Adjacent to the stop codon is an RBP binding site. Upon recruitment of the RBP-Adar fusion to the binding site, Adar can edit the stop codon to an aminoacind-encoding codon. After editing, the edited mRNA becomes a template to translate a single polypeptide chain encoding both green and fluorescent proteins.
Figure 24B:
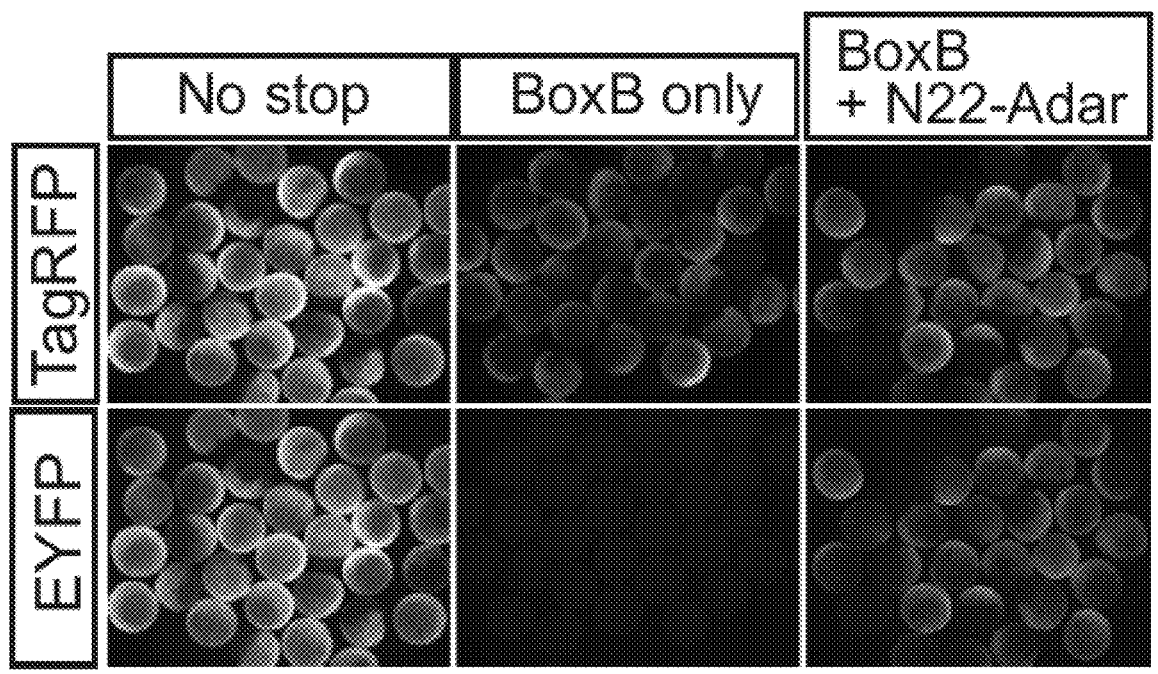
Figure 24C:
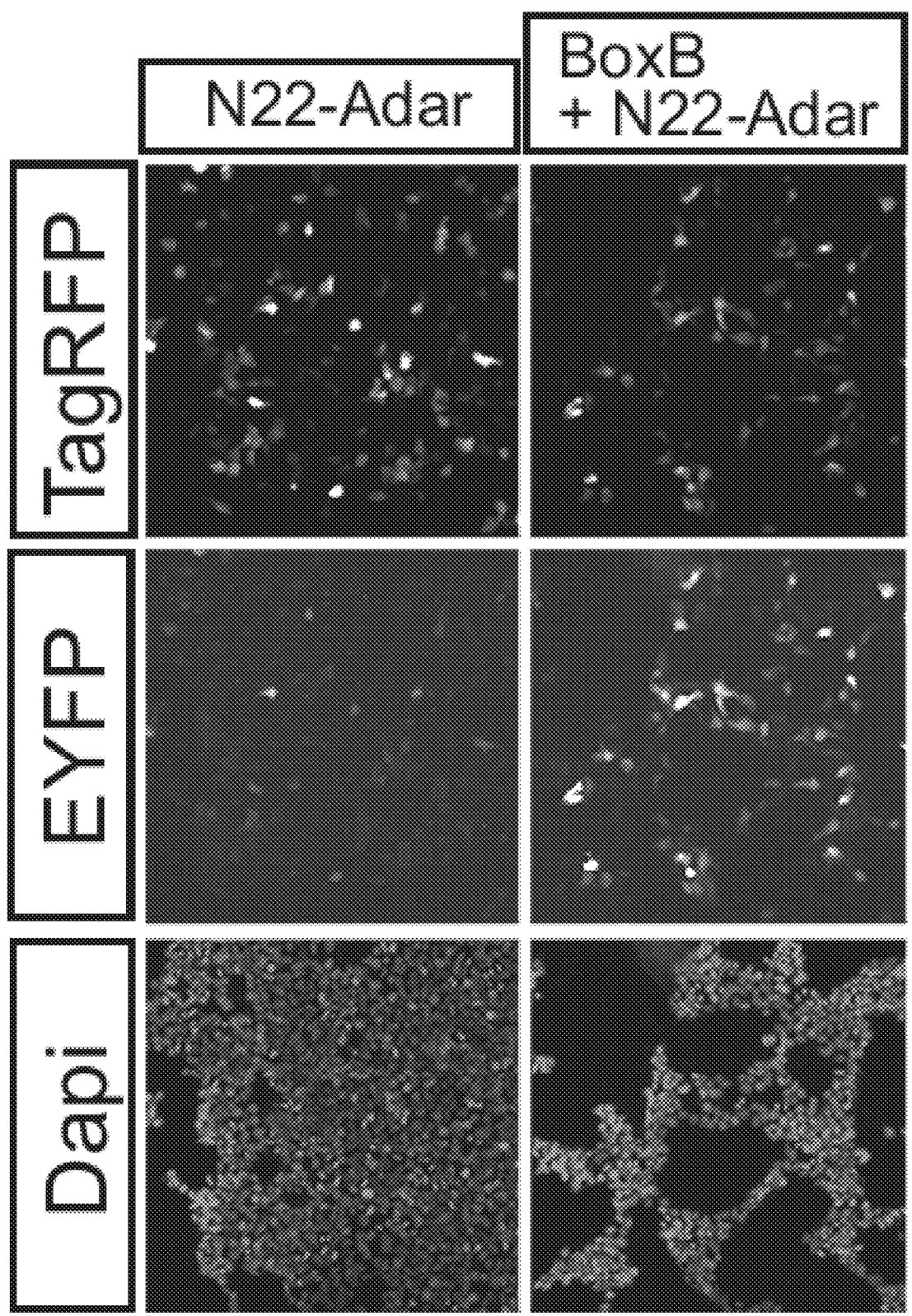

The technology described herein can be used with fluorescent read-out. In some embodiments, the read-out of the RBP-RNA interaction with the Interactome recorder systems requires sequencing of the recorder to determine the number of edits triggered by the interaction. However, in some embodiments the system expressed a fluorescent read-out dependent on editing. An exemplary such recorder was designed to comprise two fluorescent proteins (TagRFP, red, and EYFP, green) separated by a stop codon embedded in a hairpin structure that is amenable for Adar activity (FIG. 24A). Adjacent to the stop codon is an RBP binding site. Upon recruitment of the RBP-Adar fusion to the binding site, Adar can edit the stop codon to an aminoacind-encoding codon. After editing, the edited mRNA becomes a template to translate a single polypeptide chain encoding both green and fluorescent proteins. Experiment done in zebrafish embryos where the fluorescent recorder with BoxB site is injected alone or together with N22-Adar fusion. Only when the fluorescent recorder with BoxB site is injected with N22-Adar fusion are fluorescent embryos observed in the EYFP channel, equivalent to a control reporter without stop codon (FIG. 24B). Only when the recorder and TDP43-Adar fusion are expressed together, is fluorescence derived from the EYFP protein observed (FIG. 24C).

What is claimed herein is:

1. A combination comprising
   a) at least one polypeptide or pair of polypeptides comprising i) a candidate RNA-binding domain and ii) a catalytic domain of an RNA-editing enzyme; and
   b) at least one RNA comprising
      i) at least one candidate cognate binding site for the candidate RNA-binding domain and
      ii) a plurality of instances or occurrences of an at least one cognate substrate site for the catalytic domain:
      wherein the at least one candidate cognate binding site for the candidate RNA-binding domain and the at least one cognate substrate site for the catalytic domain are not found in the same naturally-occurring RNA.

2. The combination of claim 1, comprising:
   a plurality of polypeptides or pair of polypeptides collectively comprising a plurality of candidate RNA-binding domains.

3. The combination of claim 1, comprising:
   a plurality of polypeptides or pair of polypeptides collectively comprising a plurality of candidate RNA-binding domains; and
   one RNA comprising a cognate binding site.

4. The combination of claim 1, comprising:
   a plurality of RNAs collectively comprising a plurality of candidate cognate binding sites.

5. The combination of claim 1, comprising:
   one polypeptide or pair of polypeptides comprising a RNA-binding domain; and
   a plurality of RNAs collectively comprising a plurality of candidate cognate binding sites.

6. The combination of claim 1, wherein the candidate RNA-binding domain comprises: one or more PUF domains, one or more RNA-binding domains of Argonaute, one or more RNA-binding domains of lambda N, one or more REC domains of Cas, Embryonic Lethal Abnormal Vision (ELAV) RNA recognition motif (RRM), or a ribosomal protein.

7. The combination of claim 1, wherein the candidate RNA-binding domain and the candidate cognate binding site comprise:
   a) one or more RNA-binding domains of lambda N and a viral hairpin B-Box;
   b) a series of 6 to 16 PUF domains and a corresponding series of nucleotides;
   c) a series of 8 to 9 PUF domains and a corresponding series of nucleotides;
   d) one or more RNA-binding domains of Argonaute and a reverse complement sequence of the small non-coding RNA bound by the RNA-binding domain of Argonaute;
   e) one or more REC domains of Cas and a CRISPR sequence, guideRNA, or sgRNA;
   f) one or more ELAV RRMs and an AU-rich element (ARE);
   g) one or more TDP-43 RRMs and one or more U G/T G repeats; or
   h) a YTH domain and a m6A methylation site.

8. The combination of claim 1, wherein the candidate RNA-binding domain comprises a RNA-binding domain of Argonaute, the candidate cognate binding site comprises a reverse complement sequence of the small non-coding RNA bound by the RNA-binding domain of Argonaute, and the combination further comprises the small non-coding RNA.

9. The combination of claim 1, wherein the candidate RNA-binding domain comprises a ribosomal protein and the at least one RNA further comprises a sequence encoding a reporter gene.

10. The combination of claim 1, wherein the catalytic domain comprises the catalytic domain of ADAR, APOBEC, Abe7.10, or Cas.

11. The combination of claim 1, wherein the catalytic domain and the cognate substrate site comprise:
    a) the catalytic domain of ADAR and a hairpin substrate site comprising adenosine nucleotides;
    b) the catalytic domain of ADAR and a hairpin substrate site comprising at least one adenosine nucleotide mismatched with a cytosine nucleotide;
    c) the catalytic domain of APOBEC and a single-stranded substrate site comprising at least one cytosine nucleotide.

12. The combination of claim 1, wherein the at least one RNA comprises at least one of: a plurality of tandem repeats of the cognate substrate site and a plurality of tandem repeats of the cognate binding site.

13. The combination of claim 1, wherein the at least one RNA further comprises one or more sequencing adaptor sequences.

14. The combination of claim 13, wherein the at least one RNA comprises, from 5' to 3':
    a) at least one sequence encoding a first reporter gene;
    b) a domain comprising, in any order: the at least one candidate cognate binding site for the candidate RNA-binding domain, and the at least one cognate substrate site for the catalytic domain wherein the at least one cognate substrate site for the catalytic domain further comprises a stop codon; and
    c) at least one sequence encoding a second reporter gene.

15. The combination of claim 1, wherein the at least one RNA further comprises at least one of: a barcode sequence, a nuclear enrichment sequence, a nuclear localization sequence, and a polyA sequence.

16. The combination of claim 1, wherein a single polypeptide comprises the candidate RNA-binding domain and the catalytic domain of a RNA-editing enzyme.

17. A cell comprising or expressing the combination of claim 1.

18. A method of detecting the strength of the binding of a candidate RNA-binding domain to a candidate cognate binding site, the method comprising:
    a) contacting the at least one polypeptide of claim 1 with the at least one RNA of claim 1 for a period of time; and
    b) detecting the amount of editing present in the cognate substrate site.

19. The method of claim 18, wherein the amount of editing generated during the period of time correlates to the strength of the binding.

20. The method of claim 18, wherein:
a) the catalytic domain is a catalytic domain of ADAR and the amount of editing is the number of A to I edits;
b) the catalytic domain is a catalytic domain of APOBEC and the amount of editing is the number of C to U edits.

21. The method of claim 18, wherein the detecting comprises sequencing of the at least one RNA; fluorescence detection; reporter gene detection.

22. The method of claim 18, wherein the detecting comprises high-throughput sequencing of the at least one RNA.

23. The method of claim 18, wherein the method further comprises performing steps a) and b) for a plurality of different polypeptides or RNAs to determine relative binding strength or editing activity.

24. The method of claim 18, wherein the contacting step occurs in a cell or organism.

* * * * *

```
                          SEQUENCE LISTING

Sequence total quantity: 61
SEQ ID NO: 1              moltype = DNA  length = 103
FEATURE                   Location/Qualifiers
source                    1..103
                          mol_type = other DNA
                          organism = synthetic construct
SEQUENCE: 1
aaaaaaaaaa aaaaaaaaaa aaaaaaaaaa aaaaaaaaaa aaaaaaaaaa aaaaaaatgc   60
atctggtttc ctggtctgtc tcctctcggt ttaaggcggc cgc                    103

SEQ ID NO: 2              moltype = DNA  length = 146
FEATURE                   Location/Qualifiers
source                    1..146
                          mol_type = other DNA
                          organism = synthetic construct
misc_difference           1..100
                          note = This region may encompass 1-100 nucleotides
SEQUENCE: 2
aaaaaaaaaa aaaaaaaaaa aaaaaaaaaa aaaaaaaaaa aaaaaaaaaa aaaaaaaaaa   60
aaaaaaaaaa aaaaaaaaaa aaaaaaaaaa aaaaaaaaaa tgcatctggt ttcctggtct  120
gtctcctctc ggtttaaggc ggccgc                                       146

SEQ ID NO: 3              moltype =   length =
SEQUENCE: 3
000

SEQ ID NO: 4              moltype = AA  length = 23
FEATURE                   Location/Qualifiers
source                    1..23
                          mol_type = protein
                          organism = synthetic construct
SEQUENCE: 4
GNYVIQKFFE FGSLEQKLAL AER                                           23

SEQ ID NO: 5              moltype = AA  length = 22
FEATURE                   Location/Qualifiers
source                    1..22
                          mol_type = protein
                          organism = synthetic construct
SEQUENCE: 5
HVLSLALQMY GCRVIQKALE FI                                            22

SEQ ID NO: 6              moltype = AA  length = 12
FEATURE                   Location/Qualifiers
source                    1..12
                          mol_type = protein
                          organism = synthetic construct
SEQUENCE: 6
NGNHVVQKCI EC                                                       12

SEQ ID NO: 7              moltype = AA  length = 21
FEATURE                   Location/Qualifiers
source                    1..21
                          mol_type = protein
                          organism = synthetic construct
SEQUENCE: 7
VFALSTHPYG CRVIQRILEH C                                             21

SEQ ID NO: 8              moltype = AA  length = 14
FEATURE                   Location/Qualifiers
source                    1..14
                          mol_type = protein
```

```
                                  -continued
                     organism = synthetic construct
SEQUENCE: 8
QYGNYVIQHV LEHG                                                          14

SEQ ID NO: 9          moltype = AA  length = 21
FEATURE               Location/Qualifiers
source                1..21
                      mol_type = protein
                      organism = synthetic construct
SEQUENCE: 9
NVLVLSQHKF ASNVVEKCVT H                                                  21

SEQ ID NO: 10         moltype = AA  length = 22
FEATURE               Location/Qualifiers
source                1..22
                      mol_type = protein
                      organism = synthetic construct
SEQUENCE: 10
ALYTMMKDQY ANYVVQKMID VA                                                 22

SEQ ID NO: 11         moltype = AA  length = 9
FEATURE               Location/Qualifiers
source                1..9
                      mol_type = protein
                      organism = synthetic construct
SEQUENCE: 11
YGKHILAKL                                                                9

SEQ ID NO: 12         moltype = AA  length = 125
FEATURE               Location/Qualifiers
source                1..125
                      mol_type = protein
                      organism = synthetic construct
SEQUENCE: 12
QNKEHFQDEC TKLLVGNIVI TRYNNRTYRI DDVDWNKTPK DSFTMSDGKE ITFLEYYSKN        60
YGITVKEEDQ PLLIHRPSER QDNHGMLLKG EILLLPELSF MTGIPEKMKK DFRAMKDLAQ        120
QINLS                                                                    125

SEQ ID NO: 13         moltype = AA  length = 35
FEATURE               Location/Qualifiers
source                1..35
                      mol_type = protein
                      organism = synthetic construct
SEQUENCE: 13
DAQTRRRERR AEKQAQWKAA NPLLVGVSAK PVNRP                                   35

SEQ ID NO: 14         moltype = AA  length = 134
FEATURE               Location/Qualifiers
source                1..134
                      mol_type = protein
                      organism = synthetic construct
SEQUENCE: 14
RVFIIKSYSE DDIHRSIKYS IWCSTEHGNK RLDSAFRCMS SKGPVYLLFS VNGSGHFCGV        60
AEMKSPVDYG TSAGVWSQDK WKGKFDVQWI FVKDVPNNQL RHIRLENNDN KPVTNSRDTQ        120
EVPLEKAKQV LKII                                                          134

SEQ ID NO: 15         moltype = AA  length = 554
FEATURE               Location/Qualifiers
source                1..554
                      mol_type = protein
                      organism = synthetic construct
SEQUENCE: 15
IEMLHQSMVN ILNINLKNVE IEKIEKILKS TQYSNSERLE NLLELYELSK NKNKIETEIF        60
KFICGLKGTI SKIYVEDKFE DEFAKMTLSF RDSNFDEKII EIEDNLDDDK YDMFLLIKQI        120
HDWSVLANIM NGEEYLSVAR VKLYDKHKKD LEVLKKYYKQ NSMEEYNKMF RQMNDGNYSA        180
YVGSVIYKDN SVRRGCKSKK EDFYKNILNT IKSWEDCEAK EYITSEIDKG NFLPKQITAS        240
NGVIPNQVHK KELKKILKNA SEYLNFLNEK DESGYTISEK IVKLFEFQIP YYVGPIAYNI        300
GNDESKHRHN MWSVRKEKGP IYPWNFEQKI DIKKSSEKPI RNLINHCTYL NDEEVLPKNS        360
LLYEKFMVLN ELNKLKINGE KISVELKQNI FNDLFKKGKK VTKKGLIKYL KEQGEIDNCE        420
EVEISGIDGD FTNKLSNYKK FADIFGVQSL TYEQTDIAEN IIRYSTIYGD SRKFLEERIR        480
EEYSNVLDEK QIKRILGMKF KDWGRLSKEL LELSGVDKET GEIASVISRM WNDNYNLMEL        540
IATERFSYAY EIEQ                                                          554

SEQ ID NO: 16         moltype = AA  length = 322
FEATURE               Location/Qualifiers
source                1..322
                      mol_type = protein
                      organism = synthetic construct
SEQUENCE: 16
```

```
SVSTGTKCIN GEYMSDRGLA LNDCHAEIIS RRSLLRFLYT QLELYLNNKD DQKRSIFQKS    60
ERGGFRLKEN VQFHLYISTS PCGDARIFSP HEPILEEPAD RHPNRKARGQ LRTKIESGEG   120
TIPVRSNASI QTWDGVLQGE RLLTMSCSDK IARWNVVGIQ GSLLSIFVEP IYFSSIILGS   180
LYHGDHLSRA MYQRISNIED LPPLYTLNKP LLSGISNAEA RQPGKAPNFS VNWTVGDSAI   240
EVINATTGKD ELGRASRLCK HALYCRWMRV HGKVPSHLLR SKITKPNVYH ESKLAAKEYQ   300
AAKARLFTAF IKAGLGAWVE KP                                           322

SEQ ID NO: 17           moltype = AA  length = 171
FEATURE                 Location/Qualifiers
source                  1..171
                        mol_type = protein
                        organism = synthetic construct
SEQUENCE: 17
FYFHFKNLRK AYGRNESWLC FTMEVVKHHS PVSWKRGVFR NQVDPETGRH AERCFLSWFA    60
DDILSPNTNY EVTWYTSWSP CPECAGEVAE FLARHSNVNL TIKTARLYYF DDTDAAEGLR   120
SLSQEGASVE IMGYKDFKYC WENFVYNDDE PFKPWDGLDY NFLDLDSKLQ E            171

SEQ ID NO: 18           moltype = AA  length = 78
FEATURE                 Location/Qualifiers
source                  1..78
                        mol_type = protein
                        organism = Homo sapiens
SEQUENCE: 18
QKTSDLIVLG LPWKTTEQDL KEYFSTFGEV LMVQVKKDLK TGHSKGFGFV RFTEYETQVK    60
VMSQRHMIDG RWCDCKLP                                                 78

SEQ ID NO: 19           moltype = AA  length = 71
FEATURE                 Location/Qualifiers
source                  1..71
                        mol_type = protein
                        organism = Homo sapiens
SEQUENCE: 19
RKVFVGRCTE DMTEDELREF FSQYGDVMDV FIPKPFRAFA FVTFADDQIA QSLCGEDLII    60
KGISVHISNA E                                                        71

SEQ ID NO: 20           moltype = AA  length = 414
FEATURE                 Location/Qualifiers
source                  1..414
                        mol_type = protein
                        organism = Homo sapiens
SEQUENCE: 20
MSEYIRVTED ENDEPIEIPS EDDGTVLLST VTAQFPGACG LRYRNPVSQC MRGVRLVEGI    60
LHAPDAGWGN LVYVVNYPKD NKRKMDETDA SSAVKVKRAV QKTSDLIVLG LPWKTTEQDL   120
KEYFSTFGEV LMVQVKKDLK TGHSKGFGFV RFTEYETQVK VMSQRHMIDG RWCDCKLPNS   180
KQSQDEPLRS RKVFVGRCTE DMTEDELREF FSQYGDVMDV FIPKPFRAFA FVTFADDQIA   240
QSLCGEDLII KGISVHISNA EPKHNSNRQL ERSGRFGGNP GGFGNQGGFG NSRGGGAGLG   300
NNQGSNMGGG MNFGAFSINP AMMAAAQAAL QSSWGMMGML ASQQNQSGPS GNNQNQGNMQ   360
REPNQAFGSG NNSYSGSNSG AAIGWGSASN AGSGSGFNGG FGSSMDSKSS GWGM         414

SEQ ID NO: 21           moltype = AA  length = 79
FEATURE                 Location/Qualifiers
source                  1..79
                        mol_type = protein
                        organism = synthetic construct
SEQUENCE: 21
TNLIVNYLPQ NMTQDELRSL FSSIGEVESA KLIRDKVAGH SLGYGFVNYV TAKDAERAIN    60
TLNGLRLQSK TIKVSYARP                                                79

SEQ ID NO: 22           moltype = AA  length = 81
FEATURE                 Location/Qualifiers
source                  1..81
                        mol_type = protein
                        organism = synthetic construct
SEQUENCE: 22
ANLYISGLPR TMTQKDVEDM FSRFGRIINS RVLVDQTTGL SRGVAFIRFD KRSEAEEAIT    60
SFNGHKPPGS SEPITVKFAA N                                             81

SEQ ID NO: 23           moltype = AA  length = 79
FEATURE                 Location/Qualifiers
source                  1..79
                        mol_type = protein
                        organism = synthetic construct
SEQUENCE: 23
WCIFIYNLGQ DADEGILWQM FGPFGAVTNV KVIRDFNTNK CKGFGFVTMT NYEEAAMAIA    60
SLNGYRLGDK ILQVSFKTN                                                79

SEQ ID NO: 24           moltype = DNA  length = 200
FEATURE                 Location/Qualifiers
source                  1..200
```

```
                         mol_type = other DNA
                         organism = synthetic construct
misc_difference          101
                         note = a, c, t, g, unknown or other
misc_difference          102
                         note = a, c, t, g, unknown or other
misc_difference          103
                         note = a, c, t, g, unknown or other
misc_difference          104
                         note = a, c, t, g, unknown or other
misc_difference          105
                         note = a, c, t, g, unknown or other
misc_difference          106
                         note = a, c, t, g, unknown or other
misc_difference          107
                         note = a, c, t, g, unknown or other
misc_difference          108
                         note = a, c, t, g, unknown or other
misc_difference          109
                         note = a, c, t, g, unknown or other
misc_difference          110
                         note = a, c, t, g, unknown or other
misc_difference          111
                         note = a, c, t, g, unknown or other
misc_difference          112
                         note = a, c, t, g, unknown or other
misc_difference          113
                         note = a, c, t, g, unknown or other
misc_difference          114
                         note = a, c, t, g, unknown or other
misc_difference          115
                         note = a, c, t, g, unknown or other
misc_difference          116
                         note = a, c, t, g, unknown or other
misc_difference          117
                         note = a, c, t, g, unknown or other
misc_difference          118
                         note = a, c, t, g, unknown or other
misc_difference          119
                         note = a, c, t, g, unknown or other
misc_difference          120
                         note = a, c, t, g, unknown or other
misc_difference          121
                         note = a, c, t, g, unknown or other
misc_difference          122
                         note = a, c, t, g, unknown or other
misc_difference          123
                         note = a, c, t, g, unknown or other
misc_difference          124
                         note = a, c, t, g, unknown or other
misc_difference          125
                         note = a, c, t, g, unknown or other
misc_difference          126
                         note = a, c, t, g, unknown or other
misc_difference          127
                         note = a, c, t, g, unknown or other
misc_difference          128
                         note = a, c, t, g, unknown or other
misc_difference          129
                         note = a, c, t, g, unknown or other
misc_difference          130
                         note = a, c, t, g, unknown or other
misc_difference          131
                         note = a, c, t, g, unknown or other
misc_difference          132
                         note = a, c, t, g, unknown or other
misc_difference          133
                         note = a, c, t, g, unknown or other
misc_difference          134
                         note = a, c, t, g, unknown or other
misc_difference          135
                         note = a, c, t, g, unknown or other
misc_difference          136
                         note = a, c, t, g, unknown or other
misc_difference          137
                         note = a, c, t, g, unknown or other
misc_difference          138
                         note = a, c, t, g, unknown or other
misc_difference          139
```

-continued

| | |
|---|---|
| misc_difference | note = a, c, t, g, unknown or other 140 |
| misc_difference | note = a, c, t, g, unknown or other 141 |
| misc_difference | note = a, c, t, g, unknown or other 142 |
| misc_difference | note = a, c, t, g, unknown or other 143 |
| misc_difference | note = a, c, t, g, unknown or other 144 |
| misc_difference | note = a, c, t, g, unknown or other 145 |
| misc_difference | note = a, c, t, g, unknown or other 146 |
| misc_difference | note = a, c, t, g, unknown or other 147 |
| misc_difference | note = a, c, t, g, unknown or other 148 |
| misc_difference | note = a, c, t, g, unknown or other 149 |
| misc_difference | note = a, c, t, g, unknown or other 150 |
| misc_difference | note = a, c, t, g, unknown or other 151 |
| misc_difference | note = a, c, t, g, unknown or other 152 |
| misc_difference | note = a, c, t, g, unknown or other 153 |
| misc_difference | note = a, c, t, g, unknown or other 154 |
| misc_difference | note = a, c, t, g, unknown or other 155 |
| misc_difference | note = a, c, t, g, unknown or other 156 |
| misc_difference | note = a, c, t, g, unknown or other 157 |
| misc_difference | note = a, c, t, g, unknown or other 158 |
| misc_difference | note = a, c, t, g, unknown or other 159 |
| misc_difference | note = a, c, t, g, unknown or other 160 |
| misc_difference | note = a, c, t, g, unknown or other 161 |
| misc_difference | note = a, c, t, g, unknown or other 162 |
| misc_difference | note = a, c, t, g, unknown or other 163 |
| misc_difference | note = a, c, t, g, unknown or other 164 |
| misc_difference | note = a, c, t, g, unknown or other 165 |
| misc_difference | note = a, c, t, g, unknown or other 166 |
| misc_difference | note = a, c, t, g, unknown or other 167 |
| misc_difference | note = a, c, t, g, unknown or other 168 |
| misc_difference | note = a, c, t, g, unknown or other 169 |
| misc_difference | note = a, c, t, g, unknown or other 170 |
| misc_difference | note = a, c, t, g, unknown or other 171 |
| misc_difference | note = a, c, t, g, unknown or other 172 |
| misc_difference | note = a, c, t, g, unknown or other 173 |
| misc_difference | note = a, c, t, g, unknown or other 174 |
| misc_difference | note = a, c, t, g, unknown or other 175 |
| misc_difference | note = a, c, t, g, unknown or other 176 |
| misc_difference | note = a, c, t, g, unknown or other 177 |
| misc_difference | note = a, c, t, g, unknown or other 178 |
| | note = a, c, t, g, unknown or other |

| | |
|---|---|
| misc_difference | 179 |
| | note = a, c, t, g, unknown or other |
| misc_difference | 180 |
| | note = a, c, t, g, unknown or other |
| misc_difference | 181 |
| | note = a, c, t, g, unknown or other |
| misc_difference | 182 |
| | note = a, c, t, g, unknown or other |
| misc_difference | 183 |
| | note = a, c, t, g, unknown or other |
| misc_difference | 184 |
| | note = a, c, t, g, unknown or other |
| misc_difference | 185 |
| | note = a, c, t, g, unknown or other |
| misc_difference | 186 |
| | note = a, c, t, g, unknown or other |
| misc_difference | 187 |
| | note = a, c, t, g, unknown or other |
| misc_difference | 188 |
| | note = a, c, t, g, unknown or other |
| misc_difference | 189 |
| | note = a, c, t, g, unknown or other |
| misc_difference | 190 |
| | note = a, c, t, g, unknown or other |
| misc_difference | 191 |
| | note = a, c, t, g, unknown or other |
| misc_difference | 192 |
| | note = a, c, t, g, unknown or other |
| misc_difference | 193 |
| | note = a, c, t, g, unknown or other |
| misc_difference | 194 |
| | note = a, c, t, g, unknown or other |
| misc_difference | 195 |
| | note = a, c, t, g, unknown or other |
| misc_difference | 196 |
| | note = a, c, t, g, unknown or other |
| misc_difference | 197 |
| | note = a, c, t, g, unknown or other |
| misc_difference | 198 |
| | note = a, c, t, g, unknown or other |
| misc_difference | 199 |
| | note = a, c, t, g, unknown or other |
| misc_difference | 200 |
| | note = a, c, t, g, unknown or other |
| misc_difference | 1..100 |
| | note = This region may encompass 1-100 nucleotides |
| misc_difference | 101..200 |
| | note = This region may encompass 1-100 nucleotides |

SEQUENCE: 24

```
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn                                               200
```

| | |
|---|---|
| SEQ ID NO: 25 | moltype = DNA   length = 100 |
| FEATURE | Location/Qualifiers |
| source | 1..100 |
| | mol_type = other DNA |
| | organism = synthetic construct |
| misc_difference | 61 |
| | note = a, c, t, g, unknown or other |
| misc_difference | 62 |
| | note = a, c, t, g, unknown or other |
| misc_difference | 63 |
| | note = a, c, t, g, unknown or other |
| misc_difference | 64 |
| | note = a, c, t, g, unknown or other |
| misc_difference | 65 |
| | note = a, c, t, g, unknown or other |
| misc_difference | 66 |
| | note = a, c, t, g, unknown or other |
| misc_difference | 67 |
| | note = a, c, t, g, unknown or other |
| misc_difference | 68 |
| | note = a, c, t, g, unknown or other |
| misc_difference | 69 |
| | note = a, c, t, g, unknown or other |
| misc_difference | 70 |
| | note = a, c, t, g, unknown or other |

| | | |
|---|---|---|
| misc_difference | 71 | |
| | note = a, c, t, g, unknown or other | |
| misc_difference | 72 | |
| | note = a, c, t, g, unknown or other | |
| misc_difference | 73 | |
| | note = a, c, t, g, unknown or other | |
| misc_difference | 74 | |
| | note = a, c, t, g, unknown or other | |
| misc_difference | 75 | |
| | note = a, c, t, g, unknown or other | |
| misc_difference | 76 | |
| | note = a, c, t, g, unknown or other | |
| misc_difference | 77 | |
| | note = a, c, t, g, unknown or other | |
| misc_difference | 78 | |
| | note = a, c, t, g, unknown or other | |
| misc_difference | 79 | |
| | note = a, c, t, g, unknown or other | |
| misc_difference | 80 | |
| | note = a, c, t, g, unknown or other | |
| misc_difference | 81 | |
| | note = a, c, t, g, unknown or other | |
| misc_difference | 82 | |
| | note = a, c, t, g, unknown or other | |
| misc_difference | 83 | |
| | note = a, c, t, g, unknown or other | |
| misc_difference | 84 | |
| | note = a, c, t, g, unknown or other | |
| misc_difference | 85 | |
| | note = a, c, t, g, unknown or other | |
| misc_difference | 86 | |
| | note = a, c, t, g, unknown or other | |
| misc_difference | 87 | |
| | note = a, c, t, g, unknown or other | |
| misc_difference | 88 | |
| | note = a, c, t, g, unknown or other | |
| misc_difference | 89 | |
| | note = a, c, t, g, unknown or other | |
| misc_difference | 90 | |
| | note = a, c, t, g, unknown or other | |
| misc_difference | 91 | |
| | note = a, c, t, g, unknown or other | |
| misc_difference | 92 | |
| | note = a, c, t, g, unknown or other | |
| misc_difference | 93 | |
| | note = a, c, t, g, unknown or other | |
| misc_difference | 94 | |
| | note = a, c, t, g, unknown or other | |
| misc_difference | 95 | |
| | note = a, c, t, g, unknown or other | |
| misc_difference | 96 | |
| | note = a, c, t, g, unknown or other | |
| misc_difference | 97 | |
| | note = a, c, t, g, unknown or other | |
| misc_difference | 98 | |
| | note = a, c, t, g, unknown or other | |
| misc_difference | 99 | |
| | note = a, c, t, g, unknown or other | |
| misc_difference | 100 | |
| | note = a, c, t, g, unknown or other | |
| SEQUENCE: 25 | | |
| aaaaaaaaaa aaaaaaaaaa aaaaaaaaaa aaaaaaaaaa aaaaaaaaaa aaaaaaaaaa | | 60 |
| nnnnnnnnnn nnnnnnnnnn nnnnnnnnnn nnnnnnnnnn | | 100 |
| SEQ ID NO: 26 | moltype = AA   length = 701 | |
| FEATURE | Location/Qualifiers | |
| source | 1..701 | |
| | mol_type = protein | |
| | organism = Homo sapiens | |
| SEQUENCE: 26 | | |
| MDIEDEENMS SSSTDVKENR NLDNVSPKDG STPGPGEGSQ LSNGGGGGPG RKRPLEEGSN | | 60 |
| GHSKYRLKKR RKTPGPVLPK NALMQLNEIK PGLQYTLLSQ TGPVHAPLFV MSVEVNGQVF | | 120 |
| EGSGPTKKKA KLHAAEKALR SFVQFPNASE AHLAMGRTLS VNTDFTSDQA DFPDTLFNGF | | 180 |
| ETPDKAEPPF YVGSNGDDSF SSSGDLSLSA SPVPASLAQP PLPVLPPFPP PSGKNPVMIL | | 240 |
| NELRPGLKYD FLSESGESHA KSFVMSVVVD GQFFEGSGRN KKLAKARAAQ SALAAIFNLH | | 300 |
| LDQTPSRQPI PSEGLQLHLP QVLADAVSRL VLGKFGDLTD NFSSPHARRK VLAGVVMTTG | | 360 |
| TDVKDAKVIS VSTGTKCING EYMSDRGLAL NDCHAEIISR RSLLRFLYTQ LELYLNNKDD | | 420 |
| QKRSIFQKSE RGGFRLKENV QFHLYISTSP CGDARIFSPH EPILEEPADR HPNRKARGQL | | 480 |
| RTKIESGEGT IPVRSNASIQ TWDGVLQGER LLTMSCSDKI ARWNVVGIQG SLLSIFVEPI | | 540 |

```
YFSSIILGSL YHGDHLSRAM YQRISNIEDL PPLYTLNKPL LSGISNAEAR QPGKAPNFSV    600
NWTVGDSAIE VINATTGKDE LGRASRLCKH ALYCRWMRVH GKVPSHLLRS KITKPNVYHE    660
SKLAAKEYQA AKARLFTAFI KAGLGAWVEK PTEQDQFSLT P                       701

SEQ ID NO: 27            moltype = AA   length = 322
FEATURE                  Location/Qualifiers
source                   1..322
                         mol_type = protein
                         organism = synthetic construct
SEQUENCE: 27
SVSTGGKCIN GEYMSDRGLA LNDCHAEIIS RRSLLRFLYT QLELYLNNKD DQKRSIFQKS     60
ERGGFRLKEN VQFHLYISTS PCGDARIFSP HEPILEEPAD RHPNRKARGQ LRTKIESGEG    120
TIPVRSNASI QTWDGVLQGE RLLTMSCSDK IARWNVVGIQ GSLLSIFVEP IYFSSIILGS    180
LYHGDHLSRA MYQRISNIED LPPLYTLNKP LLSGISNAEA RQPGKAPNFS VNWTVGDSAI    240
EVINATTGKD ELGRASRLCK HALYCRWMRV HGKVPSHLLR SKITKPNVYH ESKLAAKEYQ    300
AAKARLFTAF IKAGLGAWVE KP                                            322

SEQ ID NO: 28            moltype = AA   length = 322
FEATURE                  Location/Qualifiers
source                   1..322
                         mol_type = protein
                         organism = synthetic construct
SEQUENCE: 28
SVSTGTKCIN GEYMSDRGLA LNDCHAEIIS RRSLLRFLYT QLELYLNNKD DQKRSIFQKS     60
ERGGFRLKEN VQFHLYISTS PCGDARIFSP HEPILEEPAD RHPNRKARGQ LRTKIESGQG    120
TIPVRSNASI QTWDGVLQGE RLLTMSCSDK IARWNVVGIQ GSLLSIFVEP IYFSSIILGS    180
LYHGDHLSRA MYQRISNIED LPPLYTLNKP LLSGISNAEA RQPGKAPNFS VNWTVGDSAI    240
EVINATTGKD ELGRASRLCK HALYCRWMRV HGKVPSHLLR SKITKPNVYH ESKLAAKEYQ    300
AAKARLFTAF IKAGLGAWVE KP                                            322

SEQ ID NO: 29            moltype = AA   length = 322
FEATURE                  Location/Qualifiers
source                   1..322
                         mol_type = protein
                         organism = synthetic construct
SEQUENCE: 29
SVSTGGKCIN GEYMSDRGLA LNDCHAEIIS RRSLLRFLYT QLELYLNNKD DQKRSIFQKS     60
ERGGFRLKEN VQFHLYISTS PCGDARIFSP HEPILEEPAD RHPNRKARGQ LRTKIESGQG    120
TIPVRSNASI QTWDGVLQGE RLLTMSCSDK IARWNVVGIQ GSLLSIFVEP IYFSSIILGS    180
LYHGDHLSRA MYQRISNIED LPPLYTLNKP LLSGISNAEA RQPGKAPNFS VNWTVGDSAI    240
EVINATTGKD ELGRASRLCK HALYCRWMRV HGKVPSHLLR SKITKPNVYH ESKLAAKEYQ    300
AAKARLFTAF IKAGLGAWVE KP                                            322

SEQ ID NO: 30            moltype = DNA   length = 19
FEATURE                  Location/Qualifiers
source                   1..19
                         mol_type = other DNA
                         organism = synthetic construct
SEQUENCE: 30
gccaacgcta ttctggctg                                                 19

SEQ ID NO: 31            moltype = DNA   length = 25
FEATURE                  Location/Qualifiers
source                   1..25
                         mol_type = other DNA
                         organism = synthetic construct
SEQUENCE: 31
tttgtgtgtg tgtgtgtgtg tgtgt                                          25

SEQ ID NO: 32            moltype = DNA   length = 19
FEATURE                  Location/Qualifiers
source                   1..19
                         mol_type = other DNA
                         organism = synthetic construct
SEQUENCE: 32
cggttgcgat aagaccgac                                                 19

SEQ ID NO: 33            moltype = DNA   length = 25
FEATURE                  Location/Qualifiers
source                   1..25
                         mol_type = other DNA
                         organism = synthetic construct
SEQUENCE: 33
aaacacacac acacacacac acaca                                          25

SEQ ID NO: 34            moltype = DNA   length = 20
FEATURE                  Location/Qualifiers
source                   1..20
                         mol_type = other DNA
```

```
                        organism = synthetic construct
SEQUENCE: 34
gccaacgcta ttctggctga                                                20

SEQ ID NO: 35           moltype = DNA  length = 53
FEATURE                 Location/Qualifiers
source                  1..53
                        mol_type = other DNA
                        organism = synthetic construct
SEQUENCE: 35
gattctatcc aacgcaattc tggcacgtcc aatccaatcc aatccaatcc aat            53

SEQ ID NO: 36           moltype = DNA  length = 53
FEATURE                 Location/Qualifiers
source                  1..53
                        mol_type = other DNA
                        organism = synthetic construct
SEQUENCE: 36
ctaagatagg ttgcgttaag accgtgcagg ttaggttagg ttaggttagg tta            53

SEQ ID NO: 37           moltype = DNA  length = 52
FEATURE                 Location/Qualifiers
source                  1..52
                        mol_type = other DNA
                        organism = synthetic construct
SEQUENCE: 37
attctatcca acgcaattct ggcacgtcca atccaatcca atccaatcca at             52

SEQ ID NO: 38           moltype = DNA  length = 52
FEATURE                 Location/Qualifiers
source                  1..52
                        mol_type = other DNA
                        organism = synthetic construct
SEQUENCE: 38
ccaatccaat taaattagat tagattagat tagattagat tagattagac ag             52

SEQ ID NO: 39           moltype = DNA  length = 52
FEATURE                 Location/Qualifiers
source                  1..52
                        mol_type = other DNA
                        organism = synthetic construct
SEQUENCE: 39
ggttaggtta atttaatcta atctaatcta atctaatcta atctaatctg tc             52

SEQ ID NO: 40           moltype = DNA  length = 52
FEATURE                 Location/Qualifiers
source                  1..52
                        mol_type = other DNA
                        organism = synthetic construct
SEQUENCE: 40
ccaatccaat taaattagat tagattggat tggattggat tggattggac ag             52

SEQ ID NO: 41           moltype = DNA  length = 41
FEATURE                 Location/Qualifiers
source                  1..41
                        mol_type = other DNA
                        organism = synthetic construct
SEQUENCE: 41
gagcctagca tttgaactat agtgagtcgt attacctggc t                        41

SEQ ID NO: 42           moltype = DNA  length = 42
FEATURE                 Location/Qualifiers
source                  1..42
                        mol_type = other DNA
                        organism = synthetic construct
SEQUENCE: 42
ctcggatcgt gaaacttgat atcactcagc ataatggacc ga                       42

SEQ ID NO: 43           moltype = DNA  length = 42
FEATURE                 Location/Qualifiers
source                  1..42
                        mol_type = other DNA
                        organism = synthetic construct
SEQUENCE: 43
gagcctagca ctttgaacta tagtgagtcg tattacctgg ct                       42

SEQ ID NO: 44           moltype = DNA  length = 41
FEATURE                 Location/Qualifiers
source                  1..41
```

```
                          mol_type = other DNA
                          organism = synthetic construct
SEQUENCE: 44
tgagctagca ctttgactat agtgagtcgt attacctggc t                 41

SEQ ID NO: 45             moltype = DNA   length = 41
FEATURE                   Location/Qualifiers
source                    1..41
                          mol_type = other DNA
                          organism = synthetic construct
SEQUENCE: 45
tccgactgca ctttgactat agtgagtcgt attacctggc t                 41

SEQ ID NO: 46             moltype = DNA   length = 53
FEATURE                   Location/Qualifiers
source                    1..53
                          mol_type = other DNA
                          organism = synthetic construct
SEQUENCE: 46
gaattctatc caacgcaatt ctggcacgtc caatccaatc caatccaatc caa     53

SEQ ID NO: 47             moltype = DNA   length = 53
FEATURE                   Location/Qualifiers
source                    1..53
                          mol_type = other DNA
                          organism = synthetic construct
SEQUENCE: 47
cttaagatag gttgcgttaa gaccgtgcag gttaggttag gttaggttag gtt     53

SEQ ID NO: 48             moltype = DNA   length = 52
FEATURE                   Location/Qualifiers
source                    1..52
                          mol_type = other DNA
                          organism = synthetic construct
SEQUENCE: 48
tccaatccaa ttaaattaga ttagattaga ttagattaga ttagattaga ca      52

SEQ ID NO: 49             moltype = DNA   length = 52
FEATURE                   Location/Qualifiers
source                    1..52
                          mol_type = other DNA
                          organism = synthetic construct
SEQUENCE: 49
aggttaggtt aatttaatct aatctaatct aatctaatct aatctaatct gt      52

SEQ ID NO: 50             moltype = DNA   length = 52
FEATURE                   Location/Qualifiers
source                    1..52
                          mol_type = other DNA
                          organism = synthetic construct
SEQUENCE: 50
tccaatccaa ttaaattaga ttagattgga ttggattaga ttggattaga ca      52

SEQ ID NO: 51             moltype = DNA   length = 44
FEATURE                   Location/Qualifiers
source                    1..44
                          mol_type = other DNA
                          organism = synthetic construct
SEQUENCE: 51
ctaaactggg ccctgaagaa gggcccatat agggccctga agaa               44

SEQ ID NO: 52             moltype = DNA   length = 44
FEATURE                   Location/Qualifiers
source                    1..44
                          mol_type = other DNA
                          organism = synthetic construct
SEQUENCE: 52
gatttgaccc gggacttctt cccgggtata tcccgggact tctt               44

SEQ ID NO: 53             moltype = DNA   length = 53
FEATURE                   Location/Qualifiers
source                    1..53
                          mol_type = other DNA
                          organism = synthetic construct
SEQUENCE: 53
gggcccctat ccaacgcaat tctggcacgt ccaatccaat ccaatccaat cca     53

SEQ ID NO: 54             moltype = DNA   length = 53
FEATURE                   Location/Qualifiers
```

```
source                  1..53
                        mol_type = other DNA
                        organism = synthetic construct
SEQUENCE: 54
cccggggata ggttgcgtta agaccgtgca ggttaggtta ggttaggtta ggt        53

SEQ ID NO: 55           moltype = DNA   length = 53
FEATURE                 Location/Qualifiers
source                  1..53
                        mol_type = other DNA
                        organism = synthetic construct
SEQUENCE: 55
atccaatcca attaaattag attagattag attagattag attagattag aca        53

SEQ ID NO: 56           moltype = DNA   length = 53
FEATURE                 Location/Qualifiers
source                  1..53
                        mol_type = other DNA
                        organism = synthetic construct
SEQUENCE: 56
taggttaggt taatttaatc taatctaatc taatctaatc taatctaatc tgt        53

SEQ ID NO: 57           moltype = DNA   length = 53
FEATURE                 Location/Qualifiers
source                  1..53
                        mol_type = other DNA
                        organism = synthetic construct
SEQUENCE: 57
atccaatcca attaaattag attagattgg attagattag attagattag aca        53

SEQ ID NO: 58           moltype = DNA   length = 77
FEATURE                 Location/Qualifiers
source                  1..77
                        mol_type = other DNA
                        organism = synthetic construct
SEQUENCE: 58
gtccaatcca atccaatcca atccaatcca atccaattaa attagattag attagattag  60
attagattag attagac                                                 77

SEQ ID NO: 59           moltype = DNA   length = 77
FEATURE                 Location/Qualifiers
source                  1..77
                        mol_type = other DNA
                        organism = synthetic construct
SEQUENCE: 59
gtccaatcca atccaatcca atccaatcca atccaattaa attggattgg attggattgg  60
attggattgg attggac                                                 77

SEQ ID NO: 60           moltype = DNA   length = 1188
FEATURE                 Location/Qualifiers
source                  1..1188
                        mol_type = other DNA
                        organism = synthetic construct
SEQUENCE: 60
atttaggtga cactatagaa tacaagctac ttgttctttt tgcaggatcc gccaccatgt   60
atccgtacga cgtaccggat tatgcgatgt tgagcaaggg cgaggagctg ttcaccgggg  120
tggtgcccat cctggtcgag ctggacggcg acgtaaacgg ccacaagttc agcgtgtccg  180
gcgagggcga gggcgatgcc acctacggca agctgaccct gaagttcatc tgcaccaccg  240
gcaagctgcc cgtgccctgg cccaccctcg tgaccaccct cggctacggc ctgcagtgct  300
tcgcccgcta ccccgaccac atgaagcagc acgacttctt caagtccgcc atgcccgaag  360
gctacgtcca ggagcgcacc atcttcttca aggacgacgg caactacaag acccgcgccg  420
aggtgaagtt cgagggcgac accctggtga accgcatcga gctgaaggc atcgacttca  480
aggaggacgg caacatcctg ggcacaagc tggagtacaa ctacaacagc cacaacgtct  540
atatcatggc cgacaagcag aagaacggca tcaaggtgaa cttcaagatc cgccacaaca  600
tcgaggacgg cagcgtgcag ctcgccgacc actaccagca gaacacccc atcggcgacg  660
gccccgtgct gctgcccgac aaccactacc tgagctacca gtccgccctg agcaaagacc  720
ccaacgagaa gcgcgatcac atggtcctgc tggagttcgt gaccgccgcc gggatcactc  780
tcggcatgga cgagctgtac aagtagctcg agcctctaga actatagtga gtcgtattac  840
acactctttc cctacacgac gctcttccga tctgccaacg ctattctggc tgatgtatat  900
atgtaaatat ctatccaacg caattctggc acgtccaatc caatccaatc caatccaatc  960
caatccaatt aaattagatt agattagatt agattagatt agattagaca ggccttgatc 1020
ggaagagcac acgtctgaac tccagtcact acgtagtaga tccagacatg ataagataca 1080
ttgatgagtt tggacaaacc acaactgaaa tgcagtgaaa aaaatgcttt atttgtgaaa 1140
tttgtgatgc tattgcttta tttgtaacca ttataagctg caataaac              1188

SEQ ID NO: 61           moltype = DNA   length = 75
FEATURE                 Location/Qualifiers
source                  1..75
                        mol_type = other DNA
```

```
                     organism = synthetic construct
SEQUENCE: 61
tccaatccaa tccaatccaa tccaatccaa tccaattaaa ttagattaga ttagattaga    60
ttagattaga ttaga                                                     75
```